United States Patent [19]
Johnson et al.

[11] Patent Number: 5,050,983
[45] Date of Patent: Sep. 24, 1991

[54] VISUAL TESTING METHOD AND APPARATUS

[75] Inventors: Chris A. Johnson; Lionel R. Shapiro, both of Davis, Calif.

[73] Assignee: The Regents of the University of California, Oakland, Calif.

[21] Appl. No.: 517,660

[22] Filed: Apr. 30, 1990

[51] Int. Cl.$^5$ ............................................. A61B 3/02
[52] U.S. Cl. ..................................... 351/226; 351/224
[58] Field of Search ........................ 351/224, 225, 226

[56] References Cited

PUBLICATIONS

Heijl, A. "Computer Test Logics for Automated Perimetry," Acta Ophthalmoligica, 55:837, 3/1977.
Johnson, C. A. "The Test Logic of Automated Perimetry", Acta: XXIV International Congress of Opthalmology, Henkind (ed.), J. B. Lipincott, Philadelphia, 1983.
Johnson, C. A., Keltner, J. L., "Incidence of Visual Field Loss in 20,000 Eyes and its Relationship to Driving Performance," Arch. Opthalmol, vol. 101, pp. 371-375, Mar. 1983b.
Johnson, C. A., Adamsm C. W., & Lewis, R. A., "Fatigue Effects in Automated Perimetry," Applied Optics, vol. 27, pp. 1030-1037, Mar. 1988.
Keltner, J. L., Johnson, C. A., "Comparative Material on Automated and Semi-Automated Perimeters," Opthalmology, vol. 93, pp. 1-25, 1986.
Lewis, R. A. et al., "Preliminary Clinical Trials with the Humphrey Field Analyzer," Doc. Opthalmol. Proc. Ser., vol. 42, pp. 159-165, 1985.
Shapiro, L. R., Johnson. C. A., & Kennedy, R. L., "KRACKEN: A Computer Simulation Procedure for Static, Kinetic, Suprathreshold Static and Heuristic Perimetry," In A. Heijl (ed.), Perimetry Update 1988/89: Proceedings of the VIIIth International Perimetry Society Meeting. Asterdam: Kuglar & Ghedini, pp. 431-438, 1989.
Tyrrell, R. A., & Owens, D. A., "A Rapid Technique to Assess the Resting States of the Eyes and Other Threshold Phenomena: The Modified Binary Search (MOBS)," Behavior Research Methods, Instruments & Computers, vol. 20, pp. 137-141, 1988.

Primary Examiner—Rodney B. Bovernick
Attorney, Agent, or Firm—Peter J. Dehlinger

[57] ABSTRACT

Method and apparatus for visual testing. In one embodiment, for perimetry testing, the method uses threshold light-stimulus values determined at multiple seed locations in a visual field to calculate expected stimulus threshold values at locations which are nearest-neighbors of the seed locations. The expected values at the nearest-neighbor locations are compared with subject responses at these locations, and the correspondence between the two is used to refine and guide line stimulus level presentations at the nearest-neighbor locations. The test is continued until a selected confidence level of response at nearest-neighbor locations is reached.

15 Claims, 10 Drawing Sheets

● SEED LOCATION
○ EXPECTED NOT-SEEN
O EXPECTED SEEN

VISUAL TESTING METHOD AND APPARATUS

FIELD OF THE INVENTION

The present invention relates to visual testing, and particularly, to a method and apparatus which employs an optimized test-location sequence for real time interactive visual testing.

REFERENCES

Anderson, D. R., *Perimetry With and Without Automation*, C. V. Mosby, St. Louis, 1987.

Hecht, E., *Optics*, Addison Wesley, 1987.

Heijl, A., "Computer test logics for automated perimetry," *Acta Ophthalmoligica*, 55:837, 1977.

Johnson, C. A., "The Test Logic of Automated Perimetry" in *Acta: XXIV International Congress of Ophthalmology*, Henkind (ed.), J. B. Lipincott, Philadelphia, 1983a.

Johnson, C. A., Keltner, J. L., "Incidence of Visual Field Loss in 20,000 Eyes and its Relationship to Driving Performance," *Arch. Opthalmol.*, vol. 101, pages 371-375, 1983b.

Johnson, C. A., Adams, C. W., & Lewis, R. A., "Fatigue Effects in Automated Perimetry," *Applied Optics*, vol. 27, pages 1030-1037, 1988.

Keltner J. L., Johnson, C. A., "Comparative Material on Automated and Semi Automated Perimeters," *Ophthalmology*, vol. 93, pages 1-25, 1986.

Lewis, R. A., et al., "Preliminary Clinical Trials With the Humphrey Field Analyzer," *Doc. Ophthalmol. Proc. Ser.*, vol. 42, pages 159-165, 1985.

Shapiro, L. R., Johnson, C. A., & Kennedy, R. L., "KRAKEN: A Computer Simulation Procedure for Static, Kinetic, Suprathreshold Static and Heuristic Perimetry," In A. Heijl (Ed.), *Perimetry Update 1988/89: Proceedings of the VIIIth International Perimetry Society Meeting*. Amsterdam: Kugler & Ghedini, pages 431-438, 1989.

Tyrrell, R. A., & Owens, D. A., "A Rapid Technique to Assess the Resting States of the Eyes and Other Threshold Phenomena: The Modified Binary Search (MOBS)," *Behavior Research Methods, Instruments, & Computers*, vol. 20, pages 137-141, 1988.

BACKGROUND OF THE INVENTION

Visual tests to determine a subject's response to such variables as light intensity, color or stimulus size or to spatial or temporal patterns are common in ophthalmic examinations. One widely used visual test, known as perimetry testing, is designed to determine the range and sensitivity of a subject's visual field (Anderson, 1987; Johnson, 1983a). Many diseases of the eye, e.g., glaucoma or optic neuropathies, affect field of vision, and often these diseases are evidenced at an early stage, when treatment may be most effective. Additionally, the type and extent of many eye diseases, and the location of the disease along the visual pathway (i.e. the eye, the optic nerve, or the visual centers of the brain) can often be determined by visual- field examination.

In standard static perimetery testing methods, the visual field is partitioned into a number of discrete locations and the subject's threshold to visual stimuli at each of the locations is determined. Heretofore, this has been done by one of two methods. In a first approach, known as the accending methods of limits, the subject is presented with a series of stimuli of step-wise increasing intensity levels, until an "unseen" stimulus is first seen. This first seen stimulus intensity determines the visual threshold. In a second approach, known as the staircase method, the subject is presented with a series of stimuli of step- wise increasing intensity levels, until an "unseen" stimulus is first seen. Thereafter, the direction of the "staircase" is reversed, until a lower limit of detection is determined. The threshold is then refined and confirmed by two additional reversals of stimulus intensity. The staircase method involves at least 5 stimulus presentations at each location. Because of the additional reversals of stimulus intensity the staircase procedure is more accurate and reliable then the accending method of limits.

A more accurate method for determining intensity threshold is by a Modified Binary Search (MOBS), a method proposed by Tyrrell et al. (1988). This procedure has been used for measuring visual thresholds, but has not previously been applied to visual field testing. In this method, a selected-intensity stimulus, typically near the expected threshold level of the subject is presented, and depending on whether the stimulus is seen, that stimulus becomes the upper or lower threshold boundry. The intensity range is then divided up into a series of increasingly smaller half- intervals until the upper (seen) and lower (not seen) threshold boundries are within a defined range, e.g., 4 dB.

In prior-art perimetry methods, threshold values—either by the accending method of limits or the staircase procedure—are determined at each location in the visual field. The test method is therefore relatively time-consuming, in that many stimuli must be presented at each location. Typically, the time required for complete testing is between 15-30 minutes. Studies have shown a loss of reliability with increasing test time, which can be accounted for by fatigue factors (Johnson et al., 1988). This problem is aggravated in older patients, the group for whom perimetry testing is generally most important. In addition, the point-by-point approach lacks an efficient method of error correction, in that bad guesses or patient mistakes during the test can only be estimated by additional "catch" trials. Suspicious test values at any location can only be checked by a full retesting of the location after the field has been completely tested.

SUMMARY OF THE INVENTION

It is one general object of the invention to provide a visual test method and apparatus which substantially reduces the number of visual stimulus presentations which must be conducted to generate a reliable visual test of a subject.

A more specific object of the invention is to provide such a method and apparatus which employs real-time control of test locations and test stimuli to enhance test efficiency and reliability.

The method of the invention is designed for testing a subject's threshold response level to a visual stimulus of the type which can be presented to the subject at a selected level and at selected locations in a two-dimensional field. The selected level of stimulus may encompass, for example, different light intensities, colors, spatial frequencies, or temporal frequencies. The two-dimensional field may encompass a two-dimensional spatial field (for perimetry testing). Alternatively, one or both of the dimensions of the field may encompass non-spatial stimulus parameters, such as color or temporal frequency of the stimulus.

In practicing the method, the two-dimensional field is partitioned into an array of N locations composed of S seed locations and N-S non-seed locations, where each seed location has multiple non-seed nearest-neighbor locations. At each seed location, threshold testing is employed. Using the threshold ranges determined at each seed location, the expected threshold of detection by the subject at each nearest-neighbor non-seed location is calculated, preferably from (a) the thresholds of nearby seed locations, (b) the distances of the nearest-neighbor location from the nearby seed locations, and (c), a position-related change in threshold which would be expected in an average subject.

The subject is then presented, at the non-seed locations, a visual stimulus which is a selected level above or below the expected threshold of detection for that non-seed location, depending on whether that non-seed location has been assigned to a super- or sub-threshold group, respectively. In one preferred embodiment, the field locations are in a regular checkerboard array, such that each location is bordered by four orthogonal nearest-neighbor locations which are assigned to one threshold group, and four diagonal nearest-neighbor locations which are assigned to the other threshold group.

The response of the subject to the stimulus presented at each nearest-location is recorded as "seen" or "not seen" by the subject. These responses are then used to classify the neighbor agreement between each location in the field and its nearest neighbors into a "discrepancy," "low-confidence," or "high-confidence" category. If the pattern of neighbor agreement at any location is in the "discrepancy" category, that location is retested for a "seen"/"not-seen" response. If the pattern of neighbor agreement for a non-seed location is in the "low-confidence" category, the expected threshold of that location is adjusted to a revised expected threshold value.

The invention further includes an apparatus for testing a subject's threshold response level to a visual stimulus, according to the above method. The apparatus includes a stimulus device designed to present a selected-level stimulus at each of N locations in a two-dimensional visual field array, and a recorder for recording a subject's response to the stimuli.

A control unit in the apparatus operates to: (1) store, at each of S seed locations in the N location array, a subject's upper and lower threshold boundries of stimulus detection, (2) calculate, for each of N-S non-seed nearest neighbor locations in the array, the expected threshold of detection by the subject, based on the values stored in said storing means, (3) present to the subject, at each non-seed location, a visual stimulus which is either a selected level above or below the expected threshold of detection for that non-seed location, depending on whether that non-seed location has been assigned to a super- or sub-threshold group, respectively, (4) classify the neighbor agreement between each location in the field and its nearest neighbors into a "discrepancy," "low-confidence," or "high-confidence" category, (5) if the pattern of neighbor agreement at any location is in the "discrepancy" category, retest that location for a "seen"/"not seen" response, and (6) if the pattern of neighbor agreement for non-seed locations is in the low-confidence category, adjust the expected threshold of that location to a revised expected threshold value, and recalculate the nearest-neighbor agreement between the revised-threshold location and its nearest neighbors.

These and other objects and features of the present invention will become more fully apparent when the following detailed description of the invention is read in conjunction with the accompanying drawings.

DETAILED DESCRIPTION OF THE INVENTION

Figure 1:
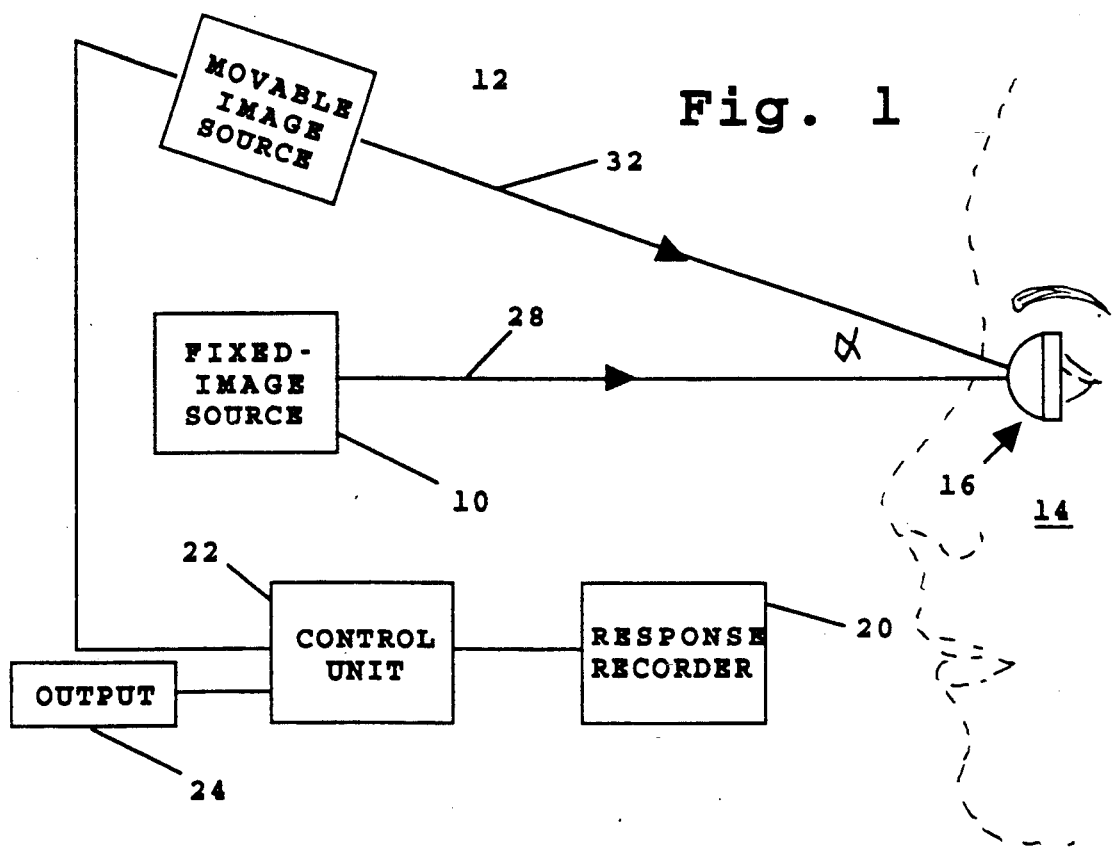
FIG. 1 is a schematic view of an apparatus for perimetry testing, in accordance with the invention.

FIG. 1 is a schematic illustration of a perimetry test employing the method and apparatus of the invention. Shown at 10 and 12 in the figure are fixed- and movable-position image sources, respectively, for presenting selected-image stimuli to a subject 14. In a preferred embodiment, images are viewed through an ocular 16 which allows the images to be viewed without corrective lenses, as described in co-owned U.S. patent application Ser. No. 482,278, filed Feb. 20, 1990.

The images observed by the subject are recorded by a response recorder 20 in the apparatus, and these responses are passed to a control unit 22 which evaluates the responses and controls the stimulus presentation to the subject, in accordance with the present invention, to determine a visual threshold map. The results may be displayed on an output 24. The visual test method, and its control by unit 22, will be described in Section B. Apparatus for carrying out the method, including a preferred stimulus-presentation system, recorder 20 and control unit 22 will be detailed in Section C. Section A gives a guide to the Appendices which include the software commands used in the apparatus for real-time evaluation of the testing results and static perimetru test presentations.

A. Guide to the Appendices

In the appendices, the source code for RIOTS and necessary support procedures are in the Turbo Pascal (version 5.0) language.

RIOTS (Appendix A)

RIOTS (Real-Time Interactive Optimized Test Sequence) includes the heuristic strategy for static perimetry, in accordance with the method of the invention, and as detailed in Section B. Details of the method will be given with reference to the various sections of the RIOTS program which are indicated in the text.

KRAKEN (Appendix B)

KRAKEN is a general simulation and control program for evaluation of perimetric strategies and devices (Shapiro et al., 1989). KRAKEN is the supervisory program from which support procedures are called to handle specific tasks. These tasks include: (1) user interaction for the determination of operational parameters; (2) file preparation; (3) device or simulation initialization; (4) execution of specific strategies; and (5) recording of operational variables as well as test results.

Routines for user interaction (that is, the control and display of operational parameters used by KRAKEN and its support routines), file preparation and device or simulation initialization include:

KRMENU

Initializes a menu system (Turbo Professional routines, TP-prefix, provide the specific control) for choosing options in the control of KRAKEN, see also SIMPARAM for implementation of choice options. KRMENU is called by KRAKEN only.

PLOTPAK

Provides for graphical output of operational parameters and variables. This code contains a library of routines for specific graphic output tasks. These routines may be called from any number of points within any of the routines which follow.

TIMELIB

Provides routines for accessing and displaying time and date variables. These routines may be called from any number of points within any of the routines which follow.

PADPAK

Provides routines for control and information retrieval from a graphics input device such as a Summagraphics Bit Pad. This allows the operator of KRAKEN to control placement and levels of stimuli when KRAKEN is in a manual mode of operation. These routines are called primarily from the RESPN library (see below).

TRIG

Provides routines for trigonometric calculations. These routines may be called from any number of points within any of the routines which follow.

DWIGHT

Provides routines for control of device described in co-owned U.S. patent application Ser. No. 482,278, filed Feb. 20, 1990. These routines are called primarily from the RESPN library (see below).

GLOBALS

Defines and initializes some operational and all functional parameters and structures used by all of the following routines.

RANDOMZ

An initialization routine to provide for uniformly distributed random number generation. This allows the simulation portions of KRAKEN and its supporting routines to generate a reasonable simulation of events with constrained random variation. These routines are called primarily from the RESPN library (see below).

RESPN

KRAKEN may either simulate a patient or collect responses from an actual patient; and either simulate a perimetric device or control and receive patient responses from an actual perimetric device. This library of routines contains two types of response procedures: simulation of patient o interfacing control with actual devices. These routines are called through a standard routine called RESPOND which diverts control to the appropriate support routine based upon the specified operational parameters.

GNAME

This simply allows for operator entry of file names.

HC30—2

This consists of a definition of a data structure for the 30-2 test pattern. This data provides a list of neighbor groups for each of 76 locations in the test pattern.

SIMPARAM

This code provides the remaining definitions and initializations of operational parameters. The code also contains a routine which allows for modification of a number of these parameters via a menu oriented system (see KRMENU above). Code defined here is called from the KRAKEN main routine only.

MIN MAX

Simple support routines for determination of minimum and maximum values given a specified pair of values.

USTATIC

Support routines for static-type perimetry operation. For example, the display of parameters and variables specific to static stimuli presentations.

PAUSE

A simple routine to allow for operator controlled pauses in program execution.

KREXIT

Program control code to be executed upon the call for program termination.

PLOTMAN

Provides a routine for graphical display of a manifold (visual field and related information) data structure.

INIMOD

Initializes file and control variables associated with patient and reference files (see also normal reference files below).

REPORT

Called to output, in a variety of formats, data obtained through the application of the perimetric strategies via either simulation or device control.

The following are strategy code modules for simulation of specific perimetric devices or procedures:

SIMPLEST

This is the strategy code for a simple stair case procedure for static

HUMCEN30

This is the strategy code for a simulation of the type similar to the Humphrey Full Threshold (staircase) procedure for static perimetry.

MOBSC30

This is the strategy code for a modified procedure for static perimetry

SUPRA30

This is the strategy code for a simple suprathreshold static screening perimetric procedure.

Files (Appendix C)

In order to run the KRAKEN package, access must be made to normal sensitivity reference files. These data are calculated from statistical summaries of population data for specific perimetric tests. Appendix C contains reference files (for 7 age groups) for a typical test pattern used in the present invention; this layout information is redundant with the support file: CEN30-b 2.GRD). Any remaining references to additional support files may be ignored as they do not pertain to the execution of the RIOTS procedure with non-simulated perimetric devices.

B. Visual Testing Method

1. Partitioning the Visual Field

The method is designed for visual testing by light stimuli which can be represented as selected value points in a multi-variable space. In the typical case of perimetry testing, the stimuli are static light stimuli which are presented at selected locations in a two-dimensional spatial field. The static stimuli may vary, for example, in intensity, size, or color. Thus, the multi-variable space includes two spatial dimensions and a stimulus-variable dimension. Alternatively, in perimetry testing, the stimuli may themselves may be defined by two or more variables, such as intensity and color, giving a four dimensional test space.

Another type of multi-variable visual testing which is adaptable to the present invention involves a subject's ability to distinguish bar patterns having different spatial and temporal frequencies, and intensities. For example, the subject may be presented with a bar pattern having a selected intensity, bar spacing and flicker frequency, and these three parameters are varied to determine threshold values at different positions in the three-dimensional test space.

More generally, the present invention is useful in visual testing in which the threshold response of one type of visual stimulus is displayed at selected "locations" in a two- or higher-dimension test space. The test space may be defined by spatial coordinates, such as a two-dimensional visual field, by non spatial coordinates, such as spatial and temporal frequencies in the bar pattern, or by a mixture of spatial and non-spatial coordinates, such as a two-dimensional visual field containing a third light-stimulus variable, such as color.

For purposes of illustration, the test space described herein is a two-dimensional visual field defined by the projection of x and y coordinates on a hemispherical cap region. An exemplary test field is shown at 30 in FIG. 2. The outer boundary of the field is defined by the perimeter of a cone formed at a 30° angle from the horizontal line of sight of the subject, as illustrated by the angle alpha in FIG. 1. As seen, the cap region is divided into four quadrants containing an equal number of test locations, such as locations 40, 42, 44, 46, 48, 50, and 52. The locations 40–52 and the two locations on either side of location 52 form a nine-location array 53 of locations representative of the ones which are shown in the figure. Each of the locations are equally spaced from one another, along horizontal and vertical axes, in a two-dimensional projection, as illustrated.

Figure 2:
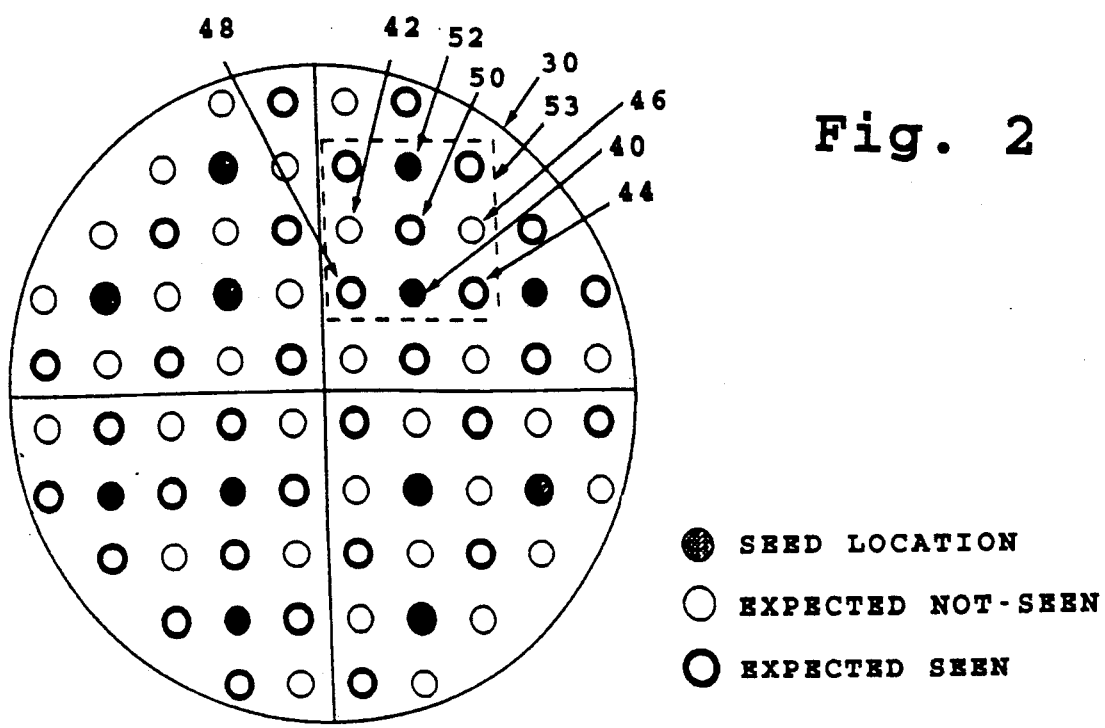
FIG. 2 shows the partitioning of a two-dimensional spatial field for perimetery testing, in accordance with the method of the invention.

With continued reference to FIG. 2, the array of locations such as location 40, are subdivided into S seed ("S") locations, and N-S non-seed locations. Here the number of seed and non-seed locations is 12 and 64, respectively. As seen, each location other than an edge location has eight nearest neighbors, four of which are horizontal or vertical nearest neighbors and four of which are diagonal nearest neighbors. For example, the nearest neighbors of seed location 40 (filled circle) in array 53 are locations 48, 42, 50, 46, and 44 which are indicated with thick circles (horizontal and vertical nearest neighbor locations) and thin circles (diagonal nearest neighbors).

The projection of the above array of locations in a two-dimensional plane can also be thought of as a checkerboard array in which each location, such as location 50, has four same-color nearest neighbors (the diagonal nearest neighbors) and four different-color nearest neighbors (the vertical and horizontal nearest neighbors).

It will be appreciated that other arrangements of locations in two-dimensional space are possible. For example, the locations may be arranged in a regular hexagonal array with each point surrounded by three immediate nearest neighbors and nine more removed nearest neighbors. More generally, the method requires a partitioning of the space into locations which each have multiple nearest neighbor locations which can be assigned to two threshold groups, as discussed below.

2. Determining Seed Location Values

In the first phase of the test method, the threshold range of detection of a visual stimulus by the subject is determined at each seed location in the test field. As noted above, the visual stimulus may relate to light intensity, color, size, or spatial or temporal frequency. Regardless of the nature of the stimulus, the threshold test is carried out to determine the lower and upper threshold boundries of perception of the stimulus by the subject. Thus, in the case of light-intensity stimuli, the testing is carried out to determine the least upper bound and greatest lower bound of intensity which is perceived by the subject, at a given location.

Figure 3:
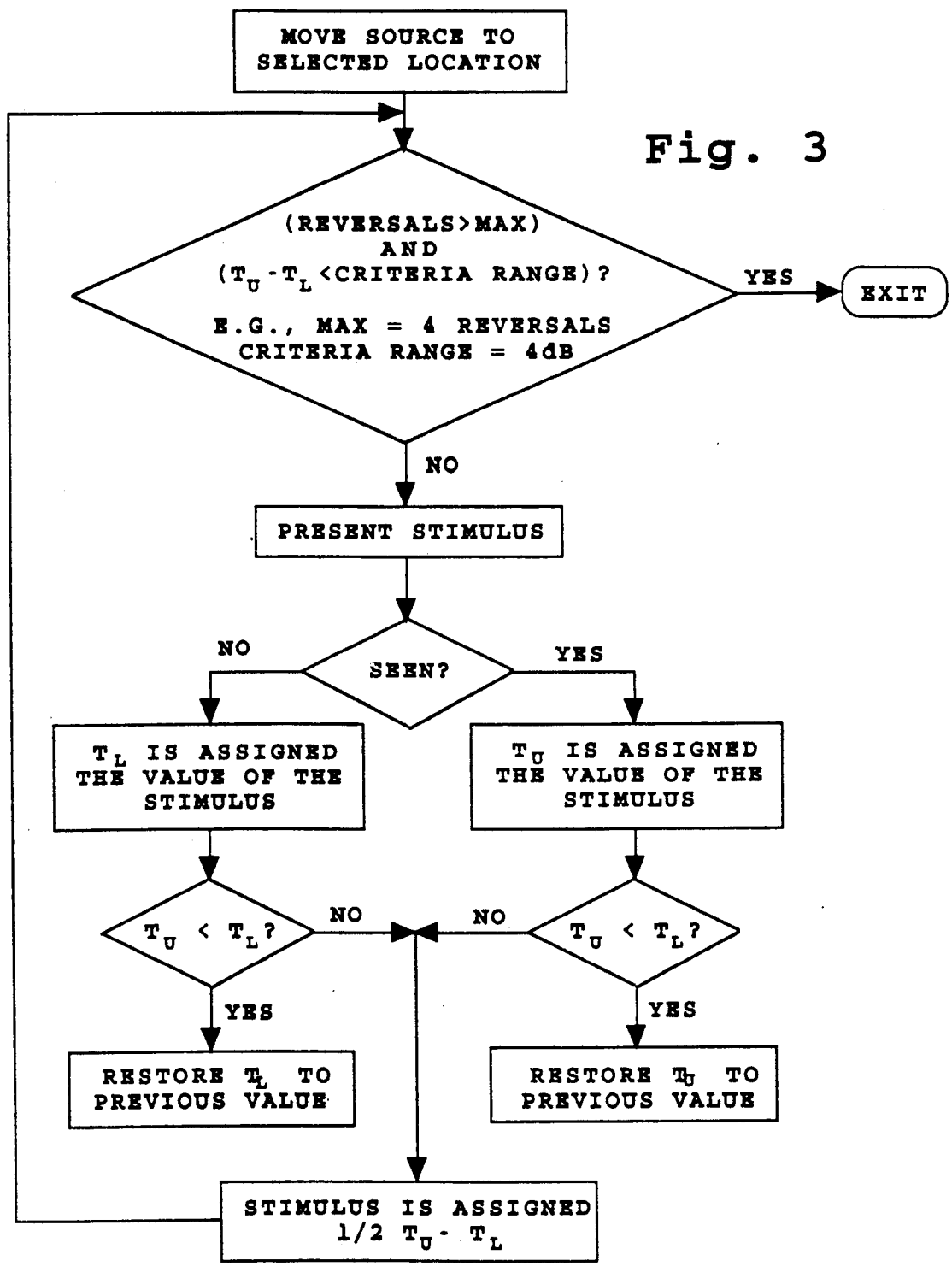
FIG. 3 is a flow diagram of steps for determining a threshold intensity range at each seed location.

The method preferably employs a reliable method for threshold determinations, such as a staircase or modified binary search (MOBS ["MOBS" function on pp. 2–6, Appendix A]) mode of testing, as have been described (Tyrrell). A preferred test procedure, for use in determination of light intensity threshold, employs a variant of the MOBS approach, as outlined in FIG. 3. In the procedure, a light source is placed at a selected seed location in the field (Section C below). The source is controllable to output a selected-size image, typically, 1 to 4 mm, as viewed from a distance of 0.33 meters, for a selected time interval, e.g., 100 to 500 msec, over a selected intensity range, typically between about 0 to 40 dB.

The first light stimulus which is presented to the subject at a seed location has an intensity which is $\frac{2}{3}$ along the interval between the absolute lower (L) and upper (U) boundries of light intensities of the source. More generally, the intensity is biased somewhat in favor of receiving a "seen" response from the subject. Assuming the result is seen, the first presented intensity becomes the current upper threshold boundry $T_u$, and the intensity is reduced by $\frac{1}{2}$ the interval between $T_u$ and the lower boundry. That is, the second stimulus intensity is $\frac{1}{2} T_u - T_l$, where $T_l$ is the current lower boundry, which is at this point the lower bound L. This step represents a first reversal in direction of intensity. If the first stimulus is not seen, this first stimulus intensity becomes the current lower bound $T_l$ and the next stimulus which is presented has an intensity halfway between this value and the highest intensity. This step is not counted as a change in direction. These steps are shown at the top in FIG. 3.

If the second stimulus is lower intensity, and not seen, this second-stimulus intensity becomes the new lower current bound $T_l$, and the next intensity is similarly set halfway between the current $T_u$ and $T_l$. This step represents a second change in direction. If the second stimulus is higher intensity, and seen, this second-stimulus intensity becomes the new upper current bound $T_u$, and the next intensity is similarly set halfway between the current $T_u - T_l$. This step also represents a reversal in direction.

If at any time the lower boundry goes above the upper boundary then the upper boundary is reset to its previous value. Similarly, if the upper boundary goes below the lower boundary then the lower boundary is reset to its previous value. This is handled by a LIFO (last in, first out) stack queue data structure.

This procedure is carried out until a total of at least R (e.g., R=4) reversals in direction, and a defined specific interval between upper and lower stimulus boundaries is achieved. The four reversals require at least five different-intensity presentations, and typically less than 8 presentations to achieve a preferred upper and lower boundary interval of about 4 dB. The steps are indicated in flow diagram form in FIG. 3. A threshold value $T_i$ for each seed point $S_i$ is calculated as the average of the $T_l$ and $T_u$ values.

It will be appreciated how the above modified MOBS procedure can be applied for determining threshold values of other types of visual stimuli, such as temporal or spatial frequency of a spaced-bar stimulus.

The threshold range determined at each seed point is stored in the control unit, for use in calculating expected threshold values of neighboring non-seed locations, as will now be described.

3. Calculating Expected Non-Seed Threshold Values

After the threshold value of each seed point has been established, the control unit operates to calculate expected thresholds at each of the non-seed locations, based on the threshold values measured at the neighboring seed locations. The flow diagram in FIG. 4 ["open-neighbors" function on pp. 11-12, Appendix A] shows an exemplary procedure for calculating expected intensity thresholds for non-seed locations. The procedure looks at each non-seed location $N_j$ location, and retrieves the threshold values $T_i$ of each nearest neighbor seed point $S_i$. With reference to FIG. 2, for example, the nearest-neighbor seed locations of non-seed location 50 are the seed points 40, 52. Other non-seed points may have only one immediately neighboring seed point.

The threshold $T_{si}$ of each such seed point is then compared with a "normal" value $T_{ni}$ for that i location in the visual field, based on a statistical sampling of individuals with normal field of vision. If the measured and normal values are equal or nearly equal, the expected threshold value for the location $E_j$ with respect to the seed point $S_i$ is set equal to the normal value $E_{nj}$ expected at the non-seed location.

If, however, the measured and normal values at a neighboring seed location are not substantially equal, the program calculates an expected value $E_j$ which is based on the measured seed threshold and the distance between the seed location $S_i$ and non-seed location $N_j$. This calculation uses the empirical formula:

$$E_j = T_i (0.3 \text{ dB/degree})(\text{radius of } N_j - \text{radius of } S_i),$$

where the radii of $N_j$ and $S_i$ refers to the degrees of eccentricity of the locations away from the center of the visual field. Thus all points on the perimeter of the visual field array shown in FIG. 2 have an eccentricity of 30°. The 0.3 dB/degree constant may be slightly greater or smaller if stimulus parameters are employed.

After the value $E_j$ has been calculated with respect to each nearest-neighbor of the $S_i$ location, as above, the expected threshold values are averaged ["average-neighbors" function on pp. 7-8, Appendix A] to produce an expected value $E_j$ for that non-seed location. These values are then stored for use in visual stimulus presentations.

4. Stimulus Presentation

Each location in the test field array has now been assigned a stimulus threshold value: For seed locations, that value was determined directly by testing the threshold value of stimulus detection of the subject. For the remaining, and more numerous non-seed locations, the threshold value was an expected value calculated from neighboring seed values.

Figure 5:
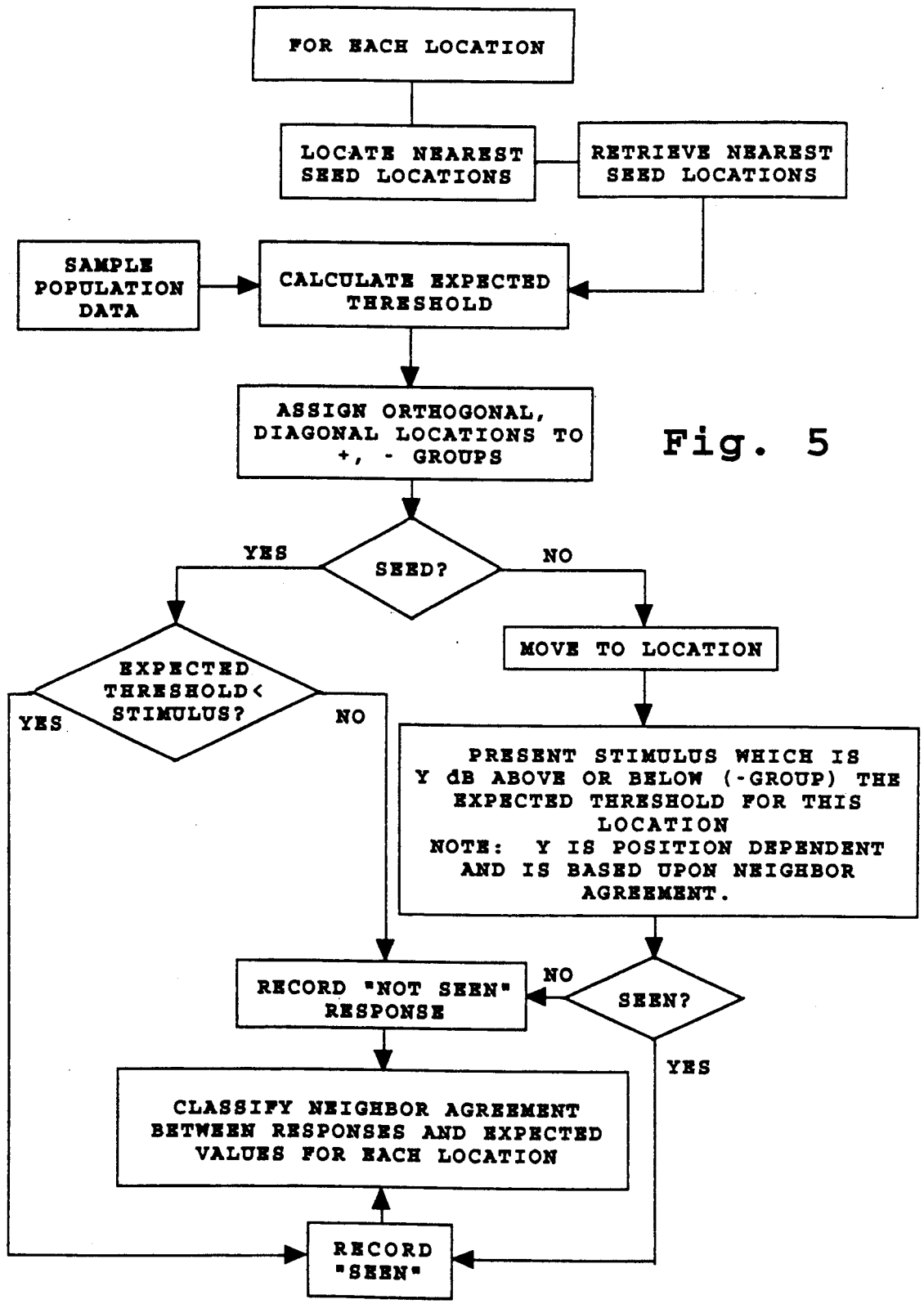
FIG. 5 is a flow diagram of steps for measuring the correspondence between expected and recorded threshold levels at all locations.

In the next step of the method, described in flowchart FIG. 5 ["Pass 1 or 2" function, lines 14 to 56, Appendix A], a test stimulus is presented to the subject at each of the non-seed locations, to confirm or refine the expected threshold value at that location. According to an important aspect of the stimulus presentation step, the non-seed locations in the test array are divided into two groups: a sub- threshold group at which below-threshold stimuli will be presented to the subject, and a super-threshold group at which above-threshold stimuli will be presented. For purposes of obtaining reliable neighbor agreement patterns, each location in the test array, including both seed and non-seed points, is preferably surrounded by (nearest neighbors of) two or more non-seed locations in each group.

In a preferred configuration, illustrated in FIG. 2, each internal seed location has eight nearest neighbors, with the non-seed locations which are orthogonal to the central seed location being assigned to one group and the diagonal nearest neighbors being assigned to the other group. For example, seed location 40 is surrounded by orthogonal neighbors represented by thick circles and diagonal neighbors represented by thin circles. Viewing the array of locations as a checkerboard, all the locations of one "color" are assigned to one group, and the locations of another "color," to the second group. As will be seen below, the locations of the two groups are reversed in different test phases.

The stimulus presented at a non-seed location in a sub-threshold group is a selected level below the threshold calculated for that location. By way of illustration, where the stimulus is a light flash of a selected intensity, the intensity of the stimulus is a selected level, e.g., 4 dB, below the calculated intensity threshold of the given non- seed location. The selected level below threshold is such as to guarantee a strong likelihood of obtaining a confirming response, that is, a "non-seen"

response, from a normal subject when presented with the sub-threshold stimulus at a given location.

Similarly, the stimulus presented at each non-seed location in a super-threshold group is a selected level above the calculated threshold for that location, and preferably the same selected level, e.g., 4 dB for intensity testing, as applied to the sub-threshold group.

The sequence of stimulus presentation at the non-seed locations is preferably random, at least from the point of view of the subject, so that successive presentations are typically widely spaced over the test field, and sub-threshold stimuli are mixed randomly with super-threshold stimuli. This prevents the subject from concentrating on any area within the field, or expecting a stimulus within any area of the field or within any time interval. In one preferred device for stimulus presentation, discussed in Section B below, the successive light flashes are presented on an average of every 1 to 2 seconds.

Each "seen" stimulus presentation is recorded by the subject, typically by means of a hand-held pushbutton switch connected to recorder 20. A non-response is of course recorded in the recorder as a "non-seen response." The responses are stored in the control unit until all of the non-seed locations have been tested.

The procedure for testing the non-seed locations just described applies to a first-phase test in which all of the non-seed locations are tested at a fixed, selected level above or below the estimated threshold for each location. As described below, the method preferably involves a second- phase test in which the sub- and super-threshold assignments are reversed and the selected stimulus levels above and below expected thresholds are tailored to the confidence level at each non-seed location. The method also contemplates a third test phase in which the non-seed locations are returned to their original group assignments, and only points outside of a given confidence level are tested. The stimulus presentation in these second-and third-phase tests will be clear from the description of the tests below.

5. Classifying Neighborhood Patterns

At the conclusion of each test phase in the method, the locations in the test array are analyzed for agreement with nearest neighbors, to confirm or refine the threshold value tested during that test phase. Depending on the pattern of neighborhood agreement which is observed at a location, the location is classified into one of at least two, and preferably three, "confidence" categories, according to the agreement between that location and the immediate nearest neighbors. The two basic categories are a "low-confidence" and "high-confidence" class used to characterize those locations in which the agreement between a location and its nearest neighbors is below and above a selected confidence limit, respectively. The third class is a "discrepancy" category in which the location is in disagreement, typically complete disagreement, with its nearest neighbors.

In one general procedure for classification of neighbor agreement, each location in the test field is evaluated for self-consistency between expected and recorded thresholds, and for pairwise-consistency with its nearest neighbors. A location is self-consistent if it is (a) a non-seed location which is expected seen (superthreshold group) and is recorded as "seen," (b) a non-seed location which is expected not-seen (subthreshold group) and is recorded as "not-seen," or (c) a seed location (which is self-consistent by definition). A location is self-inconsistent if it is (a) a non-seed location which is expected seen (superthreshold group) and is recorded as "not-seen," or (b) a non-seed location which is expected not-seen (subthreshold group) and is recorded as "seen."

A pair of locations are pairwise-consistent if the locations are both self-consistent or self-inconsistent. The pair is pairwise-inconsistent if one of the pair is self-consistent, and the other self-inconsistent. Thus for example, with reference to FIG. 2, if non-seed point 44 is self-inconsistent and nearest-neighbor seed location 40 is self-consistent (as it must be), the two locations are scored as pairwise inconsistent. On the other hand, if non-seed point 46 is also self-inconsistent, then locations 44, 46 are scored as pairwise consistent.

The scoring algorithm considers each location in the array, scores the neighborhood agreement, based on a total pairwise consistency score, classifies that location into one of the possible confidence classes, then moves on to the next location in the array. To illustrate, the operation of the algorithm at non-seed point 50 will be considered. Here it is assumed that this location was expected seen (super-threshold group), but was recorded as "not-seen," indicating that the original calculated expected threshold for this location is too high. That is, the location is self-inconsistent.

The algorithm then performs a pairwise comparison between location 50 and each of the eight nearest neighbor locations, such as locations, 52, 48, 40, and 42. For purposes of illustration, it will be assumed that locations 52 and 40 are self-consistent (because they are seed points), location 50 is self-inconsistent (because it was expected "seen" and recorded as "not-seen"), location 44 is self-consistent (because it was expected "seen" and recorded as "seen"), and location 46 is self-inconsistent (because it was expected "not-seen" and was recorded as "seen"). Therefore, the pairwise score for locations 50, 44, is pairwise- inconsistent; for locations 50, 40 is pairwise-inconsistent; and for locations 50, 46, pairwise-consistent.

Notice that in the present case where the center location 50 is self-inconsistent, a non-seed location, such as location 46 may be self-inconsistent but pairwise consistent or may be self-consistent and pairwise inconsistent, as is the case for location 44. Where the center location is self-consistent, each nearest-neighbor non-seed location will be either self-consistent and pairwise consistent or self-inconsistent and pairwise inconsistent.

After each nearest-neighbor pair has been scored at a location, the location is classified according to the confidence value, as indicated above. One exemplary classification is as follows: (a) If the location is in complete disagreement with its nearest neighbors, i.e., all pairs have been scored pairwise-inconsistent, then the location is assigned to a "discrepancy" class; (b) If the pairwise self- consistency score is greater than 75% (e.g., at least seven of the eight pairs in a rectangular array FIG. 2 are pairwise consistent), then the locations assign to a "high-confidence" class; and (c) If neither (a) nor (b) apply, assign to a "low-confidence" class.

Figure 6:
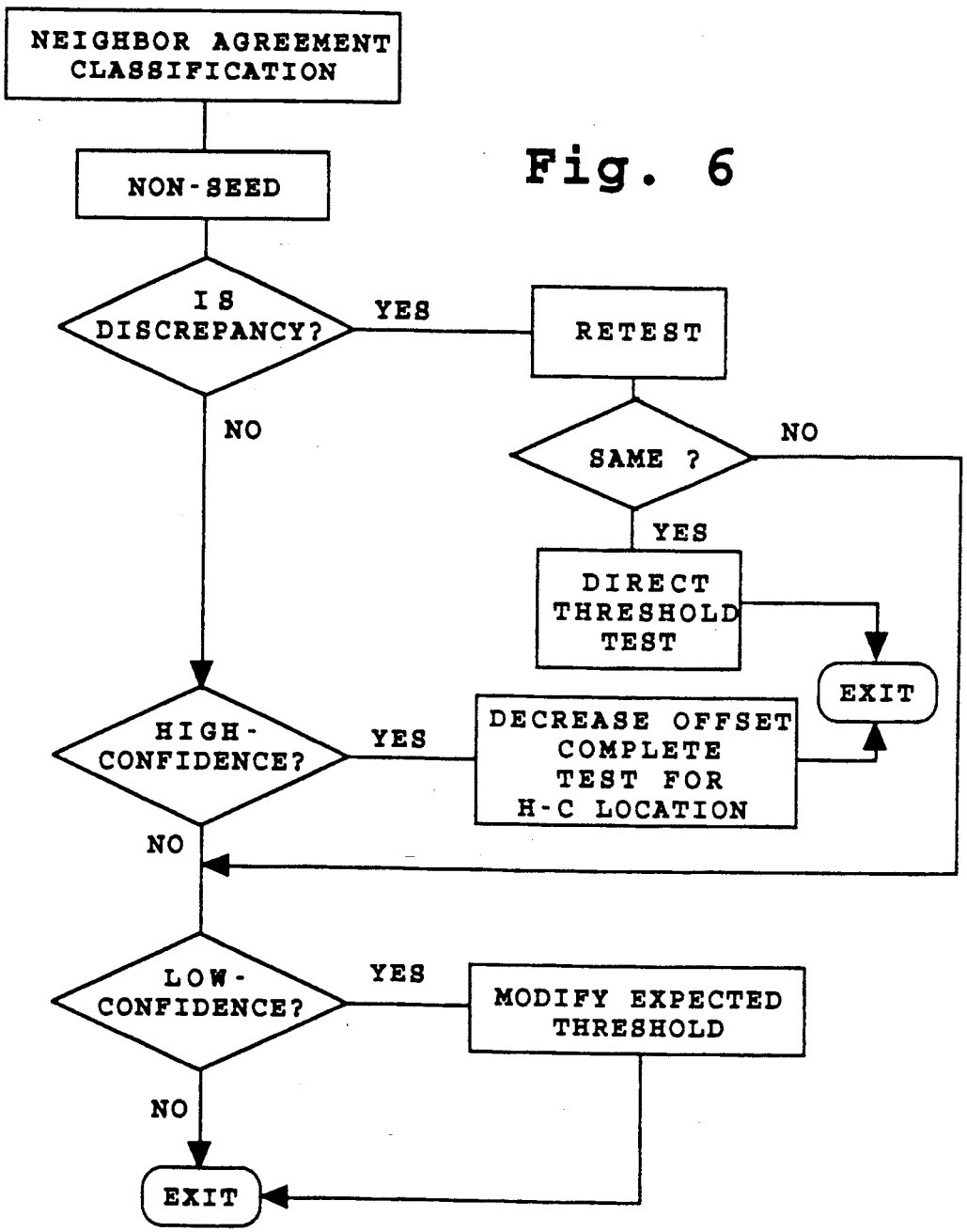
FIG. 6 is a flow diagram of the classification and retest steps in the method of the invention.

Depending on the classification of each location, one of several programmed actions are taken before the next phase of the test, as illustrated in the flow diagram in FIG. 6 ["Heuristics" procedure, pp. 8-9, Appendix A]. If a non-seed location is in a discrepancy class, that location is retested at the original calculated stimulus value, to confirm whether the response at that location was in error. If a different response is obtained, the "expected" threshold at that location is upgraded to correspond with the retested response.

If a non-seed location is in a "low-confidence" class, the expected threshold at that location is adjusted to a new threshold expectation value which is calculated to increase the nearest-neighbor agreement of that location. In one preferred method, the adjustment is made on the basis of position in the visual field and the expected values of neighboring locations, weighted by the confidence limits of those locations. If the location is in a "not-seen" group, the expected threshold is increased halfway between the previous threshold and the maximum stimulus value.

Each non-seed point in the test field has now been assigned a confidence level with respect to neighboring points in the test field, and the expectation value at this location has been adjusted or retested if the original value is below a given confidence level.

6. Refining Confidence Limits

Following the first-phase presentation, in which all of the non-seed locations are tested for agreement with expected values, the test array is retested to improve confidence limits, particularly at locations which are originally scored as in "discrepancy" or "low-confidence" classes. In one preferred embodiment, all of the non-seed locations in the array are retested in a second-phase presentation to (a) refine the expected threshold interval of "high-confidence" locations, and (b) recalculate the confidence limits of non-seed locations which were originally scored as "low-confidence" and therefore have adjusted revised expected threshold values. Selected locations are then retested in a third-phase presentation to refine the confidence limits.

Figure 7:
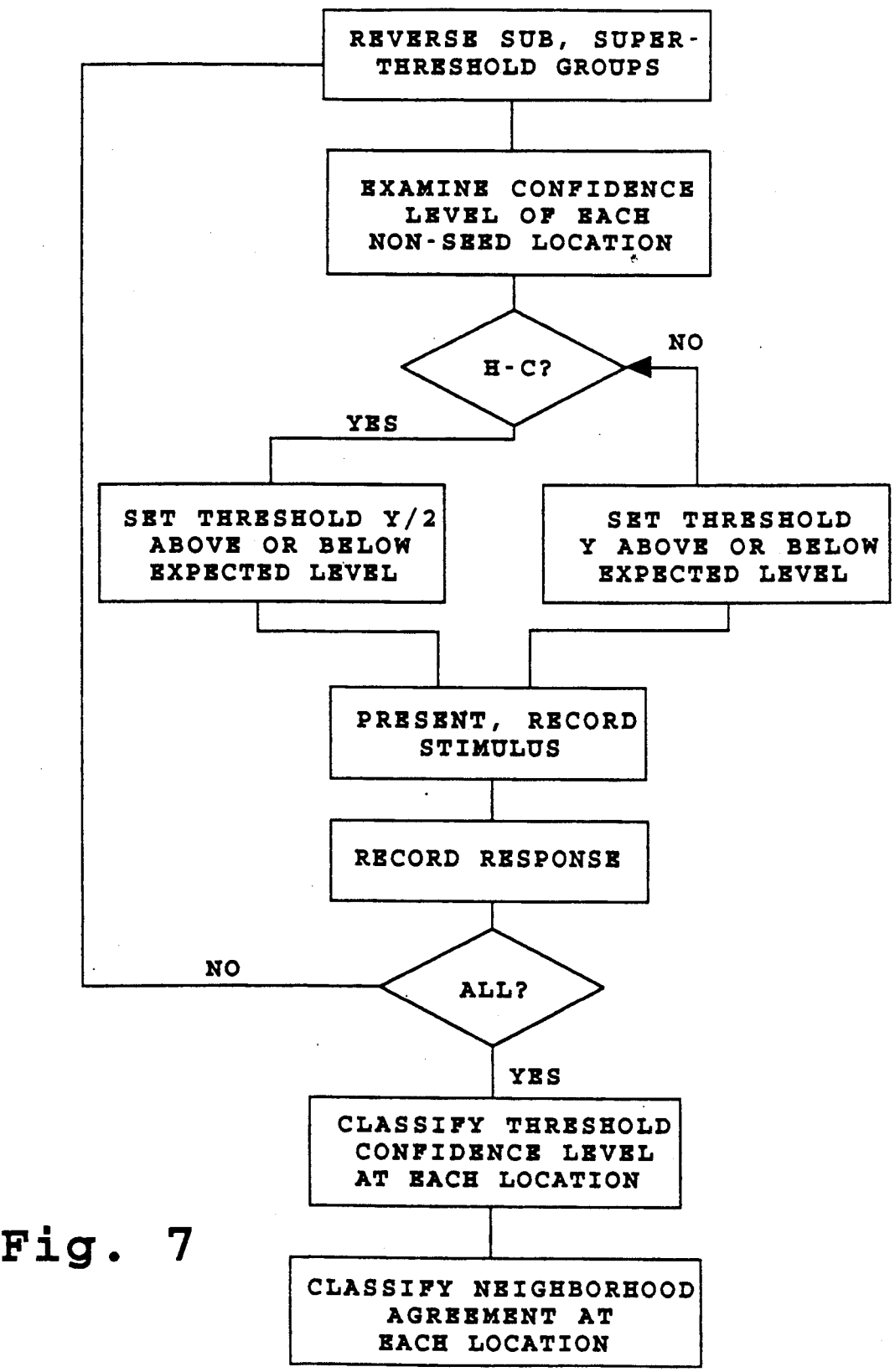
FIG. 7 is a flow diagram of the program control used for evaluating and adjusting recorded response information in a test procedure.

FIG. 7 ["Pass 1 or 2" function, pg. 16, lines 14–53, Appendix A] shows a flow diagram of a second-phase stimulus presentation and analysis. As a first step, the sub- and super-threshold groups of non-seed locations are reversed; that is, a non- seed location originally assigned a to a sub-threshold or super-threshold group is now placed in a super-threshold or sub-threshold group, respectively. At each non-seed location, the confidence level of the location (determined from above) is examined. If the location was originally scored "high-confidence," the level of stimulus presentation above or below the expected threshold is reduced from the selected level Y employed in the first phase, to Y/2. For example, if the first-phase presentation was 2 dB above or below the expected intensity at a non-seed location, the second-phase intensity at "high-confidence" locations is 1 dB above or below expected threshold. If the non-seed location has a lower confidence value, the stimulus presentation level above or below the expected threshold is unchanged from the first- phase presentation. e.g., 2 dB above or below the expected threshold level.

After all of the non-seed locations have been tested, the analysis performed after the first-phase presentation is repeated to determine the confidence level of threshold response at each non-seed location. Here it is noted that the agreement analysis with nearest neighbors can provide an additional high-confidence classification, namely, high-confidence as determined for nearest neighbors which were tested at the refined threshold stimulus values. Any locations which are classed as "low-confidence" with respect to their nearest neighbors are adjusted in expected threshold to a value calculated to produce greater neighbor agreement, as described above.

The second-phase of the test may reveal locations which are in complete disagreement with all nearest neighbors after a second retesting. These locations are assumed to be spatial anomalies, strongly unrelated to nearest neighbors, and are separately tested directly for threshold value, using the method applied to the seed locations to establish their threshold value. These final processing steps are indicated at the bottom in FIG. 7.

Following the stimulus presentation and analysis in the second phase, the expected threshold values in the test field may be refined with a third-phase presentation. Unlike the first- and second-phase presentations, the third phase is concerned only with refining the confidence level of those locations which are in a "low-confidence" class after the second phase; that is, those locations for which an expected threshold adjustment was made after the second phase. All locations in the "high-confidence" class are deemed to be reliable after the second phase.

Figure 8:
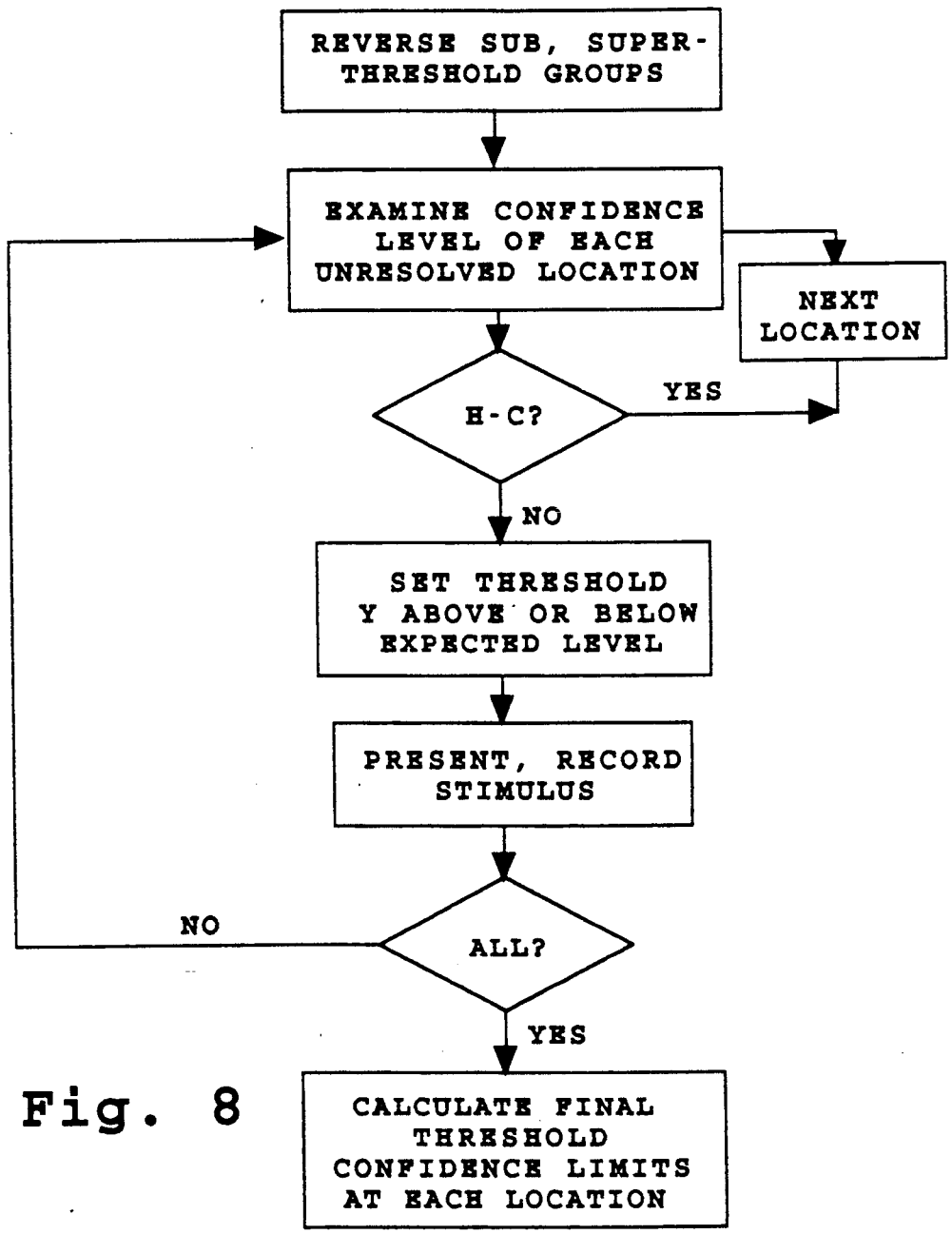
FIG. 8 is a flow diagram of the program control for evaluation and adjusting recorded response information for low confidence locations that remain unresolved at the completion of procedure shown in FIG. 7.

The flow diagram of the third phase of the test procedure is given in FIG. 8 ["Pass" procedure, page 22, line 24, to page 23, line 24, Appendix A]. As indicated, the sub- and super-threshold groups are reversed once more, returning the non-seed locations to their original group assignments. Each non-seed location in a "low-confidence" class is now presented a stimulus at the same level above or below the expected threshold value as used in the first- phase, e.g., 2 dB in intensity level.

After all of the "low-confidence" locations have been tested in the third phase, each location can be assigned a threshold value with defined confidence limits given to every non-seed location. The threshold value is, of course, the originally calculated or adjusted threshold value assigned to each non-seed location. The confidence limit assigned to each non-seed point is determined from (a) the extent of neighborhood agreement and (b) the confidence level of self-consistency for that location and its nearest neighbors, i.e., the selected range above or below expected threshold at which the location and its neighbors were scored as "self-consistent."

The final results are preferably presented as a two dimensional map showing the location, threshold value, and confidence limit given at each point. From this output, the subject's ocular condition related to the tested parameters can be determined.

The test method described above can be easily abbreviated if a lower confidence level for non-seed locations is acceptable, for example, in field testing or for routine screening of younger subjects. In one abbreviated test, a first-phase presentation, carried out as above, is followed by a second-phase test which is designed only to retest and upgrade "low-confidence" non-seed locations until all locations have been classed as "high-confidence" points. This abbreviated method reduces by 25–50% the number of stimulus presentations which are typically made in a visual test.

C. Visual-Test Apparatus

1. Stimulus Presentation

Stimulus presentation in the method may be made by any of a variety of visual-test devices designed for presenting a given type of stimulus over a range of stimulus values, e.g., intensity, color, size, and spatial or temporal frequency. For perimetry testing, where light stimuli are presented at selected locations in a visual field, the device may be a conventional projector or light-diode array type stimulus device.

One preferred type of device for perimetry testing is a Badal-type optical device described in co-owned U.S. patent application for "Perimetry Test Device and Method," Ser. No. 482,278, filed Feb. 20, 1990. Briefly, with respect to FIG. 1, this device includes fixed-position image source 10 for directing a low-intensity light beam 28 at the subject, and movable image source 30 for directing a selected-intensity beam 32 at the subject from any of the locations in the test field. The movable image is a variable-intensity light field. The movable image is a variable intensity light source carried at the end of a two-arm assembly designed to move the light source between any two locations in the test field in a period of about 1-3 sec.

The ocular through which the light images are viewed is provided with diffuse, back-scattered light which serves to mask background and other low-level stray light.

2. Recorder and Control Unit

The subject "seen" responses are recorded in a conventional recorder 20 preferably activated by a hand-held push button, as indicated above, and "Not-seen" responses are recorded after each light stimulus which is not seen by the subject.

Figure 9:
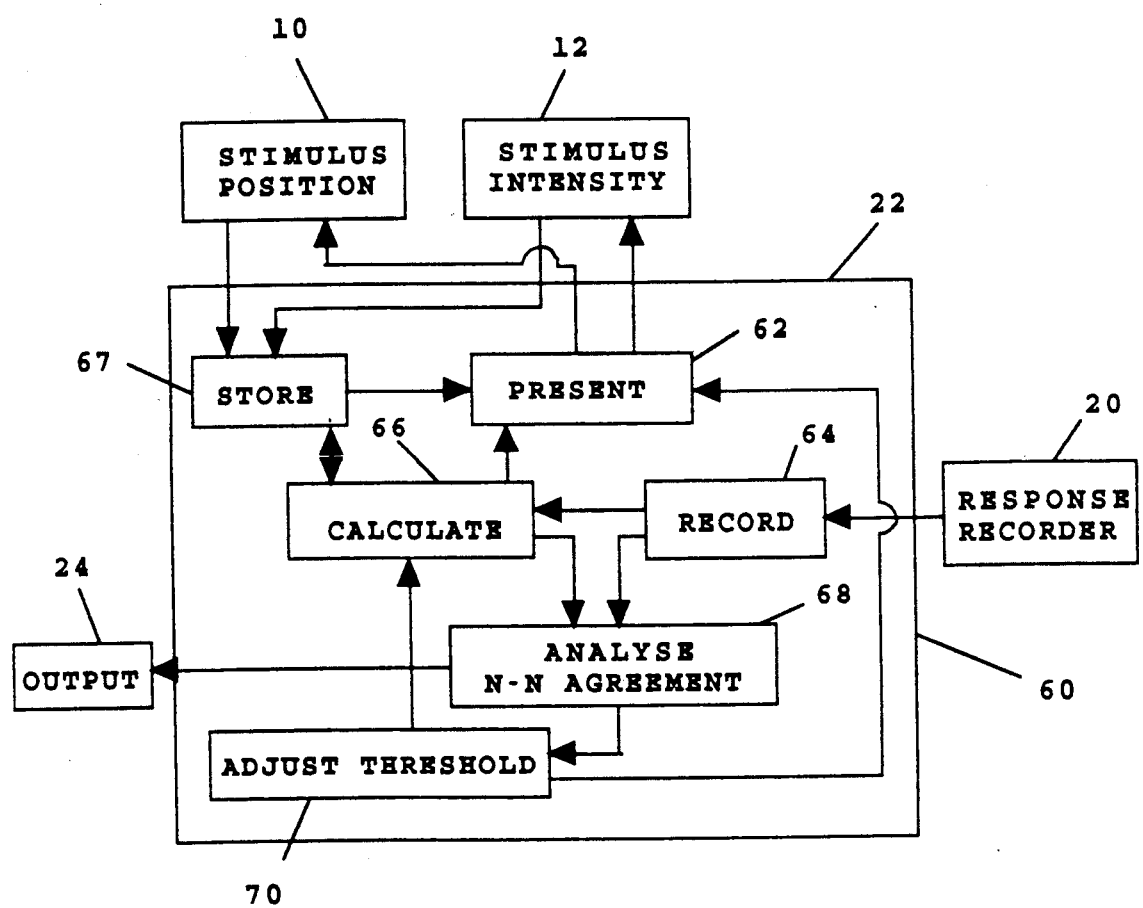
FIG. 9 illustrates the relationship among the various operations carried out by the control unit in the apparatus of the invention.
Figure 10A:
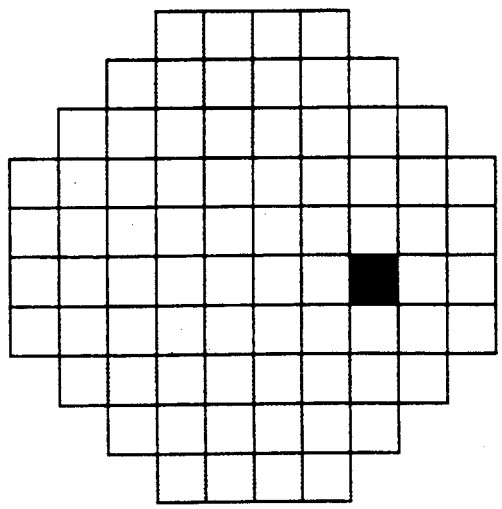
FIGS. 10A-10D show visual field maps of an individual with normal visual field (FIGS. 10A and 10B), and actual threshold values measured (FIGS. 10C and 10D) using a standard 30-2 test strategy (FIGS. 10A and 10C) and the method of the present invention (FIGS. 10B and 10D)
Figure 10B:
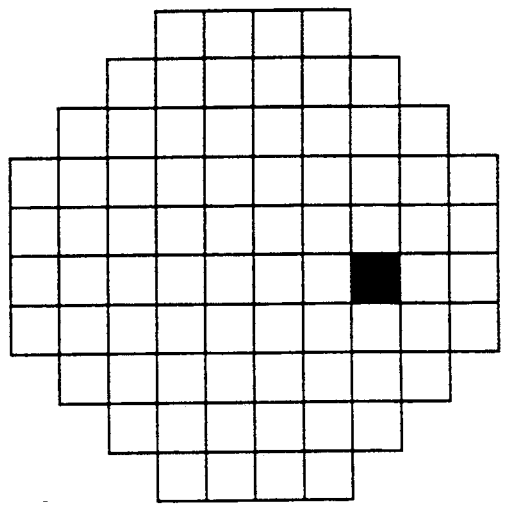
Figure 10E:
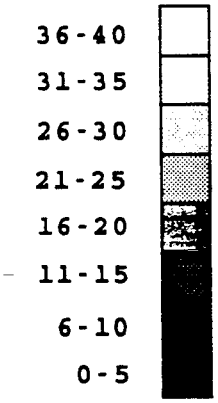
FIG. 10E shows the symbols used in FIGS. 10A and 10B.
Figure 10C:
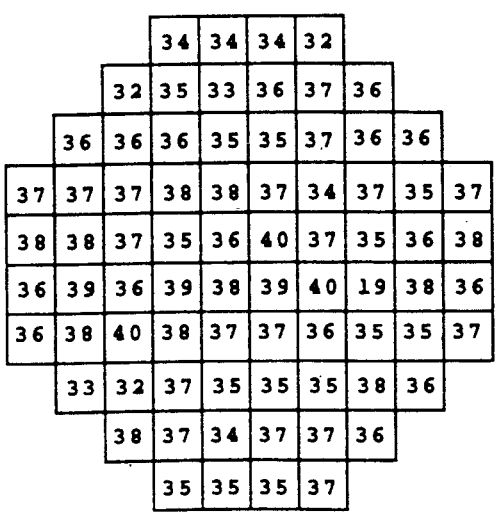
Figure 10D:
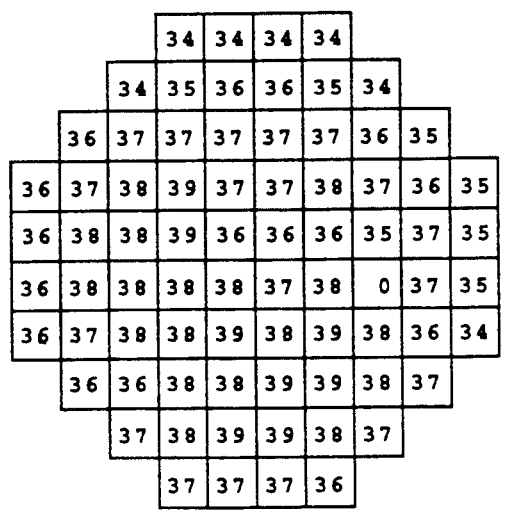

The control unit includes a conventional microprocessor, such as a microcomputer, which receives digitized response signals from recorder 20, performs realtime test-control calculations, and outputs signals to the stimulus presentation device for presentation of selected-level stimuli to the subject at selected locations in the test field. The operations carried out by the control unit 22, and the interaction of the unit with the presentation device, recorder and output display device are shown in FIG. 9 where the microprocessor, and the software employed in the test method are indicated by solid lines 60. The source code of software referred to in the description of the control unit is provided in the Appendices described in Section A.

It will be understood that the functions indicated in FIG. 9 do not necessarily represent separate parts of the program carried out by the software, or separate hardware operations. Rather, they indicate In the initial phase of the test, the control unit operates to (a) select a seed location selection routip. 11 - Get next target, (b) instruct the presentation device to move to the selected location, and (c) instruct the presentation device to present a stimulus of a given level, e.g., given intensity. ("MMOBS" presentation, pp. 9 to 10, Appendix A). These operations are embodied in a "present" algorithm indicated at 62.

The subject response to the seed-location stimulus is supplied to the program through a record function 64, and the stored value is passed to a "calculate" function 66 to determine (a) the current upper or lower bound and (b) the level of the next stimulus at the seed location. This information is supplied through the "present" function to the presentation device. These steps are repeated until the threshold range at that seed location has been determined, according to the algorithm outlined in FIG. 3. The control unit then advances the presentation device to the next seed point for threshold determination. The process is repeated until all seed points have been tested ("Resolve" comands in MMOBS"presentation at pg. 11, Appendix A).

Figure 4:
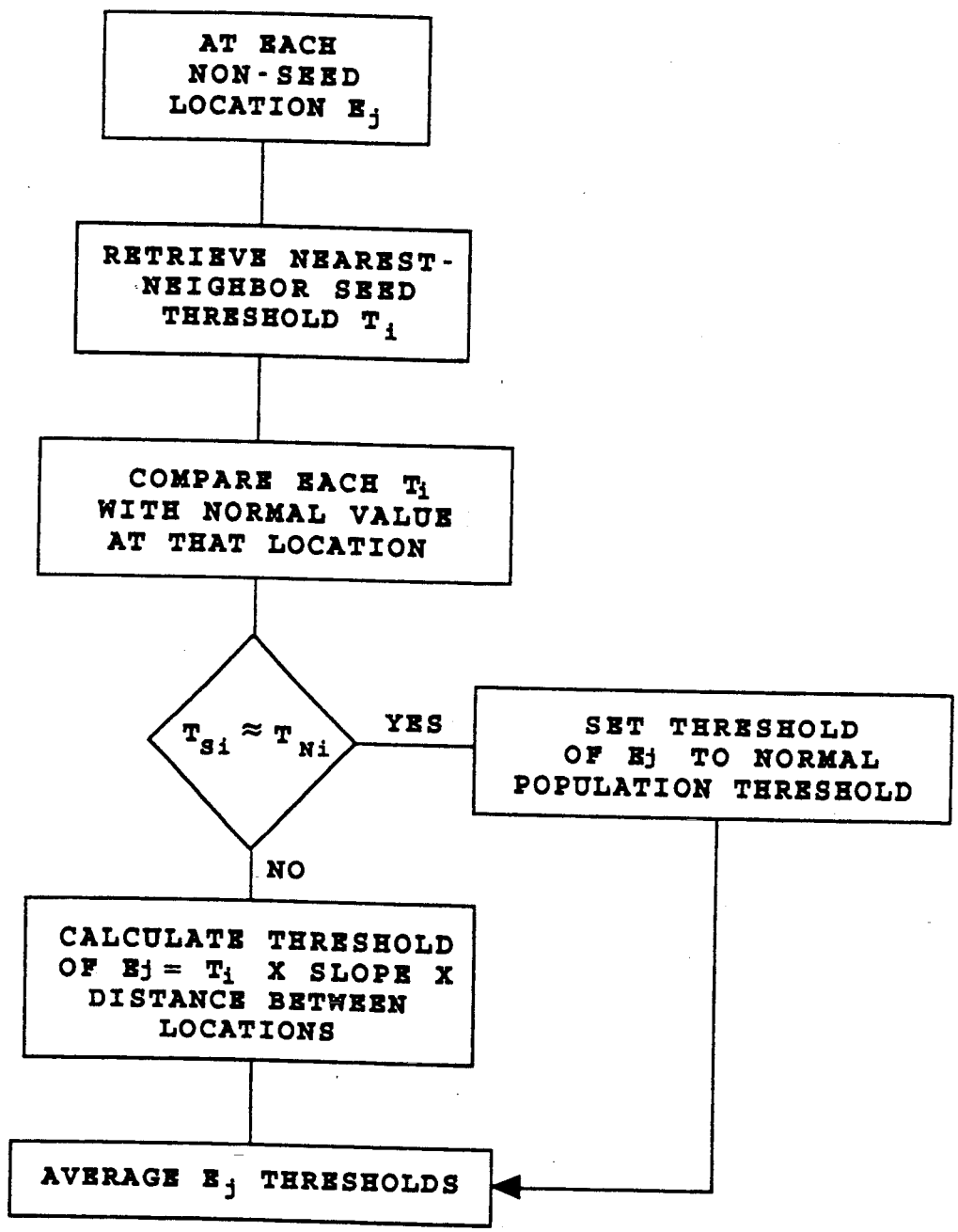
FIG. 4 is a flow diagram of steps for calculating the expected threshold values of non-seed locations.

"Calculate" function 66 in the control unit also uses the seed-location values to calculate expected threshold values, and corresponding sub- and super-threshold values, at each of the non-seed locations, employing the algorithm outlined in FIG. 4 and given on pages 11 to 12 of "Open Neighbors," Appendix A. These values are stored in the "store" function 67 until used by the "present" function to present the selected sub- or super-threshold value at the associated non-seed location.

The responses to the non-seed stimulus presentations are recorded, stored and passed to an "analyze" function 68, as indicated, for neighborhood agreement analysis ("Average-Neighbor-xpectation," pp. 7 and 8, Appendix A). The analysis algorithm calculates the confidence limit of each location in the test field and classifies the location on the basis of the confidence value, as described above.

Depending on the classification, the location may be retested (for a discrepancy-class), or adjusted in threshold value (for a "low-confidence" value), according to the algorithm given in the "Heuristics" function on pp. 8 and 9 of Appendix A. The "threshold adjust" function is shown at 70 in FIG. 9.

The control unit continues the test procedure until desired confidence limits are reached, as described. The results, presented in terms of thresholds and confidence limits at the locations in the field are displayed at the output. Program steps for carrying out the retest and second- and third-phase of the test method are given on pages 14 to 27 of the Appendix A.

The final threshold values calculated for the locations in the visual field are plotted at output 24 in a suitable form, such as the visual field maps shown in FIGS. 10 and 11.

D. Test Results

Quantitative automated static perimeters known in the prior art use rapid staircase procedures to measure visual field sensitivity. Previous studies (both computer simulations and clinical evaluations of patients) indicate that the accuracy and efficiency of these staircase procedures are at nearly optimal expected levels of performance.

Extensive computer simulation comparisons of the method of the invention, as applied to perimetry, with standard staircase perimetry testing methods (Humphrey Analyser 30-2 Full Threshold Test). The results show that the present invention is significantly more efficient, typically requiring one-third to one-half or more fewer presentations to complete testing. The present method also has more consistent test times. Normal individuals and patients with visual field loss are all tested in 230-275 presentations, over a total test time of 6-8 minutes. By contrast, the standard staircase presentation typically requires between about 350-500 presentations for normal individuals and between about 500-900 presentations for patients with moderate-severe visual field impairment, as seen below, with test times ranging from 12-27 minutes.

In addition, the method of the invention was found to have slightly better accuracy and test reliability, and is less susceptible to the influence of fatigue and boredom, due to the fewer test presentations.

FIGS. 10A-10D compare visual field tests performed 10 A and 10C) and the present method (FIGS. 10B and 10D) on an individual with normal visual field. The total number of presentations in the 30-2 test was 369, and in the perimetry method of the invention, 231. The threshold values determined by each test are shown at the bottom of the figure. The average difference between the locations measured in the two test was 0.51 dB. The corresponding visual field maps, expressed in 5-dB increments (FIG. 10E) are given at the top in the figure.

Figure 11A:
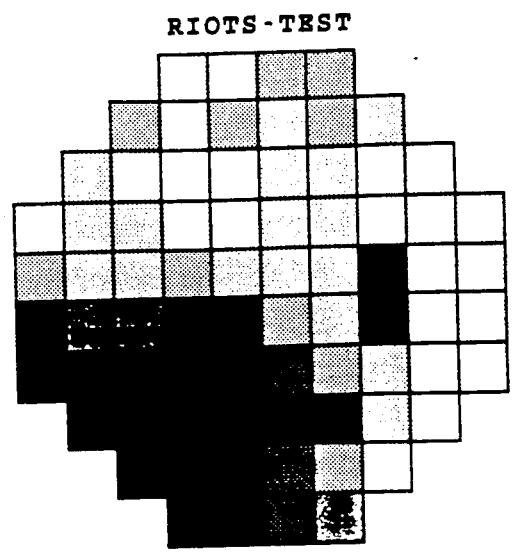
FIGS. 11A-11C show visual field maps of an individual with moderate-severe glaucoma measured by perimetry testing by the method of the present invention (FIG. 11A), upon retest by the method of the invention one week after the first test (FIG. 11B), and by a standard 30-2 test stra-tegy (FIG. 11C)
Figure 11B:
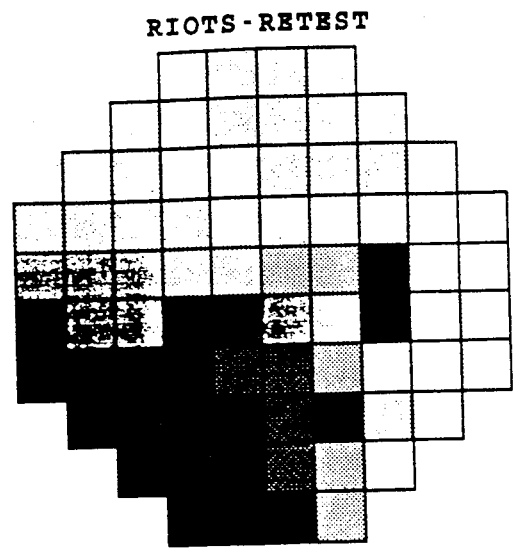
Figure 11C:
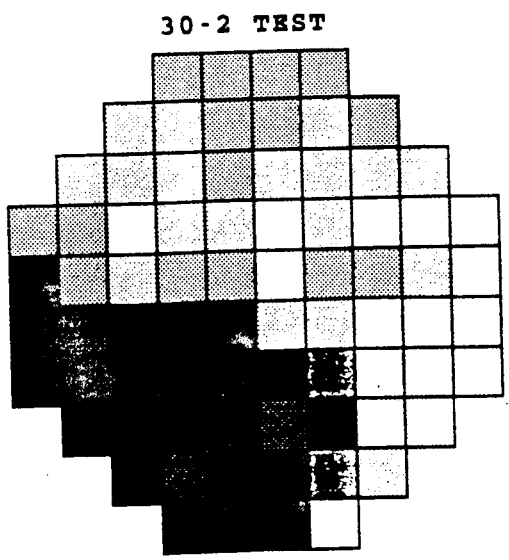
Figure 11D:
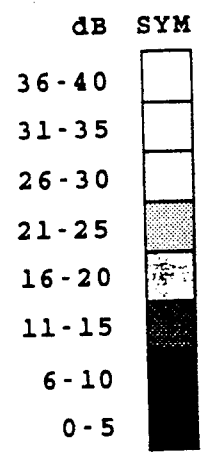
FIG. 11D shows the symbols used in FIGS. 11A-11C.

FIGS. 11A-11C show a similar test comparison preformed on a patient with moderate to severe glaucoma. FIG. 11A is the visual field map generated in a test with 237 presentations, in accordance with the present invention. The map show severe loss of visual field in the lower left quadrant (inferior nasal) of the visual field and moderate loss in the other three quadrants. The patient was retested one week later with the same method, using 256 test presentations, with the results shown at the right in FIG. 11B. A comparison of the visual fields in FIGS. 11A and 11B shows the degree of test consistency which is achieved.

The same patient was tested by the 30-2 standard staircase method, requiring a total of 591 presentations, i.e., more than twice the number of presentations required in the present method. The visual field map generated by the 30-2 test is shown in FIG. 11C. The average difference between the first test (FIGS. 11A) and the 30-2 test was 1.49 dB, and between the second test (FIG. 11B) and the 30-2 test, 1.82 dB.

The advantages in test efficiency can be readily appreciated from the clinical tests above. As discussed, the greater efficiency is achieved, in part, by updating threshold and confidence values assigned to each point during the test, i.e., in real time, to optimize the presentation of additional stimuli. The method also provides a means of immediate real-time detection and correction of response errors as the test is being performed.

Although the invention has been described with reference to particular embodiments and test procedures, it will be apparent that various changes and modifications can be made without departing from the invention.

APPENDIX A

```
interface
uses TPDos,TPcrt,graph,Globals,simparam,HC30_2,min_max,
     plotpak,ustatic,respn,printer,pause;

procedure heuristic_static_RIOTS;

implementation procedure heuristic_static_RIOTS;

{
A heuristic stratagy for static perimetry

RRRR  IIIII  0000  TTTTT  SSSS    Real-time
     R  R    I    0  0    T    S       Interactive
     RRRR    I    0  0    T    SSSS    Optimized
     R  R    I    0  0    T       S    Test
     R  R  IIIII  0000    T    SSSS    Sequence Note: see HUMCEN30.PAS for global constant NEIGHBORS for the
Central 30 - 2 pattern.

} const

{
      Note: given the CENTRAL 30-2 test pattern (only) the 'Red_squares'
      are every other target location. The values of 'Red_squares' are the
      ELEMENT indicies which are used in accessing the WORKSHEET.
   }
     Red_squares : set of 1..76 = [38,69,54,14,61,66,30,41,49,74,46,6,25,33,
                                   58,22,1,9,17,19,11,3,24,60,35,27,8,48,76,
                                   51,43,32,68,63,16,56,71,40];
     nlocX : array[1..8] of integer = (-8,0,8,-8,8,-8,0,8);
```

```
    nlocY : array[1..8] of integer = (-8,-8,-8,0,0,8,8,8);
    RIOTS_suprathreshold_offset = -6;

type
    imatrix_type = array[0..6,0..6] of integer;
    aggree_type  = record
                      imatrix : imatrix_type;
                      pass    : integer;
                      fname   : string[6];
                   end;

var
    decision : possible_responses;
    element,
    pass,
    color,
    temp_cx,temp_cy,
    lx,ly,
    n,i,j,
    cflag,              { center point seen flag }
    sflag,              { neighbor seen flag }
    NSame,              { index for percentage values }
    NDiff,
    nenSame,            { non-empty neighbor count }
    nenDiff   : integer;
    rx,ry,
    WSame,              { cum weightings for a neighborhood }
    WDiff,
    temp_scale_view : real;
    offset_str : string[3];
    done,
    needs_header : boolean;
    aggree_info : aggree_type;
    aggree_file : file of aggree_type;
    IMatrix : imatrix_type; { agreement freq matrix }

{
    mobs_borders : array[1..76] of record
                                      lower,
                                      upper : stack;
                                   end;
}
    tempfile : text;

procedure push (x : integer; var s : stack);
begin
    Inc(s.cur);
    s.v[s.cur] := x;
end;

procedure pop (var s : stack);
begin
    if s.cur > 1 then
       Dec(s.cur);
end;
```

```
  function peek (s : stack) : integer;
  begin
    if s.cur > 0 then
      peek := s.v[s.cur]
    else
      writeln('*** ERROR *** trying to peek an empty stack!');
  end;

procedure write_stack (s : stack);
    var i : integer;
  begin
   for i := s.cur downto 1 do
     write(s.v[i]:3);
end;

procedure Mobs (     element,
                  default_low,
                  default_high,
                  exit_criteria,
                  criterion_reversals : integer;
              var low_border,
                  high_border : stack;
              var threshold : integer);

const
    seen : boolean = true;

var
    range,
    t,i,j : integer;
    resp,
    response_error,
    last_resp : boolean;
    p : array[1..25] of integer;
    history : array[1..25] of histrec;
    save_element : integer;

begin { MOBS main } worksheet[element].MOBSed := true;
  save_element := next_element;
  next_element := element;

range := default_high - default_low + 1;
  low_border.cur := 0;
  high_border.cur := 0;

{ absolute limits of system }
  push(lower_limit,low_border);
  push(upper_limit,high_border);

{ calculated limits }
  push(default_low,low_border);
  push(default_high,high_border);
```

```
resp := false;
last_resp := false;
response_error := false;

t := 0; { trial counter }

{ calculate initial stimulus level }
{ ================================================================ }
{ mobsification#2 (7/13/88) - Skew first presentation: 2/3 toward one end }
  p[1] := default_low + round(range * range_fraction);

{ ================================================================ }

{ trial loop... }
 repeat
   Inc(t);

{ get response here... }
   last_resp := resp;
   worksheet[element].luminance := p[t];
   Inc(worksheet[element].presentation);
   Inc(total_presentations);
   resp := (respond(worksheet[element]) = target_seen);

response_error := response_error or (FA_flaged or MISS_flaged);
   with history[t],worksheet[element] do
     begin
       lum := luminance;
       sens := sensitivity + variation_in_sensitivity;
       if resp then respn := 1 else respn := 0;
       error := 0;
       if FA_flaged then error := 1;
       if MISS_flaged then error := 2;
     end;

{ display response... }
   if not batch then
     begin with worksheet[element] do
       if not resp then
         dynamic_plot(radius,meridian,luminance+inverted)
       else
         dynamic_plot(radius,meridian,luminance);
       stat_display(worksheet[element]);
       GotoXY(45,16);Write('':34);
       GotoXY(45,17);Write('':34);
       Textcolor(yellow);GotoXY(45,16);Write_stack(high_border);
       Textcolor(lightblue);GotoXY(45,17);Write_stack(low_border);
     end;

if keypressed then respond_to_keyboard; { check for abort or step }
   single_step_check;

{ test for subject response }
    if resp = seen then
      push(p[t],low_border)
    else
```

```
      push(p[t],high_border);

{ test for crossing borders }
    if peek(low_border) >= peek(high_border) then
      begin
        { problem with borders... }
         if resp = seen then
           pop(high_border)
         else
           pop(low_border);
         p[t+1] := trunc((peek(low_border)+peek(high_border))/2.0);
      end
    else
      begin { borders are OK... }
        { check for a reversal after 2nd response }
         if (t>1) and (resp <> last_resp) then Inc(worksheet[element].reversals);
        { set new expected value - next stimulus value }
         if (t>1) and (resp = last_resp) then
           if resp = seen then
             p[t+1] := peek(high_border)
           else
             p[t+1] := peek(low_border)
         else
           p[t+1] := trunc((peek(low_border)+peek(high_border))/2.0);
      end;

until ((worksheet[element].reversals >= criterion_reversals)

{ ============================================================ }
{ mobsification#3 (7/13/88) - Constrain exit when within +/-
                          2*exit_criteria dB range } and
       ((peek(high_border)-peek(low_border)) <= 2*exit_criteria))

{ ============================================================ }
{ added 11/11/88 - handles range limits of device              }
{ removed 12/19/88
       or ((resp=last_resp)
           and (((resp=seen)and(worksheet[element].history[t].lum=upper_limit))
               or
               ((not(resp=seen))and(worksheet[element].history[t].lum=lower_limit))
               ))
}
  { ============================================================ } or escaped;

threshold := trunc((peek(low_border)+peek(high_border))/2.0);

if mobs_print
{
      and
    response_error
}
      and
```

```
          (abs(worksheet[element].sensitivity-threshold) > 10)
then
  begin { output history to printer }
    Writeln(tempfile,chr(27)+'&k4S');
      writeln(tempfile,'>10dB error found for mMOBS.    | Actual sensitivity for target #',element:0,' is ',
              worksheet[element].sensitivity:0);
      writeln(tempfile,'                                |',
                worksheet[element].sensitivity:0,' - ',threshold:0,' = ',
                worksheet[element].sensitivity-threshold:0,' [dB Error] ');
      Writeln(tempfile,'Response Pattern: [1-seen, 0-not seen]');
      Writeln(tempfile,'Target dB 1     1     2     2     3     3     4     4     5');
      Write   (tempfile,'0----5----0----5----0----5----0----5----0----5----0');
      Writeln(tempfile,'      t :   lum   sen  (response error)');
      for i := 1 to t do
        with history[i] do
          begin
            if lum > 0 then
              for j := 0 to lum-1 do
                if j = worksheet[element].sensitivity then write(tempfile,'|') else write(tempfile,' ');
            if respn = 1 then write(tempfile,'1') else write(tempfile,'0');
            for j := lum+1 to 55 do
              if j = worksheet[element].sensitivity then write(tempfile,'|') else write(tempfile,' ');
            write(tempfile,i:3,' : ',lum:5,sens:5);
            case error of
              0: writeln(tempfile,'    ');
              1: writeln(tempfile,'  FA');
              2: writeln(tempfile,' MISS');
            end;
          end;
      Write(tempfile,chr(27)+'&k0S');
      writeln(tempfile,'-----');
    end;

next_element := save_element;
end; { MOBS } function same(a,b:integer):boolean;
{ returns TRUE if a and b (indices to worksheet) are of the same
  type (red or black squares) }
begin
  same := ((a in Red_squares) and (b in Red_squares))
          or
          (not(a in Red_squares) and not(b in Red_squares));
end;

function gen_index(x:integer):integer;
{ returns the index value of the given percentage }
begin
  case x of
     0 : gen_index := 6;
    25 : gen_index := 5;
    33 : gen_index := 4;
    50 : gen_index := 3;
    66 : gen_index := 2;
```

```
      75 : gen_index := 1;
     100 : gen_index := 0;
    end;
end;
function inv_gen_index(x:integer):real;
begin
  case x of
     6 : inv_gen_index := 0.0;
     5 : inv_gen_index := 0.25;
     4 : inv_gen_index := 0.333;
     3 : inv_gen_index := 0.50;
     2 : inv_gen_index := 0.666;
     1 : inv_gen_index := 0.75;
     0 : inv_gen_index := 1.0;
  end;
end;

procedure Pattern_Highlight(lx,ly,color:integer);
begin
  if not batch then
    begin
      SetColor(color);
      SetFillStyle(SolidFill,color);
      Bar(lx-22,ly-13,lx+12,ly+12);
    end;
end;

function Possible_FA (seen:boolean) : boolean;
begin
  Possible_FA := seen and (NSame >= Dissagree_limit)
                      and (NDiff >= Dissagree_limit);
end;

function Possible_Miss (seen:boolean) : boolean;
begin
  Possible_Miss := (not seen) and (NSame >= Dissagree_limit)
                             and (NDiff >= Dissagree_limit);
end;

function average_neighbors_expectation(center:integer):integer;
  const
    slope   : real    = -0.30;  { dB/deg }
  var
    i,
    neighbor,
    center_exp,
    center_rad : integer;
    num,
    weight,
    cum,
    neighbor_expected : real;
```

```
begin
  center_rad := worksheet[center].radius;
  cum := 0.0;
  num := 0.0;
  for i := 1 to 8 do
    begin
      neighbor := neighbors[center,i];
      if not ((neighbor = xx) or (neighbor in BS_points)) then
        with worksheet[neighbor] do
          begin
            if MOBSed then
              weight := 1.0
            else with history[numhist] do
              weight := (inv_gen_index(ns) + inv_gen_index(nd)) / 2.0;
            { note: in the following calculation, threshold[numreps] represents
                    the most recent guess at a threshold for the given neighbor }
            neighbor_expected := threshold[numreps] - slope * (radius - center_rad);
            cum := cum + weight * neighbor_expected;
            num := num + weight;
          end;
    end;

average_neighbors_expectation := round(cum / num);
end;

procedure Heuristics; { Revision # 5.0 }
{
Manipulates expected threshold and offset values based upon current
state of affairs.
Called by Pass1 and Pass2 procedures.
}
  var
    NSame, Prev_NSame,
    NDiff, Prev_NDiff,
    i,j : integer;

begin
  for i := 1 to 76 do
    begin
      with worksheet[i] do
        begin
          NSame := history[numhist].ns;
          NDiff := history[numhist].nd;
          if Pass > 1 then { find previous agreement scores }
            begin
              j := numhist;
              while (j>=1)and(history[j].lum=history[numhist].lum) do Dec(j);
              if j>=1 then
                begin
                  Prev_NSame := history[j].ns;
                  Prev_NDiff := history[j].nd;
                end;
            end;
          { update expected value for threshold }
          threshold[pass] := threshold[pass-1];
```

```
                threshold[pass+1] := 0;
            if not MOBSed then
                    begin
                        if (NSame <= 1) and (NDiff <= 1) then { good agreement }
                          begin
                            next_step := next_step div 2;
                            if next_step < 2 then next_step := 2;
                          end
                        else
                          { ** need to adjust expected threshold ** }
                            if (NSame = 6) and (NDiff = 6) then { poor agreement }
                              if seen[pass] then
                                Mobs(i,luminance,upper_limit,
                                     exit_criteria,criterion_reversals,
                                     low_border,high_border,threshold[pass])
                              else
                                Mobs(i,lower_limit,luminance,
                                     exit_criteria,criterion_reversals,
                                     low_border,high_border,threshold[pass])
                            else  { midlin agreement }
                              if seen[pass] then
                                threshold[pass] := average_neighbors_expectation(i)
                              else if Pass > 1 then
                                if Seen[pass-1] then { bracketed response }
                                  threshold[pass] := average_neighbors_expectation(i)
                                else { need stronger stimuli & third pass }
                                  begin
                                    threshold[pass] := (threshold[pass-1]+lower_limit) div 2;
                                    threshold[pass+1] := -1;
                                  end;
                            threshold[pass] := max(threshold[pass],lower_limit);
                            threshold[pass] := min(threshold[pass],upper_limit);
                      end;
                    numreps := pass;
                    Inc(IMatrix[NSame,NDiff]);
                end;
{       if pass = 2 then updatePatMat(i);}
        end;
    end;

procedure mMOBS_presentation(var current_stimulus : mod_rec);
  const
    was_seen : boolean = true;

var
    t : integer;
    response_error,
    resp,
    last_resp : boolean;

begin
  with current_stimulus do
    begin
      Inc(total_presentations);
      Inc(presentation);
```

```
  t := presentation;

{ get response here... }
  last_resp := (history[t-1].respn=1);

{ get response here... }
  luminance := history[t].lum;
  resp := (respond(worksheet[element]) = target_seen);
  if not batch then dynamic_plot(radius,meridian,luminance+inverted);

response_error := response_error or (FA_flaged or MISS_flaged);
  with history[t] do
    begin
      lum := luminance;
      sens := MIN(
                MAX(sensitivity + variation_in_sensitivity,LOWER_LIMIT),
                UPPER_LIMIT);
      if resp then respn := 1 else respn := 0;
      error := 0;
      if FA_flaged then error := 1;
      if MISS_flaged then error := 2;
    end;

{ display response... }
  if not batch then
    begin
      follow_show;
      stat_display(worksheet[element]);
      GotoXY(45,20);Write('':34);
      GotoXY(45,21);Write('':34);
      Textcolor(yellow);GotoXY(45,20);Write_stack(high_border);
      Textcolor(lightblue);GotoXY(45,21);Write_stack(low_border);
    end;
  single_step_check;

{ test for subject response }
  if resp = was_seen then
    push(history[t].lum,low_border)
  else
    push(history[t].lum,high_border);

{ test for crossing borders }
  if peek(low_border) >= peek(high_border) then
    begin
      { problem with borders... }
      if resp = was_seen then
        pop(high_border)
      else
        pop(low_border);
      history[t+1].lum := trunc((peek(low_border)
                              +peek(high_border))/2.0);
    end
  else
    begin { borders are OK... }
      { check for a reversal after 2nd response }
```

```
            if resp <> last_resp then Inc(reversals);
          { set new expected value - next stimulus value }
            if resp = last_resp then
              if resp = was_seen then
                history[t+1].lum := peek(high_border)
              else
                history[t+1].lum := peek(low_border)
            else
              history[t+1].lum := trunc((peek(low_border)
                                        +peek(high_border))/2.0);
        end;

Resolved := Resolved
           or
           ( ((history[t].lum = upper_limit) and
              (history[t-1].lum = upper_limit))
            or
             ((history[t].lum = lower_limit) and
              (history[t-1].lum = lower_limit)) )
           or
            ((reversals >= criterion_reversals)
             and
             ((peek(high_border)-peek(low_border)) <= 2*exit_criteria));
    end;
end; { mMOBS } procedure Pass0;
 { determine seed expectation values, via mMOBS, to be used in Pass1 }
  var
    i,
    range_lower_limit,
    range_upper_limit : integer;
    print_out_mobs_histories : boolean;

procedure get_next_target (var e:integer);
  begin
    if not done then
      repeat
        e := trunc(random(sample_size)+1);
      until worksheet[e].open
            and
            not(worksheet[e].Resolved)
            and
            (e in Seed_Points+BS_Points)
    else
      e := 1;
  end;

procedure open_neighbors(center:integer);
    const
      slope   : real    = -0.30;  { dB/deg }
    var
      i          : integer;
      neighbor   : integer;
      expected   : integer;
```

```
        expected_rad : integer;
        neighbor_expected : real;
        normal_expectation : boolean;
    begin
      with worksheet[center] do
        begin
          expected := threshold[pass];
          expected_rad := radius;
          normal_expectation := normal = expected;
        end;
      for i := 1 to 8 do
        begin
          neighbor := neighbors[center,i];
          if not ((neighbor = xx) or (neighbor in BS_points)) then
            with worksheet[neighbor] do
              begin
                if not normal_expectation then
                  neighbor_expected := expected
                                  + slope * (radius - expected_rad)
                else
                  neighbor_expected := normal;
                if threshold[pass] = 0 then { fresh expectations }
                  threshold[pass] := round(neighbor_expected)
                else { take average of old and new expectations }
                  threshold[pass] := (threshold[pass]
                                  + round(neighbor_expected)) div 2;
                threshold[pass] := max(threshold[pass],lower_limit);
                threshold[pass] := min(threshold[pass],upper_limit);
                if not batch then
                  dynamic_plot(radius,meridian,threshold[pass]);
              end;
        end;
    end;

begin print_out_mobs_histories := false;
  static_banners;

done := false;
  get_next_target(next_element);

repeat element := next_element;
    get_next_target(next_element);

with worksheet[element] do
      begin
        Inc(numhist);
        i := numhist;
        case i of { trial presentation }

1 : begin { mobsification#1 (7/12/88) - pretest to limit range }
                range_lower_limit := lower_limit;
```

```
            range_upper_limit := upper_limit;
            if element in Seed_Points then
               luminance := normal + RIOTS_suprathreshold_offset
            else { this location is a Blind spot potential }
               luminance := 15; { II/4E equivalent }
            seen[1] := respond(worksheet[element])=target_seen;
            Inc(presentation); Inc(total_presentations);
            history[presentation].lum := luminance;
         end;

2 : begin
         if seen[1] and (element in Seed_Points) then
            begin
               range_lower_limit := luminance;
               luminance := normal;
               seen[2] := respond(worksheet[element])=target_seen;
               Inc(presentation); Inc(total_presentations);
               history[presentation].lum := luminance;
               if seen[2] then
                  range_lower_limit := luminance;
            end;
         if not seen[1] then
            range_upper_limit := luminance;

range := range_upper_limit - range_lower_limit + 1;
         low_border.cur := 0;
         high_border.cur := 0;

{ absolute limits of system }
         push(lower_limit,low_border);
         push(upper_limit,high_border);

{ calculated limits }
         push(range_lower_limit,low_border);
         push(range_upper_limit,high_border);

history[presentation+1].lum := range_lower_limit
                                    + round(range * range_fraction);

end;

3..max_history
      : begin { mMobs it }
         mMOBS_presentation(worksheet[element]);
         if Resolved and (element in Seed_Points) then
            begin
               threshold[pass] := trunc((peek(low_border)
                                     +peek(high_border))/2.0);
               open_neighbors(element);
            end;
         MOBSed := Resolved;
      end;
end; {case} if not batch then dynamic_plot(radius,meridian,
```

```
                                    history[presentation].lum);
      end;

done := true;
    for i := 1 to number_of_targets do
      if i in Seed_Points + BS_Points then
        done := done and worksheet[i].Resolved;

until done or escaped;

if not batch then
    begin
      GotoXY(45,16);Write('':34);
      GotoXY(45,17);Write('':34);
    end;

if Mobs_print then
    begin
      Write(LST,chr(27)+'&k4S');
      write(lst,filman:6,' :');
      for i := 1 to 76 do
        if i in Seed_Points then
          with worksheet[i] do
            write(lst,sensitivity-threshold[pass]:5);
      write(lst,' : ');
      for i := 1 to 76 do
        if i in BS_points then
          with worksheet[i] do write(lst,sensitivity-threshold[pass]:5);
      write(lst,' : ',total_presentations:3);
      Writeln(LST,chr(27)+'&k0S');
      writeln(tempfile);
      reset(tempfile);
      while not(eof(tempfile)) do
        begin
          read(tempfile,ch);
          write(lst,ch);
        end;
      close(tempfile);
    end;

end;

procedure Pass1or2;

{ assumes that latest expected value is in worksheet[i].threshold[pass-1] } var
    ISame,
    IDiff,
    sumSame,
    sumDiff,
    offset,
    starting_presentation,
    lum,
```

```
     i,
     ni,
     num_retested,
     passpres : integer;
     numpres : array [1..76] of byte;  { number of presentations per element this pass }
     retest : boolean;

procedure get_next_target (var e:integer);
     var
        done_prepass : boolean;
        i            : integer;
  begin
    if (Passpres mod sample_size) <> 0 then
      begin
        done_prepass := true;
        for i := 1 to sample_size do
          if worksheet[i].Mobsed then
            done_prepass := done_prepass
                          and (numpres[i] > (Passpres div sample_size));
        if not done_prepass then
          repeat
            e := trunc(random(sample_size)+1);
          until (numpres[e] <= (Passpres div sample_size))
                and worksheet[e].Mobsed
        else
          repeat
            e := trunc(random(sample_size)+1);
          until numpres[e] <= (Passpres div sample_size)
      end
    else
      e := 1;
  end;

begin starting_presentation := total_presentations;

{ clear out agreement matrix }
  for ISame := 0 to 6 do
    for IDiff := 0 to 6 do
      IMatrix[ISame,IDiff] := 0;

passpres := 0;
  for i := 1 to 76 do numpres[i] := 0;

if not batch then
    begin
      GotoXY(49,13);
      Write('Pass',Pass:2);
    end;

get_next_target(next_element);
  repeat if keypressed then respond_to_keyboard; { check for abort or step }
```

```
if not batch then single_step_check;

RT_variation := initial_RT_variation;

{
  Choose a random target location without replacement for each pass!
}
element := next_element;
get_next_target(next_element);

numpres[element] := numpres[element] + 1;
Inc(Passpres);
num_retested := 0;

with worksheet[element] do
  begin
    { keep track of color for analysis }
    if element in Red_squares then color_square := 0 else color_square := 1;
    seen[pass+1] := true;

if ((element in Red_squares)and(Pass=1))
       or
         (not(element in Red_squares)and(Pass=2))  then
         luminance := threshold[pass-1] + next_step
    else
         luminance := threshold[pass-1] - next_step;

luminance := max(luminance,lower_limit);
    luminance := min(luminance,upper_limit);

{
      Now, see how 'patient' responds to 'stimulus'...
    }
    if MOBSed then { we already have a good value }
       seen[pass] := (luminance < threshold[pass-1])
    else
       begin { actually need to test this location }
         decision := respond(worksheet[element]);
         seen[pass] := (decision = target_seen);
         total_presentations := succ(total_presentations);
         presentation := succ(presentation);
         Inc(numhist);
         with history[numhist] do
           begin
             ex := threshold[pass-1];
             lum := luminance;
             sens := sensitivity + variation_in_sensitivity;
             if seen[pass] then respn := 1 else respn := 0;
             error := 0;
             if FA_flaged then error := 1;
             if MISS_flaged then error := 2;
           end;
       end;

if not batch then
```

```
          begin
            if not seen[pass] then { show not seen as inverted }
              dynamic_plot(radius,meridian,luminance+inverted)
            else
              dynamic_plot(radius,meridian,luminance);
            stat_display(worksheet[element]);
          end;
      end;

until ((Passpres mod sample_size)=0) or escaped;

if (not escaped) then
    begin
      if not batch then
        begin
          SetVisualPage(1);
          SetActivePage(1);
        end;
      temp_cx := cx;
      temp_cy := cy;
      temp_scale_view := scale_view;
      scale_view := 1.0;
      xscale := GetMaxX/scale_view;
      yscale := xscale*(Xasp/Yasp);

cx := GetMaxX div 2;
      cy := GetMaxY div 2;
      { now, show the result of this pass with full screen display }
      if not batch then
        begin
          setviewport(0,0,GetMaxX,GetMaxY,clipon);
          plotaxis;
        end;

repeat
        done := true;

for i := 1 to 76 do
          with worksheet[i] do
            begin
              color := lightgreen;
              if seen[pass] then cflag := 1 else cflag := 0;
              polar_to_cart(radius/90.0,meridian*pi/180.0,rx,ry);
              make_screen_coord(rx,ry,lx,ly);
              numeric_plotXY(lx,ly,cflag,color);

{ determine the number of non-empty neighbors }
              nenSame := 0;
              nenDiff := 0;
              for ni := 1 to 8 do
                if (neighbors[i,ni]<>xx) then
                  if same(i,neighbors[i,ni]) then Inc(nenSame)
                  else Inc(nenDiff);

{ ================================================================ }
```

{  new addition  retest points which may be possible
                     misses or false alarms. At present
                     the code only compiles statistics on
                     retested point (if done). It does not
                     do a comparision of previous results. } retest := seen[pass+1];
repeat

{ process the neighbors }
  WSame := 0.0;
  WDiff := 0.0;
  for ni := 1 to 8 do
    begin
      n := neighbors[i,ni];
      if n<>xx then
        with worksheet[n] do
          begin
            color := lightblue;
            if Same(i,n)
              then color := lightgreen;
            if seen[pass] then sflag := 1 else sflag := 0;
            { change colors if there is a conflict with expected values
              or add weighting }
            if color=lightgreen then { same }
              if sflag<>cflag then
                color := lightred
              else
                WSame := WSame + 1.0;
            if color=lightblue then  { different }
              if sflag=cflag then
                color := white
              else
                WDiff := WDiff + 1.0;
            numeric_plotXY(lx+nlocX[ni],ly+nlocY[ni],sflag,color);
          end;
    end; { neighbor loop }

WSame := WSame/nenSame;
WDiff := WDiff/nenDiff;
NSame := gen_index(trunc(WSame*100));
NDiff := gen_index(trunc(WDiff*100));
history[numhist].ns := NSame;
history[numhist].nd := NDiff;

if seen[pass+1]
    and not(i in (Seed_Points+BS_points))
    and retest
    and (Possible_FA(seen[pass])
         or Possible_Miss(seen[pass])) then
  begin
    numpres[i] := numpres[i] + 1;
    Inc(PassPres);
    Inc(num_retested);

```
            decision := respond(worksheet[i]);
            retested[pass] := 1;
            seen[pass] := (decision = target_seen);
            seen[pass+1] := false;
            done := false;
            Pattern_Highlight(lx,ly,brown);

Inc(numhist);
            with history[numhist] do
              begin
                ex := threshold[pass-1];
                lum := luminance;
                sens := sensitivity + variation_in_sensitivity;
                if seen[pass] then respn := 1 else respn := 0;
                error := 0;
                if FA_flaged then error := 1;
                if MISS_flaged then error := 2;
              end;
          end
        else
          retest := false;

until not retest;

{ ================================================================ }

SetTextJustify(RightText,CenterText);
      numeric_plotXY(lx-12,ly-8,NSame,cyan);
      numeric_plotXY(lx-12,ly,NDiff,magenta);
      numeric_plotXY(lx-12,ly+8,next_step,yellow);
      numeric_plotXY(lx-4,ly+16,sensitivity,lightgray);
      numeric_plotXY(lx+12,ly+16,threshold[pass-1],red);
      SetTextJustify(CenterText,CenterText);
    end;

until done;

Heuristics;

SetTextJustify(RightText,CenterText);
  { display agreement matrix }
  for IDiff := 0 to 6 do
    begin
      numeric_plotXY(42+18*IDiff,6,PAgree[IDiff],lightgreen);
      numeric_plotXY(24,16+9*IDiff,PAgree[IDiff],lightblue);

sumDiff := 0;
      for ISame := 0 to 6 do
        begin
          numeric_plotXY(42+18*ISame,16+9*IDiff,IMatrix[ISame,IDiff],
                         lightmagenta);
          CumIMatrix[pass,ISame,IDiff] := CumIMatrix[pass,ISame,IDiff]
                                          + IMatrix[ISame,IDiff];
          sumDiff := sumDiff+IMatrix[ISame,IDiff];
        end;
```

```
          numeric_plotXY(42+7*18,16+9*IDiff,sumDiff,yellow);

numeric_plotXY(10,cy+4+10*IDiff,IDiff,lightmagenta);
        numeric_plotXY(34,cy+4+10*IDiff,PAgree[IDiff],white);
      end;

for ISame := 0 to 6 do
      begin
        sumSame := 0;
        for IDiff := 0 to 6 do
          sumSame := sumSame + IMatrix[ISame,IDiff];
        numeric_plotXY(42+18*ISame,16+9*7,SumSame,yellow);
      end;

{ save number tested total to this pass }
  CumIPres[pass] := CumIPres[pass] + starting_presentation
                                     + PassPres - 14;

{ save number retested for later printout }
  CumPresMat[pass] := CumPresMat[pass] + num_retested;

if not batch then
    begin
    { key }
      SetTextJustify(LeftText,CenterText);
      setcolor(lightgreen); OutTextXY(8,GetMaxY-48,'SAME:');
      setcolor(cyan);       OutTextXY(56,GetMaxY-48,'% index');
      setcolor(lightblue);  OutTextXY(8,GetMaxY-38,'DIFFERENT:');
      setcolor(magenta);    OutTextXY(96,GetMaxY-38,'% index');
      setcolor(lightred);   OutTextXY(8,GetMaxY-28,'Conflicting SAME');
      setcolor(white);      OutTextXY(8,GetMaxY-18,'Conflicting DIFFERENT');
      SetTextJustify(RightText,CenterText);
      OutTextXY(GetMaxX-8,GetMaxY-18,'Manifold: '+filman);
      Str(num_retested:0,offset_str);
      OutTextXY(GetMaxX-8,GetMaxY-38,'# Retested = '+offset_str);
      SetColor(lightcyan);
      Str(Pass:0,offset_str);
      OutTextXY(GetMaxX-8,6,'RIOTS : Pass '+offset_str);
      SetTextJustify(CenterText,CenterText);
      SetColor(lightgreen);
      OutTextXY(cx,6,'SEEN(1)   NOT SEEN(0)');
      if Respond_type = Simulation then
        begin
          OutTextXY(cx,GetMaxY-4,'Press any key to continue');
          pause_for_any_key;
        end;
      TextColor(lightgreen);

{ restore to normal screen }
      SetVisualPage(0);
      SetActivePage(0);
    end;
cx := temp_cx;
cy := temp_cy;
scale_view := temp_scale_view;
```

```
      xscale := GetMaxX/scale_view;
      yscale := xscale*(Xasp/Yasp);
      if not batch then setquadview(1);
    end;

total_presentations := total_presentations + num_retested;

end; { end of PASS 1 or 2 } procedure PASS3;
{ assumes that latest expected value is in worksheet[i].threshold[pass-1] } var
    lSame,
    lDiff,
    sumSame,
    sumDiff,
    offset,
    starting_presentation,
    lum,
    i,
    ni,
    num_retested,
    passpres : integer;
    numpres : array [1..76] of byte;  { number of presentations per element this pass }
    retest : boolean;

procedure get_next_target (var e:integer);
    var
      done_prepass : boolean;
      i            : integer;
  begin
    if (Passpres mod sample_size) <> 0 then
      begin
        done_prepass := true;
        for i := 1 to sample_size do
          if worksheet[i].Mobsed then
            done_prepass := done_prepass
                            and (numpres[i] > (Passpres div sample_size));
        if not done_prepass then
          repeat
            e := trunc(random(sample_size)+1);
          until (numpres[e] <= (Passpres div sample_size))
                and worksheet[e].Mobsed
        else
          repeat
            e := trunc(random(sample_size)+1);
          until numpres[e] <= (Passpres div sample_size)
      end
    else
      e := 1;
  end;
begin
```

```
starting_presentation := total_presentations;

{ clear out agreement matrix }
for ISame := 0 to 6 do
  for IDiff := 0 to 6 do
    IMatrix[ISame,IDiff] := 0;

passpres := 0;
for i := 1 to 76 do numpres[i] := 0;

if not batch then
  begin
    GotoXY(49,13);
    Write('Pass 3');
  end;

get_next_target(next_element);
repeat if keypressed then respond_to_keyboard; { check for abort or step }
  if not batch then single_step_check;

RT_variation := initial_RT_variation;

{
    Choose a random target location without replacement for each pass!
  }
  element := next_element;
  get_next_target(next_element);

numpres[element] := numpres[element] + 1;
  Inc(Passpres);
  num_retested := 0;

with worksheet[element] do
    begin
      seen[pass+1] := true;

if element in Red_squares then { use opposite of PASS 2 }
        luminance := threshold[pass-1] + next_step
      else
        luminance := threshold[pass-1] - next_step;

luminance := max(luminance,lower_limit);
      luminance := min(luminance,upper_limit);

{
        Now, see how 'patient' responds to 'stimulus'...
      }
      if threshold[pass] <> -1 then { we already have a good value }
        seen[pass] := (luminance < threshold[pass-1])
      else
        begin { actually need to test this location }
          decision := respond(worksheet[element]);
          seen[pass] := (decision = target_seen);
```

```
              total_presentations := succ(total_presentations);
              presentation := succ(presentation);
              Inc(numhist);
              with history[numhist] do
                begin
                  ex := threshold[pass-1];
                  lum := luminance;
                  sens := sensitivity + variation_in_sensitivity;
                  if seen[pass] then respn := 1 else respn := 0;
                  error := 0;
                  if FA_flaged then error := 1;
                  if MISS_flaged then error := 2;
                end;
            end;

if not batch then
          begin
            if not seen[pass] then { show not seen as inverted }
              dynamic_plot(radius,meridian,luminance+inverted)
            else
              dynamic_plot(radius,meridian,luminance);
            stat_display(worksheet[element]);
          end;
      end;

until ((Passpres mod sample_size)=0) or escaped;

if (not escaped) then
  begin
    if not batch then
      begin
        SetVisualPage(1);
        SetActivePage(1);
      end;
    temp_cx := cx;
    temp_cy := cy;
    temp_scale_view := scale_view;
    scale_view := 1.0;
    xscale := GetMaxX/scale_view;
    yscale := xscale*(Xasp/Yasp);

cx := GetMaxX div 2;
    cy := GetMaxY div 2;
    { now, show the result of this pass with full screen display }
    if not batch then
      begin
        setviewport(0,0,GetMaxX,GetMaxY,clipon);
        plotaxis;
      end;

repeat
      done := true;

for i := 1 to 76 do
        with worksheet[i] do
```

```
begin
  color := lightgreen;
  if seen[pass] then cflag := 1 else cflag := 0;
  polar_to_cart(radius/90.0,meridian*pi/180.0,rx,ry);
  make_screen_coord(rx,ry,lx,ly);
  numeric_plotXY(lx,ly,cflag,color);

{ determine the number of non-empty neighbors }
  nenSame := 0;
  nenDiff := 0;
  for ni := 1 to 8 do
    if (neighbors[i,ni]<>xx) then
      if same(i,neighbors[i,ni]) then Inc(nenSame)
      else Inc(nenDiff);

{ ================================================================ }

{ ** new addition ** retest points which may be possible
                       misses or false alarms. At present
                       the code only compiles statistics on
                       retested point (if done). It does not
                       do a comparision of previous results. } retest := seen[pass+1];
  repeat

{ process the neighbors }
    WSame := 0.0;
    WDiff := 0.0;
    for ni := 1 to 8 do
      begin
        n := neighbors[i,ni];
        if n<>xx then
          with worksheet[n] do
            begin
              color := lightblue;
              if Same(i,n)
                then color := lightgreen;
              if seen[pass] then sflag := 1 else sflag := 0;
              { change colors if there is a conflict with expected values
                or add weighting }
              if color=lightgreen then { same }
                if sflag<>cflag then
                  color := lightred
                else
                  WSame := WSame + 1.0;
              if color=lightblue then  { different }
                if sflag=cflag then
                  color := white
                else
                  WDiff := WDiff + 1.0;
              numeric_plotXY(lx+nlocX[ni],ly+nlocY[ni],sflag,color);
            end;
      end; { neighbor loop }
```

```
    WSame := WSame/nenSame;
    WDiff := WDiff/nenDiff;
    NSame := gen_index(trunc(WSame*100));
    NDiff := gen_index(trunc(WDiff*100));
    history[numhist].ns := NSame;
    history[numhist].nd := NDiff;

if seen[pass+1]
        and not(i in (Seed_Points+BS_points))
        and retest
        and (Possible_FA(seen[pass])
            or Possible_Miss(seen[pass])) then
      begin
        numpres[i] := numpres[i] + 1;
        Inc(PassPres);
        Inc(num_retested);
        decision := respond(worksheet[i]);
        retested[pass] := 1;
        seen[pass] := (decision = target_seen);
        seen[pass+1] := false;
        done := false;
        Pattern_Highlight(lx,ly,brown);

Inc(numhist);
        with history[numhist] do
          begin
            ex := threshold[pass-1];
            lum := luminance;
            sens := sensitivity + variation_in_sensitivity;
            if seen[pass] then respn := 1 else respn := 0;
            error := 0;
            if FA_flaged then error := 1;
            if MISS_flaged then error := 2;
          end;
      end
    else
        retest := false;

until not retest;

{ ============================================================== }

SetTextJustify(RightText,CenterText);
    numeric_plotXY(lx-12,ly-8,NSame,cyan);
    numeric_plotXY(lx-12,ly,NDiff,magenta);
    numeric_plotXY(lx-12,ly+8,next_step,yellow);
    numeric_plotXY(lx-4,ly+16,sensitivity,lightgray);
    numeric_plotXY(lx+12,ly+16,threshold[pass-1],red);
    SetTextJustify(CenterText,CenterText);
  end;

until done;

Heuristics;
```

```
    SetTextJustify(RightText,CenterText);
{ display agreement matrix }
 for IDiff := 0 to 6 do
   begin
     numeric_plotXY(42+18*IDiff,6,PAgree[IDiff],lightgreen);
     numeric_plotXY(24,16+9*IDiff,PAgree[IDiff],lightblue);

sumDiff := 0;
     for ISame := 0 to 6 do
       begin
         numeric_plotXY(42+18*ISame,16+9*IDiff,IMatrix[ISame,IDiff],
                       lightmagenta);
         CumIMatrix[pass,ISame,IDiff] := CumIMatrix[pass,ISame,IDiff]
                                      + IMatrix[ISame,IDiff];
         sumDiff := sumDiff+IMatrix[ISame,IDiff];
       end;
     numeric_plotXY(42+7*18,16+9*IDiff,sumDiff,yellow);

numeric_plotXY(10,cy+4+10*IDiff,IDiff,lightmagenta);
     numeric_plotXY(34,cy+4+10*IDiff,PAgree[IDiff],white);
   end;

for ISame := 0 to 6 do
   begin
     sumSame := 0;
     for IDiff := 0 to 6 do
       sumSame := sumSame + IMatrix[ISame,IDiff];
     numeric_plotXY(42+18*ISame,16+9*7,SumSame,yellow);
   end;

{ save number tested total to this pass }
 CumIPres[pass] := CumIPres[pass] + starting_presentation
                                  + PassPres - 14;

{ save number retested for later printout }
 CumPresMat[pass] := CumPresMat[pass] + num_retested;

if not batch then
   begin
     { key }
     SetTextJustify(LeftText,CenterText);
     setcolor(lightgreen); OutTextXY(8,GetMaxY-48,'SAME:');
     setcolor(cyan);       OutTextXY(56,GetMaxY-48,'% index');
     setcolor(lightblue);  OutTextXY(8,GetMaxY-38,'DIFFERENT:');
     setcolor(magenta);    OutTextXY(96,GetMaxY-38,'% index');
     setcolor(lightred);   OutTextXY(8,GetMaxY-28,'Conflicting SAME');
     setcolor(white);      OutTextXY(8,GetMaxY-18,'Conflicting DIFFERENT');
     SetTextJustify(RightText,CenterText);
     OutTextXY(GetMaxX-8,GetMaxY-18,'Manifold: '+filman);
     Str(num_retested:0,offset_str);
     OutTextXY(GetMaxX-8,GetMaxY-38,'# Retested = '+offset_str);
     SetColor(lightcyan);
     Str(Pass:0,offset_str);
     OutTextXY(GetMaxX-8,6,'RIOTS : Pass '+offset_str);
     SetTextJustify(CenterText,CenterText);
```

```
              SetColor(lightgreen);
              OutTextXY(cx,6,'SEEN(1)   NOT SEEN(0)');
              if Respond_type = Simulation then
                begin
                  OutTextXY(cx,GetMaxY-4,'Press any key to continue');
                  pause_for_any_key;
                end;
              TextColor(lightgreen);

{ restore to normal screen }
              SetVisualPage(0);
              SetActivePage(0);
            end;
          cx := temp_cx;
          cy := temp_cy;
          scale_view := temp_scale_view;
          xscale := GetMaxX/scale_view;
          yscale := xscale*(Xasp/Yasp);
          if not batch then setquadview(1);
        end;

total_presentations := total_presentations + num_retested;

end; { end of PASS 3 } begin   { R*I*O*T*S main }

Escaped := false;
  targets_left := sample_size;

{ up manifold counter }

Inc(CumN);
{  if CumN = 1 then InitPatMat;} if not batch then
    begin
      TextColor(lightred);
      GotoXY(41,20);
      Write('Offset:');
      TextColor(lightgreen);
    end;

for pass := starting_pass to ending_pass do
   begin
      case pass of
          0 : Pass0;
        1..2 : Pass1or2;
          3 : Pass3;
      end;
      if Pass > 0 then
        begin
          assign(aggree_file,'d:\batchout\aggree.dat');
          if not ExistFile('d:\batchout\aggree.dat') then
```

```
              rewrite(aggree_file)
            else
              reset(aggree_file);
            seek(aggree_file,filesize(aggree_file));
            aggree_info.imatrix := imatrix;
            aggree_info.fname   := copy(filman,1,6);
            aggree_info.pass    := pass;
            write(aggree_file,aggree_info);
            close(aggree_file);
          end;
      end;

needs_header := true;
    for i := 1 to 76 do with worksheet[i] do
      if error_print
          and
          (abs(sensitivity-threshold[numreps]) > 3)
          and
          (numhist > 0) then
        begin { output history to printer }
          if needs_header then
            begin
              Write(LST,chr(27)+'&k2S');
              Writeln(lst,copy(filman,1,6):6,':','targ':8,' : ','exp':5,'cal':5,'dif':5,
                       ' (ex,lum,sens,resp,ns,nd)...');
              needs_header := false;
            end;
          write(lst,i:15,' : ',sensitivity:5,threshold[numreps]:5,
                  sensitivity-threshold[numreps]:5,'   ');
          for j := 1 to numhist do
            with history[j] do
              write(lst,'(',ex:0,',',lum:0,',',sens:0,',',respn:0,',',ns:0,',',nd:0,') ');
          writeln(lst);
        end;

if not needs_header then Writeln(LST,chr(27)+'&k0S','-----');

end;

end.

{.LW153}  {.P-}  {.P012} {.PL60}                                  APPENDIX B
{$R-}    {Range checking off}
{$S-}    {Stack checking off}
{$I+}    {I/O checking on}
{$N+}    {numeric coprocessor}
{$O+,F+} program kraken;

{
Welcome to Kraken.  For background of this program see:

Johnson, C. A., Kennedy, R. L., Keltner, J. L. (1984).  Kraken: A
    comprehensive visual field simulation program.  Unpublished manuscript.
    Department of Ophthalmology, University of California, Davis.
```

Shapiro, L. R., Johnson, C. A., Kennedy, R. L. (1989). KRAKEN: A computer
    simulation procedure for static, kinetic, suprathreshold static and
    heuristic perimetry. In A. Heijl (Ed.), Perimetry Update 1988/89:
    Proceedings of the VIIIth international perimetry society meeting.
    Amsterdam: Kugler & Ghedini Publications.

Requires Turbo Pascal Ver. 5.0

Modified and extended from the original RSX pascal and RATFOR version (1984)
by: Lionel R. Shapiro
    Dept. of Ophthalmology
    University of CA, Davis.
}
{ library files }
  uses
    Overlay,
    Dos,Crt,Graph,TPDos,TPCrt,
    TPString,TPMenu,
    TPEdit,
    KRMENU,
    plotpak,
    timelib,
    PadPak,
    trig,
    dwight,
    Globals,
    randomz,
    respn,
    gname,
    HC30_2,
    Simparam,
    min_max,
    UStatic,
    Simplest,
    humcen30,
    MOBSC30,
    supra30,
    riots,
    pause;

var
    name : string;
    lst : text;

{ misc. Kraken procedures/functions }

{$F+}
  procedure KrakenExitProc;
{$F-}
{
  This procedure handles any last minute housekeeping for kraken.
  Specifically it disposes of previously allocated memory.
} begin

```
    ExitProc := SaveExitProc;
    dispose(reference_manifold);
    dispose(patient_manifold);
    ClrScr;
    GotoXY(1,20);
    TextColor(lightgreen);
    Writeln('<< end of program output >>');

end;
procedure plot_manifold(quad:integer;
                        var manifold : man_type);
  label
    wrap_up;

var
    ir,itheta,radius,
    color,
    ix,iy,vfx1,vfy1,vfx2,vfy2 : integer;
    x,y,r,theta,r0,t0,one_deg : real;
    poly : array[1..8] of integer;
    s : string[3];

x1,y1,x2,y2 : real;
    ulx,uly,lrx,lry : integer;

begin { plot_manifold }
  case quad of
    0 : begin   { full screen }
          vfx1 := 0;              vfy1 := 0;
          vfx2 := GetMaxX;        vfy2 := GetMaxY;
        end;
    1 : begin   { upper right }
          vfx1 := GetMaxX div 2;  vfy1 := 0;
          vfx2 := GetMaxX;        vfy2 := GetMaxY div 2;
        end;
    2 : begin   { upper left }
          vfx1 := 0;              vfy1 := 0;
          vfx2 := GetMaxX div 2;  vfy2 := GetMaxY div 2;
        end;
    3 : begin   { lower left }
          vfx1 := 0;              vfy1 := GetMaxY div 2;
          vfx2 := GetMaxX div 2;  vfy2 := GetMaxY;
        end;
    4 : begin   { lower right }
          vfx1 := GetMaxX div 2;  vfy1 := GetMaxY div 2;
          vfx2 := GetMaxX;        vfy2 := GetMaxY;
        end
    else begin   { centered }
          vfx1 := (GetMaxX div 4);      vfy1 := (GetMaxY div 4)-50;
          vfx2 := trunc(GetMaxX * 0.75); vfy2 := trunc(GetMaxY * 0.75)-50;
        end;
  end;
  setviewport(vfx1,vfy1,vfx2,vfy2,clipon);
  one_deg := pi/180;
{
```

```
          for ir := 0 to 90 do
            begin
              if keypressed then if ord(readkey)=27 then goto wrap_up;
              r := ir/90.0;
              theta := 359.0 * one_deg;
              polar_to_cart(r,theta,x,y); make_screen_coord(x,y,ix,iy);
              poly[7] := ix; poly[8] := iy;
              for itheta := 0 to 359 do
                begin
                  Moveto(ix,iy);
                  theta := itheta * one_deg;
                  polar_to_cart(r,theta,x,y); make_screen_coord(x,y,ix,iy);
                  color := colormap[sens_index[manifold[ir,itheta]]];
                  setcolor(color);
                  SetFillStyle(solidfill,color);
                  poly[1] := poly[7]; poly[2] := poly[8];
                  poly[7] := ix;      poly[8] := iy;
                  if r = 0 then r0 := 0 else r0 := r-one_deg;
                  t0 := theta-one_deg;
                  polar_to_cart(r0,t0,x,y);    make_screen_coord(x,y,poly[3],poly[4]);
                  polar_to_cart(r0,theta,x,y); make_screen_coord(x,y,poly[5],poly[6]);
                  FillPoly(4,poly);
                end;
            end;
    }
    { alternative plotting routine ... }
        polar_to_cart(1.0,0.0,x1,y1);
        polar_to_cart(1.0,pi/2.0,x2,y2);
        make_screen_coord(-x1,y2,ulx,uly);
        make_screen_coord(x1,-y2,lrx,lry);
        for iy := uly to lry do
          for ix := ulx to lrx do
            begin
              if keypressed then if ord(readkey)=27 then goto wrap_up;
              screen_to_ideal(ix,iy,x1,y1);
              cart_to_polar(x1,y1,r,theta);
              if r <= 1.0 then
                begin
                  color := colormap[
                                    sens_index[
                                               manifold[round(r*90.0),round(theta*180.0/pi)]
                                              ]
                                   ];
                  PutPixel(ix,iy,color);
                end;
            end;

wrap_up:
   { axis }
   setcolor(black);
   Moveto(0,cy); Lineto(GetMaxX,cy);
   Moveto(cx,0); Lineto(cx,GetMaxY);
   SetTextJustify(LeftText,TopText);
   { 10deg reference circles }
   for i:=1 to 9 do
```

```
      begin
        radius := round(xscale*(i/9.0));
        Circle(cx,cy,radius);
        if (i mod 3) = 0 then { label at 30, 60 and 90 deg. }
          begin
            Str(trunc(i*10):0,s);
            s := s + chr(248); { add degree symbol }
            OutTextXY(radius+cx+2,cy+2,s);
          end;
      end;
    SetTextJustify(CenterText,CenterText);
    setcolor(lightblue);
    Rectangle(0,0,cx*2-1,cy*2);
    setviewport(0,0,GetMaxX,GetMaxY,clipon);
  end;
procedure initalize_model;
{
 Reads the model-specific parameters from a *.MOD file?
 Uses the list of (r,theta) coordinates in *.GRD file to
 initialize the worksheet with sensitivity values from *.MAN
 and *.REF files.
}
  type
    long_string = string[80];

var
    i,color : integer;
    senstr : string;

procedure get_manifold(fname : long_string;
                         var manifold : man_type);
    var
      man : file of man_type;
      ir,itheta : integer;
      b :byte;

begin
    if ExistFile(fname) then
      begin
        assign(man,fname);
        reset(man);
        read(man,manifold);
        close(man);
      end
    else
      begin
        GotoXY(1,25); textcolor(lightred);
        Write(fname,' not found!!!');
        halt;
      end;
  end;

begin

{ initalize_model }
  test_type := static;
```

```
test_time := 0;
RT_sum := 0;
mean_reaction_time := (max_RT+min_RT)/2.0;

age_psychometric := initial_age_psychometric;
age_miss_weighting := initial_age_miss_weighting;
age_FA_weighting := initial_age_FA_weighting;
age_RT_weighting := initial_age_RT_weighting;
radial_psychometric := initial_radial_psychometric;
radial_miss_weighting := initial_radial_miss_weighting;
radial_FA_weighting := initial_radial_FA_weighting;
radial_RT_weighting := initial_radial_RT_weighting;

if AutoReference and (last_filref <> filref) then
  get_manifold(concat(datadir,filref),reference_manifold^);   { get age-reference manifold values }
last_filref := filref;
get_manifold(concat(datadir,filman),patient_manifold^);    { get patient manifold values } for i := 1 to number_of_targets do
  with worksheet[i] do
    begin
      sensitivity := patient_manifold^[radius,meridian];
      normal := reference_manifold^[radius,meridian];
      if (Respond_type <> Simulation) and (eye in ['L','l']) then
        { flip worksheet coordinates }
        meridian := ((180 - meridian) + 360) mod 360
    end;

Graph_quad := 2;
if not (batch or (device_type in [manual,simple_kinetic])) then
  if not brief_display then
    plot_manifold(Graph_quad,patient_manifold^)  { plot full manifold }
  else
    begin                               { plot manifold at target points only }
      setquadview(Graph_quad);
      plotaxis;
      for i := 1 to number_of_targets do
        with worksheet[i] do
          dynamic_plot(radius,meridian,sensitivity);
    end;

SetTextJustify(LeftText,TopText);
Setcolor(lightgreen);
if (not batch) and (device_type <> manual) then OuttextXY(1,1,filman);
SetTextJustify(CenterText,CenterText);

{ display information }
if device_type <> manual then
  begin
    TextColor(lightgreen); GotoXY(1,14); Write(device_name[device_type]);
    TextColor(lightred); GotoXY(1,15); Write(' Normal reference: ');
    TextColor(lightgreen); Write(copy(filref,1,pos('.',filref)-1));
    TextColor(lightred); GotoXY(1,16); Write(' Pattern: ');
    TextColor(lightgreen); Write(grd_name);
  end;
```

```
          if not batch then
            begin
              { show color scale }
              textcolor(lightblue);
              if device_type<>manual then
                begin
                  GotoXY(30,14); Write('Sens. Stim.');
                  for i:=1 to 10 do
                    begin
                      textcolor(colormap[i]);
                      GotoXY(30,i+14);
                      Write(sensitivity[i]:4,target[i]:6);
                    end;
                end;
            end
          else
            begin
              textcolor(lightgreen);
              GotoXY(1,13);
              write(copy(filman,1,6));
            end;
        end;

{$O simplest }
        {$O humcen30 }
        {I manualsc }
        {I pattern  }
        {$O riots    }
        {$O mobsc30  }
        {$O supra30  }
        {I autosc   }
procedure strat;

{
  Strat (an integral part of the KRAKEN package) controls which test strategies
  will be used to test the patients included in our visual field data base.
  Each device (or common groups of devices) are emulated in seperate case
  statements here within.  The STATIC, KINETIC or HEURISTIC routines are called
  by each device section to perform the rudimentary parts of the test procedure.
  Suprathreshold static procedures are handled by the STATIC routine.
} var
    start          : integer;
    seen           : boolean;
    i              : integer;

begin  { STRAT - main } if (not batch)
     AND (device_type <> manual)
     AND (Respond_type = Simulation) then
    begin
      textcolor(lightred);
      gotoXY(1,19);write('FATG');
      gotoXY(1,20);write('AGE ');
```

```
      gotoXY(1,21);write('RADL');
    end;
{ zero out appropate portion of model }
  for element := 1 to number_of_targets do
    with worksheet[element] do
      begin
        index := element;
        luminance := normal + suprathreshold_offset;
        last_seen_lum := 0;
        summed_luminance := 0;
        reversals := 0;
        presentation := 0;
        next_step := max_step_size;
        open := true;
        for i := 0 to max_reps do threshold[i] := 0;
        for i := 1 to 5 do seen[i] := true;
        numreps    := 0;
        direction := dimmer;
        numhist    := 0;
        Resolved  := false;
        MOBSed    := false;
        color_square := 0;
        for i := 1 to 5 do
          retested[i] := 0;
        for i := 1 to max_history do with history[i] do
          begin
            ex     := 0;    lum   := 0;
            sens  := 0;    respn := 0;
            error := 0;    ns    := 0;
            nd    := 0;
          end;
      end;

total_presentations := 0;
  start := 0;

case device_type of
{
    manual              : begin
                            manual_scan;
                          end;
}
    simple_static       : begin
                            for element := 1 to number_of_targets do
                              with worksheet[element] do
                                if random < 0.5 then
                                  begin
                                    direction := dimmer;
                                    luminance := luminance - next_step;
                                  end
                                else
                                  begin
                                    direction := brighter;
                                    luminance := luminance + next_step;
                                  end;
                            sample_size := number_of_targets;
```

```
                              targets_left := number_of_targets;
                              simple_static_procedure;
                          end;
{
    simple_kinetic      : begin
                              auto_scan;
                          end;
}
    heuristic_static    : begin
                              sample_size := number_of_targets;
                              Heuristic_static_RIOTS;
                          end;

humphrey_central_30 : begin
                              if respond_type = Simulation then
                                begin
                                  upper_limit := 50;
                                  lower_limit := 0;
                                end;
                              for element := 1 to number_of_targets do
                                with worksheet[element] do
                                  begin
                                    direction := dimmer;
                                    if not(element in Seed_Points) then
                                      open := false
                                    else
                                      luminance := 24;
                                  end;
                              sample_size := number_of_targets;
                              targets_left := number_of_targets;
                              Humphrey_central_30_2_threshold;
                          end;

supra_central_30    : begin
                              for element := 1 to number_of_targets do
                                with worksheet[element] do
                                  begin
                                    direction := dimmer;
                                    if not(element in Seed_Points) then
                                      open := false
                                    else
                                      luminance := 24;
                                  end;
                              sample_size := number_of_targets;
                              targets_left := number_of_targets;
                              Supra_central_30_2_Screen;
                          end;

mobs_central_30     : begin
                              for element := 1 to number_of_targets do
                                with worksheet[element] do
                                  begin
                                    direction := dimmer;
                                    if not(element in Seed_Points) then
                                      open := false
                                    else
```

```
                        luminance := 24;
                      end;
                  sample_size := number_of_targets;
                  targets_left := number_of_targets;
                  MOBS_central_30_2_threshold;
              end else
      writeln(' Error > ',
          'You have specified a device which cannot be simulated at this time.')
  end;

end; { STRAT } procedure Report(filout : filename);
  const
    sp : char = ' ';
  type
    data_rec_type = record
                      name              : string[35];
                      age               : integer;
                      eye               : char;
                      test_date         : string[8];
                      test_time         : string[8];
                      test_type         : char; { [R]iots vs [H]umphrey }
                      elapsed_time      : string[11];
                      total_num_presentations : integer;
                      refraction        : real;
                      thresholds        : array[1..76,1..2] of integer;
                      presentations     : array[1..76] of integer;
                    end;

var
    data_file : file of data_rec_type;
    data_rec : data_rec_type;
    out : text;
    element : integer;
    thresh,
    i,j,fnum,x,diff,
    total   : integer;
    Escaped : boolean;

begin
  if Respond_type <> Simulation then
    begin
      gotoxy(1,25);
      TextColor(Lightred);
      Write('Data is being stored... Please be patient.');
      data_rec.eye := eye;
      with data_rec do
        begin
          name := patient_rec.name;
          age  := patient_rec.age;
          test_date := GetCurDateStr;
          test_time := copy(con_time(start_time),1,8);
```

```
              elapsed_time := con_time(run_time);
              total_num_presentations := total_presentations;
              refraction := refraction_index;
              for i := 1 to 76 do
                presentations[i] := worksheet[i].presentation;
              case device_type of
                humphrey_central_30 :
                  begin
                    for element := 1 to 76 do
                      for i := 1 to 2 do with worksheet[element] do
                        thresholds[element,i] := threshold[i];
                    test_type := 'H';
                  end;
                heuristic_static :
                  begin
                    for element := 1 to 76 do with worksheet[element] do
                      begin
                        thresholds[element,1] := threshold[numreps];
                        if MOBSed then
                          thresholds[element,2] := 1
                        else
                          thresholds[element,2] := 0;
                      end;
                    test_type := 'R';
                  end
                else
                  begin
                    for element := 1 to 76 do
                      for i := 1 to 2 do with worksheet[element] do
                        thresholds[element,i] := threshold[i];
                    test_type := 'O'; { other }
                  end;
              end;
          end;
      assign(data_file,'SHRIMP.DAT');
      reset(data_file);
      seek(data_file,filesize(data_file));
      write(data_file,data_rec);
      close(data_file);
    end
  else
    begin
      Val(copy(filout,4,3),fnum,i); { get file number from filename }
      if not batch then
        begin
          assign(out,outputdir+filout);
          rewrite(out);
          writeln(out,' NUMTAR=',number_of_targets:3,' ',
                      '    RAD',
                      ' MERID',
                      '  SENS',
                      '  NORM',
                      ' LUMIN',
                      ' SmLUM',
                      ' REVRS',
                      '   DIR',
```

```
                         '  PRES',
                         '  STEP',
                         ' THRSH',
                         ' THRH2');
        end;
    total := 0;
    for element := 1 to number_of_targets do
      with worksheet[element] do
        begin thresh := 0;
{
          thresh := threshold[numreps];
}
          if device_type in [humphrey_central_30,
                             mobs_central_30] then
            diff := -(threshold[1]-sensitivity)
          else
            diff := -(threshold[numreps]-sensitivity);

if not batch then
            writeln(out,' TARGET(',element:3,')',
                              radius:6,
                              meridian:6,
                              sensitivity:6,
                              normal:6,
                              luminance:6,
                              summed_luminance:6,
                              reversals:6,'  ',
                              outdir[direction]:4,
                              presentation:6,
                              next_step:6,
                              threshold[1]:6,
                              threshold[2]:6)
          else
            begin
              write(reportfile,fnum:0,sp,                    { 1 }
                              element:0,sp,                   { 2 }
                              radius:0,sp,                    { 3 }
                              meridian:0,sp,                  { 4 }
                              sensitivity:0,sp,               { 5 }
                              normal:0,sp,                    { 6 }
                              diff:0,sp,                      { 7 }
                              presentation:0);                { 8 }
              for x := 1 to max_hum_reps do                   { 9.. }
                  write(reportfile,sp,threshold[x]:0);
{ special for riots: }
              if device_type = heuristic_static then
                begin
                  for x := 1 to 3 do
                      write(reportfile,sp,retested[x]);
                    write(reportfile,sp,color_square);
                  end;
                writeln(reportfile);
              end;
```

```pascal
            if debug_report and (abs(sensitivity-thresh)>1) then
              writeln(Lst,'File',fnum:4,' TARGET(',element:3,')',
                          radius:4,meridian:4,' :',sensitivity:5,
                          normal:5,luminance:5,threshold[1]:5,
                          diff:5,
                          reversals:5,' ',outdir[direction]:5,
                          presentation:5,next_step:5,threshold[2]:5);

total := total + presentation;

end;

if batch then
        writeln(reportfile_summary,fnum:4,
                                  total:5,
                                  test_time:10:2)
      else
        close(out);
    end;

end;

Procedure get_patient_info(fname : fname_type;
                           var patrec : patient_records);
  var
    patfile         : file of patient_records;
    i,num_patients  : integer;

begin
  assign(patfile,concat(homedir,patsfname));
  reset(patfile);
  num_patients := filesize(patfile);
  i := 0;
  repeat
    i:=i+1;
    seek(patfile,i-1);
    read(patfile,patrec);
  until (copy(fname,1,6)=copy(patrec.right_eye.filename,1,6))
        or(copy(fname,1,6)=copy(patrec.left_eye.filename,1,6))
        or(i=num_patients);
  close(patfile);
end;
  function get_age_group(age:integer):integer;
  begin
    case age of
       0..20 : get_age_group := 1;
      21..30 : get_age_group := 2;
      31..40 : get_age_group := 3;
      41..50 : get_age_group := 4;
      51..60 : get_age_group := 5;
      61..70 : get_age_group := 6;
      71..99 : get_age_group := 7;
      else get_age_group := 1;
    end;
  end;
  function match_age_group(c:char;age:integer):boolean;
```

```
    begin
      c := upcase(c);
      if c = 'A' then match_age_group := true
      else
        case age of
          0..20 : if c='B' then match_age_group := true else match_age_group := false;
          21..30 : if c='C' then match_age_group := true else match_age_group := false;
          31..40 : if c='D' then match_age_group := true else match_age_group := false;
          41..50 : if c='E' then match_age_group := true else match_age_group := false;
          51..60 : if c='F' then match_age_group := true else match_age_group := false;
          61..70 : if c='G' then match_age_group := true else match_age_group := false;
          71..99 : if c='H' then match_age_group := true else match_age_group := false;
          else match_age_group := false;
        end;
  end;
{.PA} begin  { KRAKEN -- main block -- } assign(response_file,'d:\batchout\response.dat');
rewrite(response_file);

OvrInit('KRAKEN.OVR');
  if OvrResult <> 0 then writeln('INIT-Overlay error:', OvrResult);
  OvrInitEMS;
  if OvrResult <> 0 then writeln('EMS--Overlay error:', OvrResult);

InitGraph(GraphDriver,GraphMode,'');
  SaveExitProc := ExitProc;
  ExitProc := @KrakenExitProc;
  cx := round(GetMaxX/4.0);
  cy := round(GetMaxY/4.0);
  GetAspectRatio(xasp,yasp);

GraphDriver := Detect;
  ClearDevice;
  DirectVideo := false;
  make_flash;  { make the dynamic point/stimuli indicator }

RestoreCRTMode;

randomize(0,0);
  start_time := RealTime;
  new(reference_manifold);
  new(patient_manifold);
  done := false;
  escaped := false;
  Conf_Mode := true;
  initialize_parameters;

{ for Riots development }
  CumN := 0;
  for i := 0 to 6 do
    for j := 0 to 6 do
      for k := 1 to 5 do
```

```
            CumIMatrix[k,i,j] := 0.0;
      for i := 1 to 5 do
        begin
          CumIPres[i] := 0;
          CumPresMat[i] := 0.0;
        end;

{ InitConfMenu(Current_Menu);} InitMainMenu(Current_Menu);

if ParamCount > 0 then { we have a filename for multibatch mode }
       begin
         multibatch := true;
         assign(multifil,homedir+ParamStr(1));
         reset(multifil);
       end;

repeat { Main execution loop }

ClrScr;
        GotoXY(1,25);
        TextColor(lightblue);
        Write('Device is currently ',device_name[device_type]:0,'.');
   repeat
      if not multibatch then key := MenuChoice(Current_Menu,Ch)
      else begin
            i := 0;
            if not eof(multifil) then read(multifil,i)
            else done := true;
            key := i;
          end;
      if ch<>#27 then process_choice(key);
    until ((key = 48) or done) and (ch<>#27);
    EraseMenu(Current_Menu,False);

if not done then
      begin if batch then
          begin
            nor_start := 1;
            nor_fin := 350;

GotoXY(1,1);
            Writeln('          BATCH MODE...');

prefix := 'NOR';

if not retest_mode then
              begin
                Writeln;
                if multibatch then readln(multifil);
                if multibatch then for i := 1 to 3 do read(multifil,prefix[i]) else
                  ReadString ('                         Enter file prefix => ',
                          WhereY,1,3,lightgreen,lightred,lightred,Escaped,prefix);
                if prefix <> 'PAT' then file_prefix := prefix;
```

```
Writeln;
if multibatch then read(multifil,nor_start) else
ReadInteger('                         Starting file number -> ',
            WhereY,1,3,lightgreen,lightred,0,350,Escaped,nor_start);
Writeln;
if multibatch then read(multifil,nor_fin) else
ReadInteger('                         Ending file number -> ',
            WhereY,1,3,lightgreen,lightred,0,350,Escaped,nor_fin);

Writeln; Writeln;
Writeln('Choose an age group:');
Writeln;
Writeln('     a.  All ages        e.  41-50');
Writeln('     b.  0-20            f.  51-60');
Writeln('     c.  21-30           g.  61-70');
Writeln('     d.  31-40           h.  71-99');
Writeln;
ShowReadChar := True;
if multibatch then readln(multifil,groupchar,groupchar) else
ReadCharacter(' Your choice -> ',WhereY,1,lightgreen,['A'..'H'],groupchar);
ShowReadChar := False;
      end
    else { retest mode }
      begin
        groupchar := 'A';
        Writeln;
        Writeln;
        if multibatch then readln(multifil,nor_fin) else
        ReadInteger('                         Number of tests to do -> ',
                WhereY,1,3,lightgreen,lightred,0,350,Escaped,nor_fin);
      end;
    last_filref := '';
    Writeln;
    foofilename := 'FOO.DAT';
{
    ReadString ('                         Enter FOO filename => ',
            WhereY,1,12,lightgreen,lightred,lightred,Escaped,foofilename);
}
  end;

Delay(1000);

if not (device_type in [manual,simple_kinetic]) then
  begin
    assign(infile,concat(homedir,filgrd));
    reset(infile);
    readln(infile,number_of_targets);
    readln(infile,grd_name);
    readln(infile,scale_view);
    scale_view := 6.0 * scale_view/90.0;
    for i := 1 to number_of_targets do
      with worksheet[i] do
        readln(infile,radius,meridian);
    close(infile);
  end
```

```
    else
      begin
        scale_view := 6.0 * 75.0/90.0;
        grd_name := 'Kinetic';
        number_of_targets := 0;
      end;

show_values := (scale_view < 6.0); { determine if we have room to display
                                         numeric values at target locations }
    xscale := GetMaxX/scale_view;
    yscale := xscale*(Xasp/Yasp);

{ initialize simulation timer }
    start_time := RealTime;
    last_time := start_time;

if batch then
      begin
        InitGraph(GraphDriver,GraphMode,'');
        num_batch := starting_batch_number;
repeat
  str(num_batch:0,numstr);
  numstr := '00' + numstr;
  filReport := outputdir + 'BATCH'
              + copy(numstr,length(numstr)-2,3) + '.DAT';
  filReport_summary := outputdir + 'BATSM'
              + copy(numstr,length(numstr)-2,3) + '.DAT';
  Inc(num_batch);
until not(ExistFile(filReport));

if report_generation then
  begin
    assign(reportfile,filReport);
    rewrite(reportfile);
    assign(reportfile_summary,filReport_summary);
    rewrite(reportfile_summary);
    GotoXY(40,14); Write('Output files: ');
    GotoXY(42,15); Write(filReport);
    GotoXY(42,16); Write(filReport_summary);
  end;
if retest_mode then
  begin
    GotoXY(5,18); Write('Test # ');
  end;

num_norm := nor_start;
if prefix = 'PAT' then file_prefix := 'GLO';
repeat
  str(num_norm:0,numstr);
  numstr := '00'+ numstr;
  if not retest_mode then
    filman := file_prefix+copy(numstr,length(numstr)-2,3)+'.MAN'
  else
    begin
      GotoXY(12,18); Write(num_norm:0);
    end;
```

```
        filout := copy(filman,1,pos('.',filman))+'OUT';
        if ExistFile(datadir+filman) then
          begin
            get_patient_info(filman,patient_rec);
            filref := age_name[get_age_group(patient_rec.age)]+'.REF';
            if match_age_group(groupchar,patient_rec.age) then
              begin
                initialize_model;
                strat;
              end;

if report_generation then report(filout);

end;
        Inc(num_norm);
        if (num_norm > nor_fin)
          and (prefix='PAT')
          and (file_prefix <> 'OND') then
          begin
            num_norm := nor_start;
            file_prefix := 'OND';
          end;
      until (num_norm > nor_fin) or escaped;

if report_generation then
        begin
          Close(reportfile);
          Close(reportfile_summary);
        end;

run_time := RealTime-start_time;
    end else
    begin { do only once } filout := copy(filman,1,pos('.',filman))+'OUT';

{ initialize patient and normal simulation information } patient_rec.age := 0;
      eye := 'R';
      patient_rec.name := '';

if Respond_type = Simulation then
        get_patient_info(filman,patient_rec)
      else
        begin
          ClrScr;
          GotoXY(1,15);
          Writeln('** Please enter the following information:');
          repeat
            name := patient_rec.name;
            ReadString ('         patient''s name -> ',17,1,32,lightgreen,
              lightred,lightred,Escaped,name);
            patient_rec.name := name;
```

```
      ReadInteger ('           patient''s age -> ',18,1,3,
        lightgreen,lightred,0,150,Escaped,patient_rec.age);
      ShowReadChar := True;
      ReadCharacter(' which eye to test [R,L] -> ',19,1,
        lightgreen,['R','L'],eye);
      ShowReadChar := False;
      ReadCharacter('Is this OK?',25,35,lightred,['Y','N'],ch);
    until upcase(ch)='Y';
    Sound(440);delay(50);NoSound;
    GotoXY(1,25);ClrEol;
  end;

if AutoReference then
    filref := age_name[get_age_group(patient_rec.age)]+'.REF';

refraction_index := 0.0;
  if Respond_type = HJPP then
    begin
      Refract;
      ReadReal('Enter refraction index: ',21,1,20,
        lightred,cyan,2,-5.50,5.50,Escaped,refraction_index);
    end;

if Respond_type <> Simulation then
    filman := filref;

filout := copy(filman,1,pos('.',filman))+'OUT';
  InitGraph(GraphDriver,GraphMode,'');
  initalize_model;

if device_type <> manual then
    begin
      if respond_type = Simulation then
        begin
          textcolor(lightblue);
          gotoXY(1,17);write('Weightings:');
          gotoXY(1,22);write('Patient parameters:');
          textcolor(lightred);
          gotoXY(1,18);write('PSYC':10,'RT':6,'MISS':6,'FA':6);
          gotoXY(1,23);write('mRT':6,'MISS':6,'FA ':6,'sdev':6);
        end
      else
        begin
          textcolor(lightblue);
          gotoXY(1,18);write('Patient age: ',patient_rec.age:3);
          gotoXY(1,19);write('        eye: ',eye:3);
          textcolor(lightred);
          gotoXY(1,23);write('mRT':6);
        end;

{ execute strategy to be tested }
      title := 'Dynamic Display';
      Graph_quad := 1;
      setquadview(Graph_quad);
      plotaxis;
      textcolor(lightblue);GotoXY(80-length(title),14);Write(title);
    end;
```

```pascal
if Respond_type <> Simulation then
  begin
    start_time := RealTime;
    last_time := start_time;
  end;

{ let's boogie! }
strat;

{ end simulation clock -- report elapsed time }
run_time := RealTime - start_time;

if not escaped then
  begin
if Respond_type <> Simulation then
  begin
    Sound(220);delay(1000);NoSound;
  end;

{ report: statistical calculations and output }
if report_generation then report(filout);

title := 'Final Values';
textcolor(lightblue);GotoXY(80-length(title),1);Write(title);

if not(device_type in [manual]) then
  begin
    if Respond_type = Simulation then
      pause_for_any_key;
    { code to display average of values at reversals...}
    title := 'Threshold';
    Graph_quad := 1;
    setquadview(Graph_quad);
    plotaxis;
    for i := 1 to number_of_targets do
      with worksheet[i] do
        case device_type of
          simple_kinetic :
            Mark_Plot(radius,meridian,threshold[j]);
          humphrey_central_30,
          mobs_central_30 :
            begin
              for j := 1 to 2 do
                if j <= numreps then
                  dynamic_plot_2(radius,meridian,
                                 threshold[j],j)
              end
            else
              dynamic_plot(radius,meridian,threshold[numreps])
        end; { case }
    textcolor(lightblue);GotoXY(80-length(title),1);Write(title);

{ code to calculate difference between Patient manifold and calculated
      threshold values -- and display differences }
    title := 'Difference';
    Graph_quad := 4;
```

```
                setquadview(Graph_quad);
                plotaxis;
                for i := 1 to number_of_targets do
                    with worksheet[i] do
                        begin
                            if device_type in [humphrey_central_30,
                                               mobs_central_30] then
                                vallum := threshold[1]-sensitivity
                            else
                                vallum := threshold[numreps]-sensitivity;

if vallum < 0 then val_color := lightred
                            else if vallum = 0 then val_color := lightgreen
                                    else val_color := white;
                                    if vallum < 0 then
                                        vallum := abs(vallum)+inverted;
                                    numeric_plot_2(radius,meridian,vallum,val_color);
                                end;
                            textcolor(lightblue);GotoXY(80-length(title),14);Write(title);
                            if Respond_type = Simulation then
                                title := 'Calc - MAN'
                            else
                                title := 'Calc - Ref';
                            textcolor(lightblue);GotoXY(80-length(title),25);Write(title);
                            GotoXY(76,23); textcolor(white);      write(' pos');
                            GotoXY(76,24); textcolor(lightred);   write('[neg]');
                            TextColor(lightblue);
                            GotoXY(41,24); Write('Pres: ',Total_presentations:0);
                            GotoXY(41,25); Write('Time: ',copy(con_time(test_time)+'0',4,8):0);

GotoXY(1,25);Write('':34);
                            pause_for_any_key;
                        end;

if device_type in [simple_kinetic] then
                        begin { plot full manifold }
                            Graph_quad := 2;
                            GotoXY(1,25);
                            textcolor(yellow);
                            Write('Plotting patient. ');
                            textcolor(white); Write('[ESC] to stop.');
                            plot_manifold(Graph_quad,patient_manifold^);
                            GotoXY(1,25);Write('':34);
                            pause_for_any_key;
                        end;
                end;
            end;
        end;

CloseGraph;
{
    Clrscr;
    TextColor(lightred);
    Writeln;
    Writeln;
    Writeln(' Elapsed execution time for the last procedure was: ',
            con_time(run_time));
```

```
}
{ for Riots development }
 if (device_type = heuristic_static)
    and (CumN > 0)
    and (not done)
    and (batch or
         YesOrNo('Would you like to have a printout of the average agreement matrices? ',
                 13,1,lightred,'N'))
    then
    begin
      { output cum matrix to printer }
      assign(lst,'E:\results\matrix.txt');
      if ExistFile('E:\results\matrix.txt') then append(lst) else rewrite(lst);
      Write(lst,chr(12));
      if not batch then
        Writeln(lst,'Riots development printout for ',CumN:0,' manifold(s).')
      else
        Writeln(lst,'Riots development printout for ',CumN:0,' [',prefix:0,'] manifold(s).',
                   '  ',filReport);
      datestr := getcurdatestr;
      Writeln(lst);
      Writeln(lst,datestr:79);
      Writeln(lst,'         Sensitivity ',chr(229),' = ',initial_standard_deviation:0:2);
      Writeln(lst,'             FA Rate = ',initial_FA_rate-1.0:0:2);
      Writeln(lst,'           Miss Rate = ',initial_miss_rate-1.0:0:2);
      Writeln(lst);
      Writeln(lst,'  % agreement matrix [same across; different down]');
      Writeln(lst);
      for k := 1 to ending_pass do
        begin
          Write(lst,'Pass ',k:0,'  ');
          for j := 0 to 6 do
            Write(lst,PAgree[j]:5,'  '); Writeln(lst,'      sum');
          Writeln(lst);
          for i := 0 to 6 do
            begin
              Write(lst,PAgree[i]:3,' : ');
              for j := 0 to 6 do
                Write(lst,CumIMatrix[k,j,i]/CumN:7:2);
              t := 0.0; for j := 0 to 6 do t := t + CumIMatrix[k,j,i]/CumN;
              Writeln(lst,t:10:2);
            end;
          Writeln(lst);
          Write(lst,' sum ');
          for j := 0 to 6 do
            begin
              t := 0.0; for i := 0 to 6 do t := t + CumIMatrix[k,j,i]/CumN;
              Write(lst,t:7:2);
            end;
          Writeln(lst);
          Write(lst,chr(27)+'&dD');
          Writeln(lst,' Average number of retested targets = ':65,CumPresMat[k]/CumN:0:1
                     ,'    [ ',CumIPres[k]/CumN:0:0,' ]');;
          Write(lst,chr(27)+'&d@');
        end;
      close(lst);
```

```
{ ************** massive printout to follow!!! ****************** }
{
      debugPrint_PatMat;

print_mobs_factors;
}
{ ****************************************************************** }
    end;

if (device_type = heuristic_static)
     and (CumN > 0)
     and (not done)
     and (batch or
          YesOrNo('Do you want to clear the agreement matrix? ',
                  15,1,lightred,'Y'))
     then
     begin
       CumN := 0;
       for i := 0 to 6 do
         for j := 0 to 6 do
           for k := 1 to 5 do
             CumIMatrix[k,i,j] := 0.0;
       for i := 1 to 5 do CumIPres[i] := 0;
     end;

TextColor(lightgreen);
    escaped := false;

until done;
  if multibatch then close(multifil);

close(response_file);

end.
      Unit Globals;

{ global declarations for kraken! } interface uses
        Graph,
        TPString,TPCrt,TPMenu,TPDos,
        TPEdit,
        PadPak,
        trig,
        ComPort,                    { Graphics tablet drivers }
        Dwight,                     { Portable Perimeter drivers }
        Printer;

const
        version : real = 1.08;
        { eliminates time consuming manifold plot }
        brief_display : boolean = true;
        debug_report : boolean = false;
        error_print : boolean = false;
```

```
starting_batch_number : integer = 400;

homedir : string = '';
datadir : string = 'D:\manifold\';
outputdir : string = 'E:\results\';
patsfname : string = 'patients.dat';
mnRho = 1;    mxRho = 90;
mnTheta = 0;  mxTheta = 359;
max_elements = 76;                          { size of worksheet } outdir : array[1..2] of string[5] = ('   -','   +');

dimmer                    = 1;    { a particularly ugly way to do this }
brighter                  = 2;
target_seen               = 4;
target_not_seen           = 8;
dimmer_target_seen        = 5;
brighter_target_seen      = 6;
dimmer_target_not_seen    = 9;
brighter_target_not_seen  = 10;

sensitivity : array[1..10] of integer = (37,35,32,30,27,25,22,20,15,0);
target : array[1..10] of string[5] = ('I/1c',
                                      'I/1e',
                                      'I/2c',
                                      'I/2e',
                                      'I/3c',
                                      'I/3e',
                                      'I/4c',
                                      'I/4e',
                                      'II/4e',
                                      'V/4e');
age_name : array[1..7] of string[5] = ('00-20','21-30','31-40','41-50',
                                      '51-60','61-70','71-99');
PAgree : array[0..6] of integer = (100,75,66,50,33,25,0);
maximum_stacksize = 128;
max_reps = 10;
max_history = 30;
max_hum_reps = 2; { number of retests for full threshold }
inverted = 100;
sens_index : array[0..50] of integer = (10,10,10,10,10,10,10,10,10,10,10,
                                        10,10,10,10, 9, 9, 9, 9, 9, 8,
                                         8, 7, 7, 7, 6, 6, 5, 5, 5, 4,
                                         4, 3, 3, 3, 2, 2, 1, 1, 1, 1,
                                         1, 1, 1, 1, 1, 1, 1, 1, 1, 1);
colormap : array[0..15] of integer =
          (
            black, yellow,
            lightred,
            lightgray,
            cyan,
            green,
            magenta,
            brown,
```

```
                  red,
                  darkgray,
                  blue, lightblue,
                  lightmagenta,
                  lightgreen,
                  lightcyan,
                  white
                  );

initials : array[91..96] of string = ('C.J.',
                                        'D.O.',
                                        'E.C.',
                                        'J.Q.',
                                        'J.T.',
                                        'M.V.');

type
  pset_type = record
                ndone : integer;
                max   : integer;
                config : array[1..70] of record
                                           filename : string[6];
                                           FA,Miss,SD : real;
                                         end;
              end;
  Patient_types = (Simulation,HFA,HJPP);

devices = ( null_device,
              simple_static,
              humphrey_central_30,
              heuristic_static,
              manual,
              simple_kinetic,
              supra_central_30,
              mobs_central_30 );

tests = ( static, method_of_limits, suprathreshold_static, kinetic );

possible_responses = integer;

Yes_or_No = ( no, yes );

fname_type = string[12];
  patient_records = record
                      name      : string[25];
                      age       : integer;
                      diagnosis : char; { either N, G, or O so far }
                      left_eye,
                      right_eye : record
                                    sensitivity_at_fixation : integer;
                                    filename : fname_type;
                                  end;
                    end;
```

```
histrec = record
            ex,lum,sens,respn,error,ns,nd : byte;
         end;

stack = record
          v : array[1..maximum_stacksize] of byte; { value }
          cur : integer;
        end;

mod_rec = record
            index              : integer;
            radius             : integer;
            meridian           : integer;
            sensitivity        : integer;
            normal             : integer;
            luminance          : integer;
            summed_luminance   : integer;
            reversals          : integer;
            direction          : possible_responses;
            presentation       : integer;
            next_step          : integer;
            open               : boolean; { available to query - flag }
            numreps            : integer; { # of repeated thresholds }
            threshold          : array[0..max_reps] of integer;
            seen               : array[1..5] of boolean;
            numhist            : byte;
            history            : array[1..max_history] of histrec;
            range              : integer;
            high_border,
            low_border         : stack;
            Resolved           : boolean;
            MOBSed             : boolean;
            last_seen_lum      : integer;
            color_square       : byte;
            retested           : array[1..5] of byte;
          end;

virmod_struc = array[1..max_elements] of mod_rec;

man_type = array[0..90,0..359] of byte;
ptr_man_type = ^man_type;

filename = string[12];              { types for file and    }
extstring = string[3];              {  file-extention names } const
  device_name : array[devices] of string = ('',
                                            'Simple Static',
                                            'Humphrey Full Threshold',
                                            'Heuristic Static',
                                            'Manual Kinetic Scan',
                                            'Simple Kinetic Scan',
                                            'Simple Suprathreshold Static',
                                            'MOBS Full Threshold'
                                            );
```

```
var
  reportfile,
  reportfile_summary,
  infile,
  multifil : text;
  grd_name : string[25];
  foofilename : string;
  filman,                                      { manifold file name }
  filpat,                                      { patient    "    " }
  filref,                                      { reference  "    " }
  last_filref,                                 { "  for batch mode  }
  filgrd,                                      { test grid  "    " }
  filmod,                                      { model      "    " }
  filout : filename;                           { indiv.     "    " }
  filbat,
  filReport,filReport_summary : string;        { batch output report}
  file_prefix,
  prefix : string;

worksheet : virmod_struc;                    { model information } device_type : devices;                       { testing apparatus }
  test_type : tests;                           { indicates test stratagy } last_time,
  run_time,                                    { simulation run time }
  start_time : double;                         { and start time      } number_of_targets,
  total_presentations,
  num_norm, num_batch,                         { for batch runs }
  nor_start,nor_fin,
  element,
  sample_size,
  targets_left,
  i,j,k : integer;                             { counter variable }
  numstr : string;

patient_rec : patient_records;

next_FA_flag : Yes_or_No;

age_FA_weighting,
  age_miss_weighting,
  age_psychometric,
  age_RT_weighting,
  FA_rate,
  final_RT_value,
  mean_reaction_time,
  miss_rate,
  radial_FA_weighting,
  radial_miss_weighting,
  radial_psychometric,
  radial_RT_weighting,
  RT_sum,
  RT_variation,
```

```
        refraction_index,
        test_time
                            : real;

eye,
        groupchar,
        ch                  : char;
        title               : string[80];

reference_manifold,
        patient_manifold    : ptr_man_type;

cx,cy               : integer; { center of display area eg. 1/4 screen coord }
        xasp,yasp           : word;    { aspect ratios }
        t,
        scale_view,                    { 0..6 where 6 is full view }
        xscale,yscale       : real;    { scaling for plotting to screen } vallum,val_color,
        Graph_quad,
        GraphDriver,
        GraphMode : integer;

Current_menu : Menu;
        Key          : MenuKey;

FA_flaged,
        MISS_flaged,
        Conf_Mode,
        escaped,
        done : boolean;
        next_element : integer;

SaveExitProc : Pointer;

{ for Riots development: }
    CumPresMat : array[1..5] of real;
    CumIPres   : array[1..5] of real;
    CumIMatrix : array[1..5,0..6,0..6] of real;
    CumN       : integer;

{ for Manual Kinetic study }
    Tech_fname : string;

datestr : string;

response_file : text;

implementation end.

unit simparam;

interface
```

```
uses Globals,HC30_2,TPMENU;

{
  This block of code contains the KRAKEN simulation parameters.
}
  var variation_in_sensitivity : integer;

criterion_reversals         : integer;
    exit_criteria               : integer;
    minimum_step_size           : integer;
    max_step_size               : integer;

fatigue_RT_factor           : real;

fatigue_psychometric_factor : real;
    fatigue_eccentricity_loss   : real;   { loss in dB per degree per second
                                            elapsed test time } initial_age_FA_weighting    : real;
    initial_age_miss_weighting  : real;
    initial_age_psychometric    : real;
    initial_age_RT_weighting    : real;

initial_radial_FA_weighting   : real;
    initial_radial_miss_weighting : real;
    initial_radial_psychometric   : real;
    initial_radial_RT_weighting   : real;

initial_FA_rate             : real;
    initial_miss_rate           : real;
    initial_RT_variation        : real;
    initial_standard_deviation  : real;

loss_criterion              : real;
    loss_psychometric           : real;

min_RT                      : real;
    max_RT                      : real;
    interstimulus_interval      : real;
    stimulus_duration           : real;

upper_limit                 : integer;
    lower_limit                 : integer;
    range_fraction              : real;

starting_pass               : integer; { for riots }
    ending_pass                 : integer;
    Agree_limit                 : integer; { for comparision to ISame or IDiff }
    Dissagree_limit             : integer; {  these define limits of integrity check }
    PASS1offset                 : integer;

suprathreshold_offset       : integer; { dB for riots/mobs pretest }
```

```
    element_to_follow          : integer;

Seed_Points                : set of 1..76;
    Fluc_Points                : set of 1..76;

{ simulation switches... } use_last_seen_threshold    : boolean;
    multibatch                 : boolean;
    HFA_gateway                : boolean;
    HFA_initialized            : boolean;
    retest_mode                : boolean;
    suspect_retest             : boolean;
    report_generation          : boolean;
    mobs_print                 : boolean;
    riots_print                : boolean;
    age_weighting_on           : boolean;
    eccentricity_weighting_on  : boolean;
    fatigue_weighting_on       : boolean;
    reaction_time_on           : boolean;
    timing_clock_on            : boolean;
    variable_reaction_time_on  : boolean;
    variable_sensitivity_on    : boolean;
    follow_on                  : boolean;
    sampling_with_replacement  : boolean;
    batch                      : boolean;
    single_step                : boolean;{ flags only one target/keypress }
    show_values                : boolean;{ displays sens/lum value if true }
    AutoReference              : boolean;
    respond_type               : Patient_types;

procedure initialize_parameters;
procedure process_choice (var key : MenuKey);

implementation uses Dos,TPDOS,TPCRT,TPString,
       TPEdit,gname,dwight,Randomz,KRMENU;

procedure initialize_parameters;
begin
    device_type := mobs_central_30;

criterion_reversals        := 3;     { 1..5 }
    exit_criteria              := 2;     { dB }
    minimum_step_size          := 2;     { 1..3 dB }
    max_step_size              := 4;     { 3..8 dB }
    fatigue_RT_factor          := 1.00;

fatigue_psychometric_factor := 0.001;   { increase in variability/sec }
    fatigue_eccentricity_loss   := 4.1666666667E-5; { dB loss/deg/sec } initial_age_FA_weighting   := 1.00;
    initial_age_miss_weighting := 1.00;
    initial_age_psychometric   := 1.00;
    initial_age_RT_weighting   := 1.00;
```

```
initial_radial_FA_weighting    := 1.00;
initial_radial_miss_weighting  := 1.00;
initial_radial_psychometric    := 1.00;
initial_radial_RT_weighting    := 1.00;

initial_FA_rate                := 1.00; { normal 2%, patients 5-6% }
initial_miss_rate              := 1.00; { normal 1%, patients 6-7% }
initial_RT_variation           := 1.00;

initial_standard_deviation     := 0.00; { 0..4 dB } loss_criterion                 := 10.0; { dB }
loss_psychometric              := 1.50; { increases variability by 50% } min_RT                         := 0.050; { sec }
max_RT                         := 1.250; { sec } interstimulus_interval         := 1.000; { sec }
stimulus_duration              := 0.200; { sec } upper_limit                    := 50; { sensitivity dB }
lower_limit                    := 0;  { sensitivity dB }
range_fraction                 := 1.0/3.0;

starting_pass                  := 0; { R*I*O*T*S }
ending_pass                    := 3;
Agree_limit                    := 0;
Dissagree_limit                := 6;
PASS1offset                    := 4;

suprathreshold_offset          := -2;

element_to_follow              := 25;

Seed_Points                    := Humphrey_Seed_Points;
Fluc_Points                    := [3,4,25..28,30,45,51,52];

{ simulation switches... } use_last_seen_threshold        := true;
multibatch                     := false;
HFA_gateway                    := false;
HFA_initialized                := false;
retest_mode                    := false;
suspect_retest                 := true;
report_generation              := true;
mobs_print                     := false;
riots_print                    := false;
age_weighting_on               := false;
eccentricity_weighting_on      := false;
fatigue_weighting_on           := false;
reaction_time_on               := false;
timing_clock_on                := true;
variable_reaction_time_on      := false;
variable_sensitivity_on        := false;
follow_on                      := false;
```

```
    sampling_with_replacement    := true;
    batch                        := false;
    single_step                  := false;
    AutoReference                := true;

Respond_type                 := Simulation;

filman                       := 'NOR045.MAN';
    filgrd                       := 'CEN30_2.GRD';
    filbat                       := 'MULTIBAT.DAT';
  end;

procedure process_choice {(var key : MenuKey)};
  var
    SR : SearchRec;
    i,j : integer;
    Escaped : boolean;
    fname : string;
    paramset : pset_type;
    fparam : file of pset_type;

procedure beep;
  begin
    Sound(880); Delay(25); NoSound;
  end;

procedure set_real(name : string; var num : real);
  begin
    if multibatch then read(multifil,num) else
    ReadReal(name+' == ',WhereY,WhereX,20,lightred,cyan,2,0.0,0.0,Escaped,num);
    beep;
  end;

procedure set_integer(name : string; var num : integer);
  begin
    if multibatch then read(multifil,num) else
    ReadInteger(name+' == ',WhereY,WhereX,20,lightred,cyan,0,0,Escaped,num);
    beep;
  end;

procedure set_switch(name : string; var switch : boolean);
    const offon : array[false..true] of string = ('OFF','ON');
    var dum,ch : char;
  begin
    Write(name:0,' is currently set to ',offon[switch]:0,'. ');
    Write('Change? (Y/N) ');
    if multibatch then
      begin
        read(multifil,dum,ch);
        switch := (upcase(ch)='T');  { ch can be T or F, for true or false resp. }
      end
    else
      if Upcase(readkey)='Y' then switch := not(switch);
    GotoXY(1,WhereY);Write('':79);
    GotoXY(1,WhereY);
```

```
    Write(name:0,' is currently set to ',offon[switch]:0,'.  ');
    GotoXY(1,WhereY);
    beep;
  end;

procedure set_device(key : MenuKey);
begin
  case key of
{
    925,2 : device_type := simple_kinetic;
}
    921,3 : begin
              device_type := simple_static;
              criterion_reversals := 2;
            end;

922,4 : begin
              device_type := humphrey_central_30;
              Seed_Points := Humphrey_Seed_Points;
              criterion_reversals := 1;
              suprathreshold_offset := -2;
            end;

923,5 : begin
              device_type := heuristic_static;
              Seed_Points := Humphrey_Seed_Points
                           + Additional_Seed_Points;
              criterion_reversals := 3;
              suprathreshold_offset := -6
            end;
{
    924,6 : device_type := manual;
}
        7 : begin
              device_type := humphrey_central_30;
              Seed_Points := Humphrey_Seed_Points
                           + Additional_Seed_Points;
              criterion_reversals := 1;
              suprathreshold_offset := -2;
            end;

80 : begin
              device_type := mobs_central_30;
              Seed_Points := Humphrey_Seed_Points;
              criterion_reversals := 3;
            end;

81 : begin
              device_type := supra_central_30;
              Seed_Points := [25];
              suprathreshold_offset := -6;
            end else
      begin
        textcolor(lightred);
```

```
            GotoXY(1,24);
            Sound(440); Delay(50); NoSound;
            Writeln('Sorry! Selected device is not available at this time.');
            textcolor(lightgreen);
            Delay(3000);
          end;
      end;
      GotoXY(1,19); Write(device_name[device_type]:78);
      beep;
    end;

procedure set_file_name(title,dir : string; ext : extstring;
                            var filenam : filename);
      var
        found, escaped : boolean;

begin
      { get file specifications }
        if not((ext='GRD') and (device_type = manual)) then
          repeat
            GotoXY(1,24);
            textcolor(lightgreen);
            Write('Enter file name for ',title:0,' [*.',ext:0,'] -> ');
            if multibatch then read(multifil,filenam) else
            getname(filenam,ext);
            found := ExistFile(concat(dir,filenam));
            escaped := filenam[1]=#27;
            if (not found) and (not escaped) then
              begin
                GotoXY(1,25);
                textcolor(lightred);
                Sound(440); delay(50); NoSound;
                Write(filenam:0,' not found!  Please try again (or [ESC] to quit)');
                GotoXY(1,24);
                Write('':79);
              end
          until found or escaped
        else
          Write('Please choose a device first.');
        if escaped then begin GotoXY(1,24); Write('':79); end;
      GotoXY(1,25); Write('':79);
      beep;
    end;

begin

Sound(880); Delay(10); NoSound; { mini beep! } textcolor(lightblue);
{
  GotoXY(50,20);
  if variable_sensitivity_on then
    Write('Variable Sensitivity':29)
  else
    Write('   Fixed Sensitivity':29);
```

```
  GotoXY(50,21);
  if fatigue_weighting_on then
    Write(' Fatigue Factors ON':29)
  else
    Write('Fatigue Factors OFF':29);

GotoXY(50,22);
  if (initial_FA_rate = 1.0)
      and(initial_MISS_rate = 1.0) then
    Write('Response Errors OFF':29)
  else
    Write(' Response Errors ON':29);
}
{
  GotoXY(50,19); Write(device_name[device_type]:29);
  if Conf_Mode then
    begin
      GotoXY(50,18); Write(trim(PatStr[select_eye]):29);
    end
  else
    begin
      GotoXY(50,24); Write(filgrd:29);
      GotoXY(50,25); Write(filman:29);
    end;
}
  textcolor(lightgreen);
  GotoXY(1,24); Write('':79);
  GotoXY(1,25); Write('':79);
  GotoXY(1,24);

case key of

2..7,
    80,81: set_device(key);

8 : set_integer('Criterion reversals',criterion_reversals);
       9 : set_integer('Minimum step size',Minimum_step_size);
      10 : set_integer('Maximum step size',Max_step_size);
      11 : set_real('ISI (sec)',Interstimulus_interval);
      12 : set_real('Stimulus duration (sec)',Stimulus_duration);
      13 : set_real('Minimum RT',min_rt);
      14 : set_real('Maximum RT',max_rt);
      15 : set_integer('Lower limit (dB)',lower_limit);
      16 : set_integer('Upper limit (dB)',upper_limit);
      17 : set_switch('Retest of suspect values',suspect_retest);
      19 : set_switch('Use last seen luminance as threshold',use_last_seen_threshold);

51 : set_integer('Starting pass #',starting_pass);
      52 : set_integer('Final pass #',ending_pass);
      53 : set_integer('Suprathreshold offset (db)',suprathreshold_offset);
      54 : set_switch('Mobs printout',Mobs_print);
      55 : set_integer('Agree limit [0..6]',Agree_limit);
      56 : set_integer('Disagree limit [0..6]',Dissagree_limit);
      57 : set_integer('PASS1: Offset',PASS1offset);
      58 : set_integer('PASS3: exit criteria',exit_criteria);
      65 : set_switch('Riots printout',Riots_print);
```

```
18 : set_switch('Single Stepping',single_step);

20 : set_real('Age FA weighting',Initial_age_FA_weighting);
21 : set_real('Age Miss weighting',Initial_age_miss_weighting);
22 : set_real('Age Psychometric',Initial_age_psychometric);
23 : set_real('Age RT weighting',Initial_age_RT_weighting);
24 : set_real('FA rate',Initial_FA_rate);
25 : set_real('Miss rate',Initial_Miss_rate);
26 : set_real('Radial FA weighting',Initial_radial_FA_weighting);
27 : set_real('Radial Miss weighting',Initial_radial_Miss_weighting);
28 : set_real('Radial Psychometric',Initial_radial_psychometric);
29 : set_real('RT variation',Initial_RT_variation);
30 : set_real('Standard deviation',Initial_standard_deviation);

32 : set_real('Fatigue eccentricity loss',fatigue_eccentricity_loss);
33 : ;
34 : set_real('Fatigue RT factor',fatigue_RT_factor);
35 : set_real('Fatigue psychometric factor',fatigue_psychometric_factor);
36 : set_real('Loss criterion',loss_criterion);
37 : set_real('Loss psychometric',loss_psychometric);

39 : set_switch('Age weighting',age_weighting_on);
40 : set_switch('Eccentricity weighting',eccentricity_weighting_on);
41 : set_switch('Fatigue weighting',fatigue_weighting_on);
42 : set_switch('Reaction time',reaction_time_on);
43 : set_switch('Timing clock',timing_clock_on);
44 : set_switch('Variable RT',variable_reaction_time_on);
45 : set_switch('Variable sensitivity',variable_sensitivity_on);
46 : set_file_name('Patient manifold',datadir,'MAN',filman);
47 : set_switch('Batch mode',batch);
48 : Write('Let''s go!');
49 : begin { Quit }
        done := true;
        Writeln('So Long!');
        Write('':79);
     end;
50 : begin
        set_switch('Follow a point',follow_on);
        GotoXY(1,24);
        if follow_on then { input point }
           set_integer('Point to follow',element_to_follow);
     end;
59 : set_switch('Report generation',report_generation);
60 : filgrd := 'CEN30_1.GRD';
61 : filgrd := 'CEN30_2.GRD';
62 : filgrd := 'PER60_1.GRD';
63 : filgrd := 'PER60_2.GRD';
64 : set_file_name('Test Pattern',homedir,'GRD',filgrd);
70 : begin
        set_switch('Retest',retest_mode);
        batch := batch or retest_mode;
     end;
71 : begin
        set_switch('MultiBatch mode',multibatch);
        if multibatch then
           begin
```

```
              ReadString ('Multibatch filename => ',WhereY,1,24,lightgreen,
                         lightred,lightred,Escaped,filbat);
              beep;
              assign(multifil,homedir+filbat);
              reset(multifil);
            end;
        end;

82 : begin { simulation RESPOND }
          beep;
          Respond_type := Simulation;
          GotoXY(1,25); Write('Patient: Simulation ');
        end;
   83 : begin
          beep;
          Respond_type := HFA;
          GotoXY(1,25); Write('Patient: HFA GATEWAY');
          lower_limit := 0;
          upper_limit := 50;
        end;
   84 : begin
          beep;
          Respond_type := HJPP;
          GotoXY(1,25); Write('Patient: HJPP        ');
          lower_limit := 11;
          upper_limit := 42;
          GotoXY(15,25); Write('Initializing.');
          Initialize_HJPP;
          GotoXY(15,25); Write('Homing.     ');
          Home_HJPP;
          GotoXY(15,25); Write('Ready.      ');
        end;

91..96 : if YesOrNo('You are '+initials[key]+'? [Y/N] ',24,1,lightmagenta,#0) then
           begin
             beep;
             { get parameters }
             Tech_fname := 'D:\kraken\'+ copy(initials[key],1,1)
                                       + copy(initials[key],3,1)
                                       + '.CNF';
             assign(fparam,Tech_fname);
             reset(fparam);
             read(fparam,paramset);
             close(fparam);
             if paramset.ndone < paramset.max then
               begin
                 Inc(paramset.ndone);
                 with paramset.config[paramset.ndone] do
                   begin
                     filman := filename + '.MAN';
                     initial_FA_rate := 1.0 + FA;
                     initial_Miss_rate := 1.0 + Miss;
                     initial_standard_deviation := SD;
                   end;
                 variable_sensitivity_on := initial_standard_deviation <> 0.0;
```

```
{ debugging block }
if existfile('D:\kraken\Lionel.x') then
  begin
GotoXY(1,15);
Writeln('file: ',filman);
Writeln('  FA: ',initial_FA_rate:0:2);
Writeln('Miss: ',initial_MISS_rate:0:2);
Writeln('  SD: ',initial_Standard_deviation:0:2);
Writeln;
Writeln('press any key to continue');
repeat until keypressed;
key := ord(readkey);
  end;
                    { set to run now! }
                      key := 48;
                    end
                  else
                    begin
                      GotoXY(1,25);
                      Write('*** no more sessions to run ***');
                      beep;
                      Delay(1000);
                      GotoXY(1,25);
                      Write('                              ');
                    end;
                end
              else
                begin
                  GotoXY(1,24);
                  Write('':79);
                  beep;
                  GotoXY(1,24);
                end;

{ blue plate specials phase 1 }
    101,104,107,110
      : filman    := 'NOR002.MAN'; { a typical normal - for demo }

102,105,108,111
      : filman    := 'GLO002.MAN'; { a glocoma patient           }

103,106,109,112
      : filman    := 'OND011.MAN'; { an optic neuritis patient   }
{
    199 : begin
            EraseMenu(Current_Menu,False);
            InitConfMenu(Current_Menu);
            Conf_Mode := true;
          end;
}

800 : AutoReference := true;
    801 : begin
            AutoReference := false;
            filref := '00-20.REF';
          end;
```

```
        802 : begin
                AutoReference := false;
                filref := '21-30.REF';
              end;
        803 : begin
                AutoReference := false;
                filref := '31-40.REF';
              end;
        804 : begin
                AutoReference := false;
                filref := '41-50.REF';
              end;
        805 : begin
                AutoReference := false;
                filref := '51-60.REF';
              end;
        806 : begin
                AutoReference := false;
                filref := '61-70.REF';
              end;
        807 : begin
                AutoReference := false;
                filref := '71-99.REF';
              end;

{ conference mode menus }
    901..
    904 : begin { select an eye }
             {select_eye := key - 900;}
              case key of
                901 : filman := 'NOR055.MAN';
                902 : filman := 'GLO002.MAN';
                903 : filman := 'OND011.MAN';
                904 : begin { select a random eye }
                        FindFirst('D:\Manifold\*.MAN',$3F,SR);
                        Randomize(0,0);
                        j := random(1000);
                        for i := 1 to j do
                          if DosError = 0 then
                            FindNext(SR)
                          else
                            FindFirst('D:\Manifold\*.MAN',$3F,SR);
                        filman := SR.name;
                      end;
              end;
{            GotoXY(50,18); Write(trim(PatStr[select_eye]):29);}
          end;

905 : begin { toggle variable sensitivity }
            variable_sensitivity_on := not variable_sensitivity_on;
            GotoXY(50,20);
            if variable_sensitivity_on then
              begin
                initial_standard_deviation := 2.0; { dB }
                Write('Variable Sensitivity':29);
```

```
                    end
                  else
                    begin
                      initial_standard_deviation := 0.0; { dB }
                      Write('  Fixed Sensitivity':29);
                    end;
                end;
    906 : begin { toggle fatigue factors }
            fatigue_weighting_on := not fatigue_weighting_on;
            GotoXY(50,21);
            if fatigue_weighting_on then Write(' Fatigue Factors ON':29)
              else                       Write('Fatigue Factors OFF':29);
          end;
    907 : begin { toggle response errors }
            GotoXY(50,22);
            if initial_FA_rate = 1.0 then
              begin { turn on response errors }
                initial_FA_rate   := 1.02; { set for normals }
                initial_miss_rate := 1.01;
                Write(' Response Errors ON':29);
              end
            else
              begin { turn off response errors }
                initial_FA_rate   := 1.00;
                initial_miss_rate := 1.00;
                Write('Response Errors OFF':29);
              end;
          end;

921..
  925 : set_device(key);

{

998 : begin
          EraseMenu(Current_Menu,False);
          ClrScr;
          GotoXY(35,16);
          TextColor(yellow);
          Write('Thank you!');
          Delay(4000);
          ClrScr;
          InitConfMenu(Current_Menu);
          Conf_Mode := true;
          initialize_parameters;
        end;
}
  999 : begin { Special }
          EraseMenu(Current_Menu,False);
          InitMainMenu(Current_Menu);
          Conf_Mode := false;
        end;

else
    begin
```

```pascal
            textcolor(lightred);
            write('SORRY, that option is not implemented at this time.');
            Sound(440); Delay(100); Nosound;
            Delay(500);
          end;
      end;

{ blue plate specials phase 2 }
    case key of
      101..103 : device_type := manual;
      104..106 : begin
                   device_type := simple_static;
                   max_step_size := 4;
                   minimum_step_size := 2;
                   criterion_reversals := 2;
                 end;
      107..109 : begin
                   device_type := humphrey_central_30;
                   max_step_size := 4;
                   minimum_step_size := 2;
                   criterion_reversals := 1;
                   Seed_Points := Humphrey_Seed_Points;
                 end;
      110..112 : begin
                   device_type := humphrey_central_30;
                   max_step_size := 4;
                   minimum_step_size := 2;
                   criterion_reversals := 1;
                   Seed_Points := Humphrey_Seed_Points + Additional_Seed_Points;
                 end;

end;

if (key >= 100) and (key < 199) then key := 48; { set to run } end;

begin
                end.
Unit HC30_2;

interface const
    xx = 0;
{
 pattern is as follows (index for neighbor(x,i)):

1  2  3
   4     5
   6  7  8
}
    neighbors : array[1..76,1..8] of 0..76
              = ((6,21,25,2,5,3,4,24),           {  1 }
                 (26,6,21,22,1,7,3,4),           {  2 }
                 (22,2,1,7,4,27,23,8),           {  3 }
```

(2,1,5,3,24,23,8,28), { 4 }
(21,25,29,1,9,4,24,44), { 5 }
(30,10,41,26,21,22,2,1), { 6 }
(42,22,2,11,3,31,27,23), { 7 }
(3,4,24,23,28,43,12,32), { 8 }
(25,29,33,5,13,24,44,60), { 9 }
(34,14,57,30,41,26,6,21), { 10 }
(58,42,22,15,7,35,31,27), { 11 }
(23,8,28,43,32,59,16,36), { 12 }
(29,33,37,9,17,44,60,72), { 13 }
(38,18,69,34,57,30,10,41), { 14 }
(70,58,42,19,11,39,35,31), { 15 }
(43,12,32,59,36,71,20,40), { 16 }
(33,37,xx,13,xx,60,72,xx), { 17 }
(xx,xx,xx,38,69,34,14,57), { 18 }
(xx,70,58,xx,15,xx,39,35), { 19 }
(59,16,36,71,40,xx,xx,xx), { 20 }
(10,41,45,6,25,2,1,5), { 21 }
(46,26,6,42,2,11,7,3), { 22 }
(7,3,4,27,8,47,43,12), { 23 }
(1,5,9,4,44,8,28,48), { 24 }
(41,45,49,21,29,1,5,9), { 25 }
(50,30,10,46,6,42,22,2), { 26 }
(11,7,3,31,23,51,47,43), { 27 }
(4,24,44,8,48,12,32,52), { 28 }
(45,49,53,25,33,5,9,13), { 29 }
(54,34,14,50,10,46,26,6), { 30 }
(15,11,7,35,27,55,51,47), { 31 }
(8,28,48,12,52,16,36,56), { 32 }
(49,53,xx,29,37,9,13,17), { 33 }
(xx,38,18,54,14,50,30,10), { 34 }
(19,15,11,39,31,xx,55,51), { 35 }
(12,32,52,16,56,20,40,xx), { 36 }
(53,xx,xx,33,xx,13,17,xx), { 37 }
(xx,xx,xx,xx,18,54,34,14), { 38 }
(xx,19,15,xx,35,xx,xx,55), { 39 }
(16,36,56,20,xx,xx,xx,xx), { 40 }
(14,57,61,10,45,6,21,25), { 41 }
(62,46,26,58,22,15,11,7), { 42 }
(27,23,8,47,12,63,59,16), { 43 }
(5,9,13,24,60,28,48,64), { 44 }
(57,61,65,41,49,21,25,29), { 45 }
(66,50,30,62,26,58,42,22), { 46 }
(31,27,23,51,43,67,63,59), { 47 }
(24,44,60,28,64,32,52,68), { 48 }
(61,65,xx,45,53,25,29,33), { 49 }
(xx,54,34,66,30,62,46,26), { 50 }
(35,31,27,55,47,xx,67,63), { 51 }
(28,48,64,32,68,36,56,xx), { 52 }
(65,xx,xx,49,xx,29,33,37), { 53 }
(xx,xx,38,xx,34,66,50,30), { 54 }
(39,35,31,xx,51,xx,xx,67), { 55 }
(32,52,68,36,xx,40,xx,xx), { 56 }
(18,69,73,14,61,10,41,45), { 57 }
(74,62,46,70,42,19,15,11), { 58 }
(47,43,12,63,16,75,71,20), { 59 }

```
            (9,13,17,44,72,48,64,76),      { 60 }
            (69,73,xx,57,65,41,45,49),     { 61 }
            (xx,66,50,74,46,70,58,42),     { 62 }
            (51,47,43,67,59,xx,75,71),     { 63 }
            (44,60,72,48,76,52,68,xx),     { 64 }
            (73,xx,xx,61,xx,45,49,53),     { 65 }
            (xx,xx,54,xx,50,74,62,46),     { 66 }
            (55,51,47,xx,63,xx,xx,75),     { 67 }
            (48,64,76,52,xx,56,xx,xx),     { 68 }
            (xx,xx,xx,18,73,14,57,61),     { 69 }
            (xx,74,62,xx,58,xx,19,15),     { 70 }
            (63,59,16,75,20,xx,xx,xx),     { 71 }
            (13,17,xx,60,xx,64,76,xx),     { 72 }
            (xx,xx,xx,69,xx,57,61,65),     { 73 }
            (xx,xx,66,xx,62,xx,70,58),     { 74 }
            (67,63,59,xx,71,xx,xx,xx),     { 75 }
            (60,72,xx,64,xx,68,xx,xx)      { 76 }
          );

Humphrey_Fluc_Points    : set of 1..76 = [3,4,25..28,30,45,51,52];

Humphrey_Seed_Points    : set of 1..76 = [25..28];
  Additional_Seed_Points  : set of 1..76 = [33..36,61..64];

BS_points               : set of 1..76 = [9,44];

implementation begin
end.
  unit min_max;
  interface function min(a,b:integer):integer;
    function max(a,b:integer):integer;

implementation function min{(a,b:integer):integer};
    begin
      if a < b then min := a else min := b;
    end;

function max{(a,b:integer):integer};
    begin
      if a > b then max := a else max := b;
    end;
  begin
  end.
unit plotpak;

interface
  uses TPdos,TPcrt,graph,globals,simparam;

procedure polar_to_cart (r,theta:real;var x,y:real);
  procedure cart_to_polar (x,y:real; var r,theta:real);
```

```pascal
procedure rad_to_deg ( r,t:real;var ir,it:integer );
procedure make_flash;
procedure plotaxis;
procedure make_screen_coord(x,y:real; var ix,iy:integer);
procedure screen_to_ideal(ix,iy:integer; var x,y:real);
procedure setquadview(quad:integer);
procedure dynamic_plot(r,theta,val:integer);
procedure dynamic_plot_2(r,theta,val,flag:integer);
procedure numeric_plot(r,theta,val,color:integer);
procedure numeric_plot_2(r,theta,val,color:integer);
procedure numeric_plotXY(ix,iy,val,color:integer);
procedure mark_plot(r,theta,val:integer);
procedure lineto_mark_plot(r,theta,val:integer);
procedure kinetic_plot(r,theta,val:integer);

implementation
   const
      lw_man : integer = 3;
      lw_norm : integer = 1;
      vfboarder : integer = lightblue;
      vfbackground : integer = black;
      flash_radius = 7;

var
      flash : pointer; { will point to image of circle to identify stimulus point
                        currently being looked at }
      flash_size,flash_ulx,flash_uly,
      flash_lrx,flash_lry : word;

{ the following procedures convert to and from polar coordinates and
  world coordinates X,Y: (-1..1,-1..1) } procedure polar_to_cart {(r,theta:real;var x,y:real)};
   begin
      x := r*cos(theta);
      y := r*sin(theta);
   end;

procedure cart_to_polar {(x,y:real; var r,theta:real)};
   begin
      r := sqrt(sqr(x)+sqr(y));
      if x < 0.0 then
                          theta := pi + arctan(y/x)    { quad.s II & III     }
      else if x > 0.0 then                              { quad.s I & IV      }
         if y > 0.0 then    theta := arctan(y/x)
         else               theta := 2*pi + arctan(y/x)
      else if y > 0.0 then theta := pi/2.0              { special cases if x=0 }
         else              theta := 1.5*pi;
   end;

procedure rad_to_deg {( r,t:real;var ir,it:integer )};
   { given radians returns degrees }
   begin
      ir := round(90.0*r);
      it := trunc(360.0+t*180.0/pi) mod 360;
   end;
```

```
procedure make_flash;
{ make flash spot for stimuli id }
 begin
   setcolor(white);
   circle(flash_radius,flash_radius,flash_radius);
   circle(flash_radius,flash_radius,flash_radius-1);
   circle(flash_radius,flash_radius,flash_radius-2);
   flash_ulx := 0; flash_uly := 0;
   flash_lrx := 2*flash_radius + 1; flash_lry := flash_lrx;
   flash_size := ImageSize(flash_ulx,flash_uly,flash_lrx,flash_lry);
   GetMem(flash,flash_size);
   GetImage(flash_ulx,flash_uly,flash_lrx,flash_lry,flash^);
   PutImage(flash_ulx,flash_uly,flash^,XORput);
 end;

procedure plotaxis;
   var
     i,radius,color : integer;
     s : string[3];
 begin
  { axis }
  ClearViewPort;
  setcolor(lightblue);
  Rectangle(0,0,cx*2,cy*2);
  Moveto(0,cy); Lineto(GetMaxX,cy);
  Moveto(cx,0); Lineto(cx,GetMaxY);
  SetTextJustify(LeftText,TopText);
  { 10deg reference circles }
  for i:=1 to 9 do
    begin
      radius := round(xscale*(i/9.0));
      Circle(cx,cy,radius);
      if (i mod 3) = 0 then { label at 30, 60 and 90 deg. }
        begin
          Str(trunc(i*10):0,s);
          s := s + chr(248); { add degree symbol }
          OutTextXY(radius+cx+2,cy+2,s);
        end;
    end;
  SetTextJustify(CenterText,CenterText);
 end;

procedure make_screen_coord {(x,y:real; var ix,iy:integer)};
{ converts ideal coordinates (0 to 1) : real >>> to >>> integer screen
 coordinates. Assumes that xscale and yscale exist. }
 begin
   ix := cx + round(xscale*(x));
   iy := cy + round(yscale*(-y));
 end;

procedure screen_to_ideal {(ix,iy:integer; var x,y:real)};
 { inverse of make_screen_coord }
  begin
    x := (ix - cx)/xscale;
    y := (cy - iy)/yscale;
  end;
```

```pascal
procedure setquadview{(quad:integer)};
  var
    vfx1,vfx2,vfy1,vfy2 : integer;
begin
  case quad of
    1 : begin   { upper right }
          vfx1 := GetMaxX div 2;  vfy1 := 0;
          vfx2 := GetMaxX;        vfy2 := GetMaxY div 2;
        end;
    2 : begin   { upper left }
          vfx1 := 0;              vfy1 := 0;
          vfx2 := GetMaxX div 2;  vfy2 := GetMaxY div 2;
        end;
    3 : begin   { lower left }
          vfx1 := 0;              vfy1 := GetMaxY div 2;
          vfx2 := GetMaxX div 2;  vfy2 := GetMaxY;
        end;
    4 : begin   { lower right }
          vfx1 := GetMaxX div 2;  vfy1 := GetMaxY div 2;
          vfx2 := GetMaxX;        vfy2 := GetMaxY;
        end
    else begin   { centered }
          vfx1 := GetMaxX div 4;  vfy1 := GetMaxY div 4;
          vfx2 := GetMaxX - vfx1; vfy2 := GetMaxY - vfy1;
        end;
  end;
  setviewport(vfx1,vfy1,vfx2,vfy2,clipon);
end;

procedure dynamic_plot{(r,theta,val:integer)};
  const
    fat_point : integer = 3;
    cir_rad : integer = 5;
    circolor : integer = white;

var
    tempcolor,color,ix,iy : integer;
    x,y : real;
    s : string[2];
    reverse : boolean;

begin
  if val >= inverted then
    begin
      val := val-inverted;
      reverse := true;
    end
  else
    reverse := false;
  color := colormap[sens_index[val]];
  setcolor(color);
  polar_to_cart(r/90.0,theta*pi/180.0,x,y);
  make_screen_coord(x,y,ix,iy);

PutImage(ix-flash_radius,iy-flash_radius,flash^,XORput);
```

```
      Circle(ix,iy,fat_point);
      SetFillStyle(1,color);
      FloodFill(ix,iy,color);
      Delay(10);
      PutImage(ix-flash_radius,iy-flash_radius,flash^,XORput);
      if reverse then putpixel(ix,iy,white);
      if show_values then
        begin
          if reverse then
            SetFillStyle(SolidFill,color)
          else
            SetFillStyle(EmptyFill,black);
          Bar(ix-8,iy-5,ix+8,iy+3);
          if reverse then setcolor(black);
          Str(val:2,s);
          OutTextXY(ix,iy,s);
        end;
  end;
end;

procedure dynamic_plot_2{(r,theta,val,flag:integer)};
  const
    fat_point : integer = 3;
    cir_rad : integer = 5;
    circolor : integer = white;

var
    tempcolor,color,ix,iy : integer;
    x,y : real;
    s : string[2];
    reverse : boolean;

begin
  if val >= inverted then
    begin
      val := val-inverted;
      reverse := true;
    end
  else
    reverse := false;
  color := colormap[sens_index[val]];
  setcolor(color);
  polar_to_cart(r/90.0,theta*pi/180.0,x,y);
  make_screen_coord(x,y,ix,iy);
  if flag = 2 then
    iy := iy+8;

Circle(ix,iy,fat_point);
  SetFillStyle(1,color);
  FloodFill(ix,iy,color);

if reverse then putpixel(ix,iy,white);
  if show_values then
    begin
      if reverse then
        SetFillStyle(SolidFill,color)
      else
```

```
      SetFillStyle(EmptyFill,black);
    if flag = 2 then
      Bar(ix-12,iy-5,ix+12,iy+3)
    else
      Bar(ix-8,iy-5,ix+8,iy+3);
    if reverse then setcolor(black);
    Str(val:2,s);
    if flag = 2 then
      OutTextXY(ix,iy,'\'+s)
    else
      OutTextXY(ix,iy,s);
   end;
end;

procedure numeric_plot_2{(r,theta,val,color:integer)};
  const
    fat_point : integer = 3;
    cir_rad : integer = 5;
    circolor : integer = white;

var
    tempcolor,ix,iy : integer;
    x,y : real;
    s : string[2];
    reverse : boolean;

begin
  if val >= inverted then
    begin
      val := val-inverted;
      reverse := true;
    end
  else
    reverse := false;
  setcolor(color);
  polar_to_cart(r/90.0,theta*pi/180.0,x,y);
  make_screen_coord(x,y,ix,iy);

Circle(ix,iy,fat_point);
  SetFillStyle(1,color);
  FloodFill(ix,iy,color);

if reverse then putpixel(ix,iy,white);
  if show_values then
    begin
      if reverse then
        SetFillStyle(SolidFill,color)
      else
        SetFillStyle(EmptyFill,black);
      Bar(ix-8,iy-5,ix+8,iy+3);
      if reverse then setcolor(black);
      Str(val:2,s);
      OutTextXY(ix,iy,s);
    end;
end;
```

```
procedure numeric_plot {(r,theta,val,color:integer)};
  const
    fat_point : integer = 3;
    cir_rad : integer = 5;

var
    ix,iy : integer;
    x,y : real;
    s : string[2];

begin
  setcolor(color);
  polar_to_cart(r/90.0,theta*pi/180.0,x,y);
  make_screen_coord(x,y,ix,iy);

Circle(ix,iy,fat_point);
  SetFillStyle(1,color);
  FloodFill(ix,iy,color);

if show_values then
    begin
      SetFillStyle(EmptyFill,0);
      Bar(ix-8,iy-5,ix+8,iy+3);
      Str(abs(val):2,s);
      OutTextXY(ix,iy,s);
    end;
end;

procedure numeric_plotXY {(ix,iy,val,color:integer)};
  var
    s : string[3];
begin
  if not batch then
    begin
      SetColor(color);
      Str(abs(val):0,s);
      OutTextXY(ix,iy,s);
    end;
end;
procedure mark_plot {(r,theta,val:integer)};
  var
    ix,iy : integer;
    x,y : real;

begin
  setcolor(colormap[sens_index[val]]);
  polar_to_cart(r/90.0,theta*pi/180.0,x,y);
  make_screen_coord(x,y,ix,iy);
  OutTextXY(ix,iy,'x');
end;

procedure lineto_mark_plot {(r,theta,val:integer)};
  var
    ix,iy : integer;
    x,y : real;
```

```
begin
  setcolor(colormap[sens_index[val]]);
  polar_to_cart(r/90.0,theta*pi/180.0,x,y);
  make_screen_coord(x,y,ix,iy);
  LineTo(ix,iy);
  OutTextXY(ix,iy,'x');
  MoveTo(ix,iy);
end;

procedure kinetic_plot {(r,theta,val:integer)};
  var
    color,ix,iy : integer;
    x,y : real;

begin
  color := colormap[sens_index[val]];
  polar_to_cart(r/90.0,theta*pi/180.0,x,y);
  make_screen_coord(x,y,ix,iy);
  putpixel(ix,iy,color);
end;

begin
end.
unit ustatic;

interface uses TPDos,TPCRT,Globals,simparam,timelib;

procedure static_banners;
procedure follow_show;
procedure follow_fin;
procedure respond_to_keyboard;
procedure single_step_check;
procedure stat_display(current_stimulus : mod_rec);

implementation procedure static_banners;
begin
  if not batch then
    begin
      TextColor(white);
      GotoXY(1,25);Write('S=Single Step On    [ESC]=QUIT');
      if follow_on then
        begin
          TextColor(lightblue);
          GotoXY(43,15);Write('Following target element #',element_to_follow:0);
          TextColor(lightred);
          GotoXY(41,16);Write('rad':5,'mer':5,'sen':5,'nor':5);
          GotoXY(41,18);Write('lum':5,'slm':5,'rev':5,'dir':5,'pre':5,'stp':5);
        end;
      textcolor(lightred);
      gotoXY(41,22);write('rad':5,'mer':5,'sen':5,'nor':5,'Tpre':10,'Etime':10);
```

```
      gotoXY(41,24);write('lum':5,'slm':5,'rev':5,'dir':5,'pre':5,'stp':5,
                    'Resolved':10);
    end;
end;

procedure follow_show;
begin
  if follow_on and (element=element_to_follow) then
    with worksheet[element] do
      begin
        gotoXY(41,17);write(radius:5,meridian:5,sensitivity:5,normal:5);
        gotoXY(41,19);write(luminance:5,summed_luminance:5,reversals:5,
                      outdir[direction]:5,presentation:5,next_step:5);
      end;
end;

procedure follow_fin;
begin
  if (follow_on and (not batch)) then with worksheet[element_to_follow] do
    begin
      gotoXY(41,17);write(radius:5,meridian:5,sensitivity:5,normal:5);
      gotoXY(41,19);write(luminance:5,summed_luminance:5,reversals:5,
                    outdir[direction]:5,presentation:5,next_step:5);
    end;
end;

procedure respond_to_keyboard;
  var
    ch : char;
begin
  ch := readkey;
  Sound(880); Delay(10); NoSound;
  case ord(upcase(ch)) of
    27  { esc } : begin
                    escaped := true;
                    single_step := false;
                    while keypressed do ch := readkey; { flush keyboard buf }
                  end;
    83  { 'S' } : single_step := not single_step;
    else {do nothing};
  end;
  if not single_step then
    begin
      textcolor(white);
      gotoXY(1,25); Write('S=SINGLE STEP      [ESC]=QUIT');
    end;
end;

procedure single_step_check;
  var
    co : integer;
begin
  if single_step and (not batch) then
  . begin
      co := 1;
      repeat
```

```
        delay(50);
        textcolor(co);
        if co = 15 then co := 0;
        Inc(co);
        gotoXY(1,25); write('[SP]=STEP  S=OFF   [ESC]=QUIT');
      until keypressed;
      respond_to_keyboard;
    end;
end;

procedure stat_display {(current_stimulus : mod_rec)};
  var t : string;
begin textcolor(lightgreen);
  t := con_time(test_time)+'0';

with current_stimulus do
    begin
      gotoXY(41,23);write(radius:5,meridian:5,sensitivity:5,normal:5,
                         total_presentations:10,
                         copy(t,4,8):10);
      gotoXY(41,25);write(luminance:5,summed_luminance:5,reversals:5,
                         outdir[direction]:5,presentation:5,next_step:5,
                         sample_size-targets_left:9);
    end;
end;

begin
end.
unit respn;

interface
  uses globals;

function respond(var current_stimulus:mod_rec) : possible_responses;

implementation
  uses TPdos,TPcrt,comport,dwight,simparam,timelib,min_max,HC30_2;

function gauss(standard_deviation, average:real): real;
{
  Gauss is a function that generates an approximation to a normal distribution
  when it is provided with a mean (e.g. current_stimulus(sensitivity)) and a
  standard deviation.

** note : for test purposes we are currently using Turbo's own random fn. **
          RANDOM - should return number on uniform distribution [0..1].
} function inv_norm( prob : real ) : real;
  {
    This function which returns the Z-score, z(prob), where 0 <= p <= 1,
    does much of the dirty work for GAUSS.  Uses a third order polynomial
``` approximation to the inverse normal distribution.
}

```
  const
    c0 = 2.515517;   d1 = 1.432788;
    c1 = 0.802053;   d2 = 0.189269;
    c2 = 0.010328;   d3 = 0.001308;

var
    q,z,t1,t2,t3 : real;

begin if prob > 0.5
      then   q := 1.0 - prob
      else   q := prob;

if q = 0.0
      then   q := 0.0000001;

t2 := ln(1/sqr(q));
    t1 := sqrt(t2);
    t3 := t1*t2;

z := t1 - (c0 + c1*t1 + c2*t2)/(1 + d1*t1 + d2*t2 + d3*t3);

if prob <= 0.5
      then inv_norm := -z
      else inv_norm := z;
    end;

begin
  gauss := average + inv_norm(random) * standard_deviation;
end;

{ SPECIAL - Portable perimeter interface for KRAKEN } function HJPP_respond(var current_stimulus:mod_rec) : possible_responses;
  const
    PPrange = 150.0;
    { the following table (provided by Dwight Howard) gives the PP equivalence
      values for the HFA -- assuming a size three target.  Index = HFA dB,
      value = HJPP D/A. }

PPtable : array[0..50] of integer
            =(  2,  2,  2,  2,  2,  2,  2,  2,  2,  2,  2,
                2,  2,  2,  7, 12, 16, 21, 25, 30, 34,
               38, 42, 45, 49, 53, 56, 60, 63, 67, 71,
               74, 77, 81, 85, 88, 91, 95, 98,101,105,
              108,111,114,117,120,123,125,128,130,134);

var
    on_time,
    reaction_time      : double;
```

```
      standard_deviation,
      sensitivity_value : real;
      respflg           : boolean;
      response          : Yes_or_No;

procedure timer;

begin { TIMER }
    RT_sum := reaction_time + RT_sum;
    if total_presentations > 0 then
      mean_reaction_time := RT_sum/total_presentations
    else
      mean_reaction_time := RT_sum;
    last_time := RealTime;
    test_time := last_time - start_time;
  end; { TIMER } function Button_Pressed : Yes_Or_No;
  begin
    if BUTTON then
      begin
        Sound(440);
        Button_pressed := YES;
        delay(15);
        NoSound;
      end
    else
        Button_pressed := NO;
  end;

begin { RESPOND }

{ prep. for stimulus }
  sensitivity_value := current_stimulus.sensitivity;
  variation_in_sensitivity := 0; { unknown value! }
  FA_flaged := false;
  MISS_flaged := false;
  response := no;

if device_type = simple_kinetic then
    begin
      respflg := Button;
      { move to new location }
      With Current_stimulus do
        MOVEARM( meridian, radius, FixOn );
      respflg := Button or respflg;
      STIMON(PPtable[Current_stimulus.luminance]);
      respflg := Button or respflg;
      if respflg then begin
                    Sound(220);
                    STIMOFF;
                    Delay(25);
                    Nosound;
                    response := yes;
                  end;
```

```
      end
    else
      begin
        { move to new location }
          With Current_stimulus do
            MOVEARM( meridian, radius, FixON );

{ delay ISI }
          repeat until (RealTime - last_time) >= InterStimulus_Interval;

{ set luminance level & start presentation }
          STIMON(PPtable[Current_stimulus.luminance]);
          on_time := RealTime;

{ Stimulus duration... }
          repeat
            reaction_time := RealTime - on_time;
            response := Button_pressed;
          until (reaction_time >= Stimulus_duration) or (response = yes);

STIMOFF;

{ move to new location }
          With worksheet[next_element] do
            MOVEARM_NOWAIT( meridian, radius, FixON );
        { remaining time allowed for response }
          while (device_type <> simple_kinetic) and
                (reaction_time <= max_RT) and (response <> yes) do
            begin
              reaction_time := RealTime - on_time;
              response := Button_pressed;
            end;

timer;

{ output latest patient parameters }
          if (not batch) and (device_type <> manual) then
            begin
              textcolor(lightgreen);
              gotoXY(1,24);write(mean_reaction_time:6:2);
            end;
        end;

if response = yes then
      hjpp_respond := target_seen
    else
      hjpp_respond := target_not_seen;

end; { HJPP RESPOND }

{ SPECIAL - HFA Gateway interface for KRAKEN }
function HFA_respond(current_stimulus:mod_rec) : possible_responses;
  const
    CR = #13;
```

```
    HFA_handshake_on : boolean = true;
    NAK_string = 'NAK';
    ACK_string = 'ACK';

var
    start_reaction_time,
    reaction_time,
    standard_deviation,
    sensitivity_value : real;
    response : Yes_or_No;
    temp1,temp2,
    coord_str : string;
    ComPort,
    ComParam : word;

procedure timer;

begin { TIMER }
    RT_sum := reaction_time + RT_sum;
    if total_presentations > 0 then
      mean_reaction_time := RT_sum/total_presentations;
    test_time := RealTime - start_time;
  end; { TIMER } function get_HFA_string : string;
  var
    ch : char;
    i : integer;
    s : string;
    t0 : real;
begin
  ch := ' ';
  s := '';
  t0 := realtime;
  repeat
    if ComReady then
                begin
                  ch := ReadCom;
                  if ch<>CR then s:=s+ch;
                end;
  until ((ch = CR) or keypressed) { read: ACK|NAK + CR }
        or ((realtime-t0)>2.0); { ...second time out }
  get_HFA_string := s;
  GotoXY(1,22); Write('':39);
  GotoXY(1,22); Write(S);
end;

function Button_Pressed : boolean;
  var
    msg : string;
    t,i : integer;
begin
  repeat
    WriteComStr('BT'+CR);
    repeat until ComReady or keypressed; { wait for anything from HFA }
    msg := get_HFA_string;
```

```
    if msg[1]<> 'N' then
      begin
        if msg[1] = 'C' then
          case msg[3] of
            '0' : Button_Pressed := false;  { not pressed since last flash }
            '1' : Button_Pressed := true;   { not pressed now but has been
                                              since last flash }
            '2' : Button_Pressed := true    { now being pressed }
            else Button_Pressed := false;   { Error! }
            t := 2000;
          end
        else {get time}
          begin
            Button_pressed := true;
            t := 0;
            for i := 1 to length(msg) do t := t*10 + ord(msg[i])-ord('0');
            reaction_time := stimulus_duration + t/1000.0
          end;
        msg := get_HFA_string;
      end;
  until msg = ACK_string;
end;
  Procedure SendHFACom(S:String);
  begin
    repeat
      WriteComStr(S+CR);
    until get_HFA_string = ACK_string;
    GotoXY(1,20); Write('':39);
    GotoXY(1,20); Write(S);
  end;

begin { RESPOND }

{ prep. for stimulus }
  sensitivity_value := current_stimulus.sensitivity;
  variation_in_sensitivity := 0; { unknown value! }
  FA_flaged := false;
  MISS_flaged := false;
  textcolor(lightgreen);
  if not HFA_initialized then
    begin { ready HFA }
      HFA_initialized := true;
      ComPort := Com2Port;
      ComParam := Baud9600+NoParity+WordSize8+StopBits1;
      GotoXY(1,17);
      if OpenCom(ComPort,ComParam) then Write('ComPort Open.');
      while comready do ch := readcom;
      SendHFACom('SL');
      Str(TRUNC((max_RT+stimulus_duration)*1000):0,temp1);
      Str(TRUNC((stimulus_duration*1000)):0,temp2);
      SendHFACom('AP3 BD'+temp1+' DR'+temp2);
    end;
{ move to new location }
  Str(Current_stimulus.radius:0,temp1);
  Str(Current_stimulus.meridian:0,temp2);
```

```
    coord_str := temp2 + ',' + temp1;            { theta,range }
  { set luminance level }
  Str(Current_stimulus.luminance:0,temp1);
  SendHFACom('MP'+coord_str+' IN'+temp1+' FL');
  start_reaction_time := RealTime;

{ move to new location }
  With worksheet[next_element] do
    begin
      Str(radius:0,temp1);
      Str(meridian:0,temp2);
      coord_str := temp2 + ',' + temp1;          { theta,range }
      SendHFACom('MP'+coord_str);
    end;

{ record a response or time out }
  response := no;
  repeat
    reaction_time := RealTime - start_reaction_time;
    if Button_pressed then response := yes;
     gotoxy(1,17);Write(reaction_time:5:2);
   until (reaction_time >= max_RT) or (response = yes);

timer;

if response = yes then
     HFA_respond := target_seen
   else
     HFA_respond := target_not_seen;

{ output latest patient parameters }
   if (not batch) and (device_type <> manual) then
     begin
       gotoXY(10,17);write(mean_reaction_time:6:2);
     end;

end; { RESPOND } function Sim_Respond(current_stimulus:mod_rec) : possible_responses;

var
    standard_deviation,
    sensitivity_value,
    miss_rate,
    FA_rate,
    fatigue_psychometric,
    fatigue_RT_weighting   : real;
    response : Yes_or_No;

procedure timer;

{
Timer is a procedure for the Kraken visual field simulation program. It
handles the stimulus duration and interstimulus interval (ISI) for the test
procedure as well as examining the reaction time characteristics of the
``` patient. YES and NO responses from the Respond function can be overridden by Timer, as well as influencing the next presentation if the the response is too slow. The rountine updates the elapsed time variable.

Reaction time and pseudo timer:
   a. Two timing functions can be enabled by setting the appropriate flags. One is the patient's reaction time, the other is a pseudo-timer that keeps track of elapsed time the given test procedure.
   b. A timing window (minimum and maximum reaction time allowed for a YES response) can be set.
   c. YES or NO responses from Respond can be reversed by meeting or not meeting the timing window criterion for patient responses.
   d. The patient's reaction time can be fixed or variable. If variable, then a standard deviation is provided to Gauss (in order to sample from a normal distribution of reaction times).
   e. Reaction time can be weighted according to the following factors:
      1. patient's age.
      2. stimulus eccentricity.
      3. elapsed test time (that is, due to fatigue, boredom, etc...)
}

```
begin { TIMER }

{ Here we are at the pseudo-clock timing routine and reaction time generator.
  This is the last section before we return with our final decision about
  whether the target was or was not seen. Also, the cumulative time of the
  test (both for determining total time and for altering the fatigue factor
  when enabled) is updated. } if timing_clock_on then
    test_time := test_time + stimulus_duration + interstimulus_interval;

{ Determine a reaction time for the set of conditions specified. } if response = no then
    final_RT_value := max_RT
  else
    final_RT_value := (max_RT+min_RT)/2.0;

if reaction_time_on then
    begin if variable_reaction_time_on then
        begin if eccentricity_weighting_on then
            begin
              radial_RT_weighting := current_stimulus.radius * initial_radial_RT_weighting;
              RT_variation := RT_variation * radial_RT_weighting;
            end;

if age_weighting_on then
            begin
              age_RT_weighting := patient_rec.age * patient_rec.age * initial_age_RT_weighting;
              RT_variation := RT_variation * age_RT_weighting;
            end;
```

```
      if fatigue_weighting_on then
        RT_variation := RT_variation * fatigue_RT_weighting;

final_RT_value := gauss(RT_variation,final_RT_value);

end;

{ update mean reaction time }
  RT_sum := final_RT_value + RT_sum;
  mean_reaction_time := RT_sum/total_presentations;

{ Now, let's look at the reaction time for YES and NO trials to see if
  we should change the response, and if we should flag the next presentation
  for an erroneous YES response due to a long reaction time. Finally, the
  elapsed time indicator should be updated if reaction time was longer than
  the stimulus duration and interstimulus interval values. } if response = yes then
        begin
          if final_RT_value > (stimulus_duration + interstimulus_interval + min_RT) then
            next_FA_flag := yes    { RT falls in the next trial }
          else
            next_FA_flag := no;
          if (final_RT_value > max_RT) or (final_RT_value < min_RT) then
            response := no;        { RT falls outside of allowed window }
        end
      else { response = no }
        begin
          if next_FA_flag = yes then response := yes;
          next_FA_flag := no;
        end;

if final_RT_value < stimulus_duration then
        test_time := test_time - stimulus_duration + final_RT_value;

end; { reaction time switch on code } end; { TIMER } begin { RESPOND } sensitivity_value  := current_stimulus.sensitivity;
  standard_deviation := initial_standard_deviation;
  RT_variation       := initial_RT_variation;
  miss_rate          := initial_miss_rate;
  FA_rate            := initial_FA_rate;
  FA_flaged          := false;
  MISS_flaged        := false;

fatigue_psychometric := 1.0 + test_time * fatigue_psychometric_factor;
  fatigue_RT_weighting := 1.0 + test_time * fatigue_RT_factor;

if variable_sensitivity_on then
    begin if (current_stimulus.normal - current_stimulus.sensitivity) > loss_criterion then
        standard_deviation := standard_deviation * loss_psychometric;
```

```
    if eccentricity_weighting_on then
      begin
        radial_psychometric := current_stimulus.radius * initial_radial_psychometric;
        standard_deviation := standard_deviation * radial_psychometric;
      end;

if age_weighting_on then
      begin
        age_psychometric := patient_rec.age * patient_rec.age * initial_age_psychometric;
        standard_deviation := standard_deviation * age_psychometric;
      end;

if fatigue_weighting_on then
        begin
          standard_deviation := standard_deviation * fatigue_psychometric;
          sensitivity_value := sensitivity_value -
                            fatigue_eccentricity_loss * current_stimulus.radius * test_time;
        end;

sensitivity_value := gauss(standard_deviation, sensitivity_value);

end; { variable sensitivity }

{ Compare sensitivity value with stimulus value and derive response for
  section 1 determinations. Then go on to section 2 if YES response
  (misses section) or section 3 if NO response (false alarms section).
  Again, determinations for eccentricity, age and fatigue weightings for
  false alarms and misses are determined. } if sensitivity_value >= current_stimulus.luminance then begin { ideally, patient should be able to see this stimulus} response := yes;

{ ** the following is not to be included at present until some empirical
     justification is found.

if eccentricity_weighting_on then
      begin
        radial_miss_weighting := current_stimulus.radius * initial_radial_miss_weighting;
        miss_rate := miss_rate * radial_miss_weighting;
      end;
    if age_weighting_on then
      begin
        age_miss_weighting := patient_rec.age * patient_rec.age * initial_age_miss_weighting;
        miss_rate := miss_rate * age_miss_weighting;
      end;
}
    MISS_flaged := random <= (miss_rate-1.0);
    if MISS_flaged then response := no;

end else { ideally, patient should not be able to see this stimulus }
```

```
    begin response := no;

{ ** the following is not to be included at present until some empirical
    justification is found.

if eccentricity_weighting_on then
        begin
          radial_FA_weighting := current_stimulus.radius * initial_radial_FA_weighting;
          FA_rate := FA_rate * radial_FA_weighting;
        end;
      if age_weighting_on then
        begin
          age_FA_weighting := patient_rec.age * patient_rec.age * initial_age_FA_weighting;
          FA_rate := FA_rate * age_FA_weighting;
        end;
}
      FA_flaged := random <= (FA_rate-1.0);
      if FA_flaged then response := yes;

end;

{ Let's get reaction time characteristics taken care of and update the
  elapsed time indicator, fatigue factors, etc. } timer;

variation_in_sensitivity := round(sensitivity_value - current_stimulus.sensitivity);

if response = yes then
    Sim_respond := target_seen
  else
    Sim_respond := target_not_seen;

{ output latest patient parameters }
  if (not batch) and (device_type <> manual) then
    begin
      textcolor(lightgreen);
      gotoXY(5,19);
      if fatigue_weighting_on then
              write(fatigue_psychometric:6:0,
                    fatigue_RT_weighting:6:0);

gotoXY(5,20);
      if age_weighting_on then
              write(age_psychometric:6:0,
                    age_RT_weighting:6:0,
                    age_miss_weighting:6:0,
                    age_FA_weighting:6:0);

gotoXY(5,21);
      if eccentricity_weighting_on then
              write(radial_psychometric:6:0,
                    radial_RT_weighting:6:0,
                    radial_miss_weighting:6:0,
                    radial_FA_weighting:6:0);
```

```
        gotoXY(1,24);write(mean_reaction_time:6:2,
                    miss_rate-1.0:6:2,
                    FA_rate-1.0:6:2,
                    standard_deviation:6:2);
    end;

{
WITH CURRENT_STIMULUS DO
  WRITE(LST,'[',RADIUS:2,',',MERIDIAN:3,'] ',LUMINANCE:4,
            ' | ',SENSITIVITY:4,SENSITIVITY_VALUE:7:2,' | ');
  IF RESPONSE = YES THEN WRITELN(LST,'SEEN') ELSE WRITELN(LST,'NOT SEEN');
} end; { RESPOND } function respond {(current_stimulus:mod_rec) : possible_responses};
  var
    temp_respond : possible_responses;

begin
  case Respond_type of
    Simulation : temp_respond := Sim_respond(current_stimulus);
    HFA        : temp_respond := HFA_respond(current_stimulus);
    HJPP       : temp_respond := HJPP_respond(current_stimulus);
  end;

with current_stimulus do
    if (luminance = upper_limit) or
       (luminance = lower_limit) then
      writeln(response_file,(luminance div upper_limit):0,',',
              ((temp_respond AND target_seen) div target_seen):0);

respond := temp_respond;

end;

begin
end.
unit pause;

interface
uses DOS,TPDos,TPCrt,graph;

procedure pause_for_any_key;

implementation procedure screen_print;
    const
      esc : char = #27;

var
      out : text;
      nbytes,
      data,bit,
```

```
    i,x,y : integer;
    viewport : viewporttype;

begin
  assign(out,'LPT1');
  rewrite(out);

nbytes := GetMaxX div 8;
  write(out,esc,'*t100R');
  write(out,esc,'*r0A');
  GetViewSettings(ViewPort);
  SetViewPort(0,0,GetMaxX,GetMaxY,True);

for y := 0 to GetMaxY-1 do
    begin
      write(out,esc,'*b',nbytes+1:0,'W');
      for x := 0 to nbytes do
        begin
          data := 0;
          for i := 0 to 7 do
            begin
              if GetPixel((x*8+i),y)=0 then
                bit := 0
              else
                bit := 1;
              data := data + trunc(bit*exp((7-i)*ln(2)));
            end;
          write(out,chr(data):0);
        end;
    end;

write(out,esc,'*rB');
  write(out,esc,'E');
  With ViewPort do
    SetViewPort(x1,y1,x2,y2,clip);
  close(out);
end;

procedure pause_for_any_key;
  var
    ch     : char;
    co : integer;
    done   : boolean;
    regtemp : registers;
    msg    : string;

begin
  co := 1;
  done := false;
  msg  := 'Press any key to continue ([P]rint)';
  repeat
    repeat
      textcolor(co);
      if co = 15 then co := 0;
      Inc(co);
      GotoXY(1,25);  Write(msg);
```

```
    delay(150);
  until keypressed;
  Sound(880); Delay(10); NoSound; { microbeep! }
  ch := Readkey;
  GotoXY(1,25);
  Write('                              ');
  case ch of
    'P','p' : begin
              screen_print;
              Sound(440);delay(50);NoSound;
            end
    else done := true;
  end;
    until done;
  end;
end.
```

APPENDIX C

Normal Reference Values by Age Group

The following is the 30-2 pattern (76 locations, 6 degrees between each location, horizontally and vertically). Each number represents the location index used in the reference values table (which follows). This pattern represents the spatial layout of locations for stimuli presentation to a right eye. To obtain the format for a left eye, simply apply a horizontal mirror-image transformation on the location indices.

```
                        38   18   69   73
                   54   34   14   57   61   65
              66   50   30   10   41   45   49   53
         74   62   46   26    6   21   25   29   33   37
         70   58   42   22    2    1    5    9   13   17
         19   15   11    7    3    4   24   44   60   72
         39   35   31   27   23    8   28   48   64   76
              55   51   47   43   12   32   52   68
                   67   63   59   16   36   56
                        75   71   20   40
```

Normal Sensitivity Reference Values: (in dB units)

| Location Index | Age Group | | | | | | |
|---|---|---|---|---|---|---|---|
| | 00-20 | 21-30 | 31-40 | 41-50 | 51-60 | 61-70 | 71-99 |
| 1 | 38 | 38 | 38 | 37 | 36 | 35 | 33 |
| 2 | 38 | 37 | 38 | 37 | 36 | 35 | 33 |
| 3 | 38 | 37 | 38 | 37 | 36 | 35 | 33 |
| 4 | 38 | 37 | 37 | 37 | 36 | 35 | 33 |
| 5 | 36 | 36 | 35 | 35 | 33 | 33 | 31 |
| 6 | 36 | 35 | 35 | 35 | 34 | 33 | 31 |
| 7 | 36 | 35 | 36 | 35 | 34 | 34 | 31 |
| 8 | 36 | 35 | 35 | 35 | 34 | 33 | 31 |
| 9 | 25 | 22 | 24 | 21 | 20 | 20 | 20 |
| 10 | 34 | 33 | 33 | 33 | 31 | 30 | 28 |

201                                                                 202

| | | | | | | | |
|---|---|---|---|---|---|---|---|
| 11 | 34 | 34 | 34 | 33 | 32 | 31 | 29 |
| 12 | 34 | 33 | 34 | 33 | 32 | 31 | 29 |
| 13 | 33 | 33 | 33 | 33 | 31 | 31 | 28 |
| 14 | 32 | 31 | 30 | 30 | 29 | 28 | 26 |
| 15 | 32 | 32 | 32 | 31 | 30 | 29 | 27 |
| 16 | 33 | 32 | 32 | 32 | 30 | 29 | 27 |
| 17 | 33 | 32 | 32 | 32 | 30 | 30 | 26 |
| 18 | 29 | 28 | 28 | 28 | 26 | 26 | 23 |
| 19 | 30 | 30 | 29 | 29 | 27 | 27 | 24 |
| 20 | 31 | 30 | 30 | 30 | 28 | 28 | 25 |
| 21 | 36 | 35 | 35 | 35 | 34 | 33 | 31 |
| 22 | 36 | 35 | 36 | 35 | 34 | 34 | 31 |
| 23 | 36 | 35 | 36 | 35 | 34 | 34 | 31 |
| 24 | 35 | 33 | 34 | 33 | 31 | 30 | 28 |
| 25 | 35 | 34 | 34 | 34 | 33 | 32 | 29 |
| 26 | 35 | 34 | 34 | 34 | 33 | 32 | 29 |
| 27 | 35 | 34 | 34 | 34 | 33 | 32 | 29 |
| 28 | 35 | 35 | 35 | 34 | 33 | 33 | 30 |
| 29 | 34 | 34 | 33 | 33 | 32 | 31 | 29 |
| 30 | 33 | 32 | 32 | 32 | 31 | 30 | 28 |
| 31 | 34 | 33 | 33 | 32 | 31 | 30 | 28 |
| 32 | 34 | 33 | 33 | 33 | 32 | 31 | 28 |
| 33 | 33 | 32 | 32 | 32 | 31 | 30 | 27 |
| 34 | 31 | 30 | 30 | 30 | 28 | 27 | 25 |
| 35 | 32 | 31 | 31 | 30 | 29 | 28 | 26 |
| 36 | 33 | 32 | 32 | 31 | 30 | 29 | 26 |
| 37 | 32 | 31 | 31 | 31 | 30 | 29 | 26 |
| 38 | 29 | 28 | 28 | 28 | 26 | 25 | 22 |
| 39 | 30 | 29 | 29 | 29 | 27 | 26 | 24 |
| 40 | 31 | 30 | 30 | 30 | 28 | 28 | 25 |
| 41 | 34 | 33 | 33 | 33 | 32 | 30 | 28 |
| 42 | 34 | 34 | 33 | 33 | 32 | 31 | 29 |
| 43 | 34 | 33 | 34 | 33 | 32 | 31 | 29 |
| 44 | 24 | 20 | 20 | 20 | 19 | 18 | 20 |
| 45 | 33 | 33 | 32 | 32 | 31 | 30 | 28 |
| 46 | 34 | 33 | 33 | 32 | 31 | 30 | 28 |
| 47 | 34 | 33 | 33 | 32 | 31 | 30 | 28 |
| 48 | 34 | 33 | 33 | 33 | 32 | 31 | 28 |
| 49 | 33 | 32 | 32 | 32 | 30 | 29 | 27 |
| 50 | 32 | 31 | 31 | 31 | 30 | 28 | 26 |
| 51 | 32 | 31 | 31 | 31 | 29 | 29 | 27 |
| 52 | 33 | 33 | 33 | 32 | 31 | 30 | 28 |
| 53 | 32 | 31 | 31 | 31 | 29 | 28 | 26 |
| 54 | 30 | 29 | 29 | 29 | 27 | 26 | 24 |
| 55 | 31 | 30 | 30 | 29 | 28 | 27 | 25 |
| 56 | 32 | 31 | 31 | 31 | 29 | 29 | 26 |
| 57 | 32 | 31 | 30 | 30 | 29 | 28 | 26 |
| 58 | 32 | 32 | 31 | 31 | 30 | 29 | 27 |
| 59 | 32 | 32 | 32 | 32 | 30 | 29 | 27 |
| 60 | 34 | 33 | 33 | 33 | 31 | 31 | 28 |
| 61 | 31 | 30 | 30 | 30 | 29 | 28 | 25 |
| 62 | 32 | 31 | 31 | 30 | 29 | 28 | 26 |
| 63 | 32 | 31 | 31 | 31 | 29 | 28 | 26 |
| 64 | 34 | 33 | 33 | 32 | 31 | 30 | 27 |
| 65 | 31 | 30 | 30 | 30 | 28 | 27 | 25 |
| 66 | 31 | 29 | 29 | 29 | 28 | 27 | 24 |
| 67 | 31 | 30 | 30 | 29 | 28 | 27 | 25 |

| 203 | | | | | | | 204 |
|---|---|---|---|---|---|---|---|
| 68 | 33 | 32 | 32 | 32 | 30 | 29 | 26 |
| 69 | 29 | 29 | 28 | 28 | 26 | 26 | 23 |
| 70 | 30 | 29 | 29 | 29 | 27 | 27 | 24 |
| 71 | 31 | 30 | 30 | 30 | 28 | 28 | 25 |
| 72 | 33 | 32 | 32 | 32 | 30 | 30 | 26 |
| 73 | 29 | 28 | 28 | 28 | 26 | 25 | 23 |
| 74 | 30 | 29 | 29 | 29 | 27 | 26 | 24 |
| 75 | 30 | 29 | 29 | 29 | 27 | 27 | 24 |
| 76 | 32 | 32 | 32 | 32 | 30 | 29 | 26 |

It is claimed:

1. A method of testing a subject's threshold response level to a visual stimulus which can be presented to the subject at a selected level and at selected locations in a visual field, comprising
   (a) partitioning the field into an array of N locations composed of S seed locations and N-S non-seed locations, where each seed location has multiple nearest-neighbor non-seed locations,
   (b) determining, at each seed location, a threshold value of detection of a visual stimulus by the subject being tested,
   (c) calculating the expected threshold values of detection by the subject at each non-seed location,
   (d) presenting at each non-seed location a visual stimulus which is either a selected level above or below the expected threshold value of detection for that non-seed location, depending on whether that non-seed location has been assigned to a super- or sub-threshold group, respectively,
   (e) recording the response of the subject to each presented stimulus as "seen" or "not seen,"
   (f) classifying the neighbor agreement between each location in the field and its nearest neighbors into a "low-confidence" or "high-confidence" class,
   (g) if the pattern of neighbor agreement for non-seed location is in the low-confidence category, adjusting the expected threshold of that location to a revised expected threshold value, and retesting the nearest-neighbor agreement between the revised-threshold location and its nearest neighbors.

2. The method of claim 1, wherein the classes into which the neighborhood agreement can be classified further include a "discrepancy" class, which further includes a step (h) of retesting a location which is classified in the "discrepancy" class.

3. The method of claim 2, for use in visual field perimetry testing, wherein said two-dimensional spatial field which substantially overlaps the subject's visual field, and the field is partitioned into 50–100 regularly-spaced locations with each seed point being bordered by at least 6–8 neighbors.

4. The method of claim 3, wherein said field is partitioned into a regular rectangular array of locations, with any give location being bordered by four orthogonal nearest neighbors of the same expected response group four diagonal nearest neighbors of the opposite expected response group.

5. The method of claim 2, wherein said determining includes measuring upper and lower boundaries of detection by the subject of the intensity of a short-duration flash of light at each seed location.

6. The method of claim 5, wherein the expected threshold intensity value of light-stimulus detection at each nearest-neighbor location is determined from (i) the threshold values of nearby seed locations, (ii) the distances of the nearest-neighbor location from the nearby seed locations, and (iii), a position-related change in threshold range which would be expected in an average normal subject.

7. The method of claim 2, wherein the discrepancy category is defined by complete disagreement with a center location and its nearest neighbors.

8. The method of claim 7, which further includes reversing the assignment of the sub- and supra-threshold groups, and repeating steps (d)-(h), where the selected level of stimulus above or below threshold which is presented at each non-seed location is (i) the original selected level for non-seed locations which are nearest neighbors of locations classified as low-confidence, and (ii) a reduced selected level for non-seed locations which are nearest neighbors of locations classified as high-confidence levels.

9. The method of claim 8, which further includes reversing the assignment of the sub- and suprathreshold groups to their original assignments, and repeating steps (d)-(h) for nearest neighbors of locations which are classified as low-confidence.

10. The method of claim 8, wherein a non-seed location originally classified as a discrepancy location is classified as a discrepancy location after repeating steps (d)-(h), which further includes determining, at that location a threshold value of detection of a visual stimulus by the subject being tested.

11. The method of claim 1, wherein said determining is carried out by a optimized modified binary search procedure.

12. Apparatus for testing a subject's threshold response level to a visual stimulus which can be presented to the subject at a selected level and at selected locations in a two-dimensional field, comprising
   (a) presenting means for presenting a selected-level stimulus at each of N locations in a two-dimensional visual field array,
   (b) recording means for recording the response of the subject to the stimuli presented at locations in the field as "seen" or "not seen," and (c) a control unit which operates to (1) store, at each of S seed locations in the N location array, a subject's upper and lower boundaries of stimulus detection, (2) calculate, for each of N-S non-seed nearest neighbor locations in the array, the expected threshold value of detection by the subject, based on the values stored in said storing means, (3) present to the subject, at each non-seed location, a visual stimulus which is either a selected level above or below the expected threshold value of detection for that non-seed location, depending on whether that non-seed location has been assigned to a super- or sub-threshold group, respectively, (4) classify the neighbor agreement between each location in the field and its nearest neighbors into a "discrepancy," "low-confidence," or "high-confidence" category, (5) if the pattern of neighbor agreement at any location is in the discrepancy category, retest that location for "seen"/"not-seen" response, and (6) if the pattern of neighbor agreement for non-seed location is in the low-confidence category, adjust the expected threshold of that location to a revised expected threshold value, and retesting the nearest-neighbor agreement between the revised-threshold location and its nearest neighbors.

13. The apparatus of claim 12, wherein the visual field array is a hemispherical surface cap region, and said presenting means includes a means for producing a selected-intensity light stimulus at selected locations in the surface cap region.

14. The apparatus of claim 13, wherein said producing means is a swinging-arm assembly having a light-stimulus source, and the assembly is designed to move the light source between any two locations in the cap region within a period of less than about 10 sec.

15. The apparatus of claim 14, wherein said presenting means includes a second light source which is fixed in the field, and means for focusing the two light sources coordinately for a subject being tested, and the apparatus further includes a transparent viewing screen through which the two light sources are viewed by the subject.

* * * * *